US010258637B2

(12) United States Patent
Broedl et al.

(10) Patent No.: US 10,258,637 B2
(45) Date of Patent: *Apr. 16, 2019

(54) PHARMACEUTICAL COMPOSITION, METHODS FOR TREATING AND USES THEREOF

(71) Applicant: Boehringer Ingelheim International GmbH, Ingelheim am Rhein (DE)

(72) Inventors: Uli Christian Broedl, Mainz am Rhein (DE); Sreeraj Macha, Basking Ridge, NJ (US); Maximilian von Eynatten, Wiesbaden (DE); Hans-Juergen Woerle, Grandvaux (CH)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/918,401

(22) Filed: Mar. 12, 2018

(65) Prior Publication Data

US 2018/0200278 A1 Jul. 19, 2018

Related U.S. Application Data

(63) Continuation of application No. 14/918,727, filed on Oct. 21, 2015, now Pat. No. 9,949,998, which is a continuation of application No. 14/244,208, filed on Apr. 3, 2014, now abandoned.

(60) Provisional application No. 61/908,991, filed on Nov. 26, 2013, provisional application No. 61/808,804, filed on Apr. 5, 2013.

(51) Int. Cl.
*A61K 31/7034* (2006.01)
*A61K 31/7048* (2006.01)
*A61K 9/20* (2006.01)
*A61K 9/28* (2006.01)

(52) U.S. Cl.
CPC ........ *A61K 31/7048* (2013.01); *A61K 9/2018* (2013.01); *A61K 9/2866* (2013.01); *A61K 31/7034* (2013.01)

(58) Field of Classification Search
None
See application file for complete search history.

(56) References Cited

U.S. PATENT DOCUMENTS

| | | |
|---|---|---|
| 3,174,901 A | 3/1965 | Sterne |
| 3,884,906 A | 5/1975 | Van Der Meer et al. |
| 4,379,785 A | 4/1983 | Weyer et al. |
| 4,602,023 A | 7/1986 | Kiely et al. |
| 4,639,436 A | 1/1987 | Junge et al. |
| 4,786,023 A | 11/1988 | Harris et al. |
| 4,786,755 A | 11/1988 | Kiely et al. |
| 5,145,684 A | 9/1992 | Liversidge et al. |
| 5,807,580 A | 9/1998 | Luber |
| 5,880,289 A | 3/1999 | Kaneko et al. |
| 6,414,126 B1 | 7/2002 | Ellsworth et al. |
| 6,498,193 B2 | 12/2002 | Beisswenger et al. |
| 6,515,117 B2 | 2/2003 | Ellsworth et al. |
| 6,613,806 B1 | 9/2003 | Aven et al. |
| 6,627,611 B2 | 9/2003 | Tomiyama et al. |
| 6,774,112 B2 | 8/2004 | Gougoutas |
| 6,794,480 B2 | 9/2004 | Goto et al. |
| 6,936,590 B2 | 8/2005 | Washburn et al. |
| 6,972,283 B2 | 12/2005 | Fujikura et al. |
| 6,995,183 B2 | 2/2006 | Hamann et al. |
| 7,101,856 B2 | 9/2006 | Glombik et al. |
| 7,169,761 B2 | 1/2007 | Tomiyama et al. |
| 7,202,350 B2 | 4/2007 | Imamura et al. |
| 7,294,618 B2 | 11/2007 | Fushimi et al. |
| 7,371,732 B2 | 5/2008 | Eickelmann et al. |
| 7,375,087 B2 | 5/2008 | Teranishi et al. |
| 7,375,090 B2 | 5/2008 | Himmelsbach et al. |
| 7,375,213 B2 | 5/2008 | Deshpande et al. |
| 7,393,836 B2 | 7/2008 | Eckhardt et al. |
| 7,407,955 B2 | 8/2008 | Himmelsbach et al. |
| 7,417,032 B2 | 8/2008 | Eckhardt et al. |
| 7,419,959 B2 | 9/2008 | Eckhardt et al. |
| 7,541,341 B2 | 6/2009 | Fushimi et al. |
| 7,579,449 B2 | 8/2009 | Eckhardt et al. |
| 7,589,193 B2 | 9/2009 | Washburn et al. |
| 7,662,790 B2 | 2/2010 | Himmelsbach et al. |
| 7,674,486 B2 | 3/2010 | Bhaskaran et al. |
| 7,683,160 B2 | 3/2010 | Eckhardt et al. |
| 7,687,469 B2 | 3/2010 | Eckhardt et al. |
| 7,713,938 B2 | 5/2010 | Himmelsbach et al. |
| 7,723,309 B2 | 5/2010 | Himmelsbach et al. |
| 7,723,379 B2 | 5/2010 | Romanczyk, Jr. et al. |
| 7,745,414 B2 | 6/2010 | Eckhardt et al. |
| 7,772,191 B2 | 8/2010 | Eckhardt et al. |
| 7,772,192 B2 | 8/2010 | Esko |
| 7,772,378 B2 | 8/2010 | Himmelsbach et al. |
| 7,772,407 B2 | 8/2010 | Imamura et al. |
| 7,776,830 B2 | 8/2010 | Eckhardt et al. |
| 7,847,074 B2 | 12/2010 | Eckhardt et al. |
| 7,851,502 B2 | 12/2010 | Bindra et al. |
| 7,851,602 B2 | 12/2010 | Himmelsbach et al. |
| 7,858,587 B2 | 12/2010 | Eckhardt et al. |
| 7,879,806 B2 | 2/2011 | Himmelsbach et al. |

(Continued)

FOREIGN PATENT DOCUMENTS

| | | |
|---|---|---|
| CA | 2382480 A1 | 3/2001 |
| CA | 2388818 A1 | 4/2001 |

(Continued)

OTHER PUBLICATIONS

Harris, Maureen I. "Classification, Diagnostic Criteria, and Screening for Diabetes" (1995) Diabetes in America, 2nd Edition, pp. 15-36.

(Continued)

*Primary Examiner* — Traviss C McIntosh, III
(74) *Attorney, Agent, or Firm* — Edouard G. Lebel

(57) ABSTRACT

The present invention relates to certain SGLT-2 inhibitors for treating and/or preventing metabolic disorders, such as type 1 or type 2 diabetes mellitus or pre-diabetes, in patients with renal impairment or chronic kidney disease (CKD).

24 Claims, 17 Drawing Sheets

(56) References Cited

U.S. PATENT DOCUMENTS

| | | |
|---|---|---|
| 7,879,807 B2 | 2/2011 | Himmelsbach et al. |
| 8,039,441 B2 | 10/2011 | Himmelsbach et al. |
| 8,119,648 B2 | 2/2012 | Himmelsbach et al. |
| 8,178,541 B2 | 5/2012 | Himmelsbach et al. |
| 8,232,281 B2 | 7/2012 | Dugi et al. |
| 8,283,326 B2 | 10/2012 | Eckhardt et al. |
| 8,507,450 B2 | 8/2013 | Eckhardt et al. |
| 8,551,957 B2 | 10/2013 | Dugi et al. |
| 8,557,782 B2 | 10/2013 | Eckhardt et al. |
| 8,802,842 B2 | 8/2014 | Weber et al. |
| 9,024,010 B2 | 5/2015 | Weber et al. |
| 9,034,883 B2 | 5/2015 | Klein et al. |
| 9,127,034 B2 | 9/2015 | Eckhardt et al. |
| 9,192,616 B2 | 11/2015 | Johnson |
| 9,192,617 B2 | 11/2015 | Mayoux et al. |
| 9,949,997 B2 | 4/2018 | Broedl et al. |
| 9,949,998 B2 * | 4/2018 | Broedl ............... A61K 31/7048 |
| 2001/0018090 A1 | 8/2001 | Noda et al. |
| 2001/0041674 A1 | 11/2001 | Tomiyama et al. |
| 2001/0044435 A1 | 11/2001 | Himmelsbach et al. |
| 2002/0137903 A1 | 9/2002 | Ellsworth et al. |
| 2002/0173509 A1 | 11/2002 | Himmelsbach et al. |
| 2002/0198205 A1 | 12/2002 | Himmelsbach et al. |
| 2003/0064935 A1 | 4/2003 | Gougoutas |
| 2003/0087843 A1 | 5/2003 | Washburn |
| 2003/0114390 A1 | 6/2003 | Washburn et al. |
| 2003/0212070 A1 | 11/2003 | Schwink et al. |
| 2004/0097510 A1 | 5/2004 | Himmelsbach et al. |
| 2004/0138148 A1 | 7/2004 | Fushimi et al. |
| 2004/0138439 A1 | 7/2004 | Deshpande et al. |
| 2004/0247677 A1 | 12/2004 | Oury et al. |
| 2005/0065098 A1 | 3/2005 | Fujikura et al. |
| 2005/0085680 A1 | 4/2005 | Auerbach et al. |
| 2005/0124555 A1 | 6/2005 | Tomiyama et al. |
| 2005/0187168 A1 | 8/2005 | Eickelmann et al. |
| 2005/0209166 A1 | 9/2005 | Eckhardt et al. |
| 2005/0233982 A1 | 10/2005 | Himmelsbach et al. |
| 2005/0234108 A1 | 10/2005 | Himmelsbach et al. |
| 2006/0009400 A1 | 1/2006 | Eckhardt et al. |
| 2006/0019948 A1 | 1/2006 | Eckhardt et al. |
| 2006/0025349 A1 | 2/2006 | Eckhardt et al. |
| 2006/0035841 A1 | 2/2006 | Eckhardt et al. |
| 2006/0063722 A1 | 3/2006 | Washburn et al. |
| 2006/0074031 A1 | 4/2006 | Eckhardt et al. |
| 2006/0079541 A1 | 4/2006 | Langkopf et al. |
| 2006/0142210 A1 | 6/2006 | Eckhardt et al. |
| 2006/0189548 A1 | 8/2006 | Himmelsbach et al. |
| 2006/0210627 A1 | 9/2006 | Pfeffer et al. |
| 2006/0234953 A1 | 10/2006 | Himmelsbach et al. |
| 2006/0251728 A1 | 11/2006 | Himmelsbach et al. |
| 2006/0258749 A1 | 11/2006 | Eckhardt et al. |
| 2006/0287242 A1 | 12/2006 | Ewing et al. |
| 2007/0004648 A1 | 1/2007 | Himmelsbach et al. |
| 2007/0027092 A1 | 2/2007 | Himmelsbach et al. |
| 2007/0042042 A1 | 2/2007 | Jo et al. |
| 2007/0049537 A1 | 3/2007 | Eckhardt et al. |
| 2007/0054867 A1 | 3/2007 | Eckhardt et al. |
| 2007/0073046 A1 | 3/2007 | Eckhardt et al. |
| 2007/0249544 A1 | 10/2007 | Himmelsbach et al. |
| 2007/0259821 A1 | 11/2007 | Eckhardt et al. |
| 2007/0281940 A1 | 12/2007 | Dugi et al. |
| 2008/0058379 A1 | 3/2008 | Eckhardt et al. |
| 2008/0107731 A1 | 5/2008 | Kohlrausch et al. |
| 2008/0234367 A1 | 9/2008 | Washburn et al. |
| 2008/0287529 A1 | 11/2008 | Deshpande et al. |
| 2009/0023913 A1 | 1/2009 | Eckhardt et al. |
| 2009/0137499 A1 | 5/2009 | Honda et al. |
| 2009/0281078 A1 | 11/2009 | Routledge et al. |
| 2009/0318547 A1 | 12/2009 | Eckhardt et al. |
| 2009/0326215 A1 | 12/2009 | Eckhardt et al. |
| 2010/0069310 A1 | 3/2010 | Himmelsbach et al. |
| 2010/0074950 A1 | 3/2010 | Sesha |
| 2010/0081625 A1 | 4/2010 | Wienrich et al. |
| 2010/0093654 A1 | 4/2010 | Himmelsbach et al. |
| 2010/0099641 A1 | 4/2010 | Himmelsbach et al. |
| 2010/0179191 A1 | 7/2010 | Himmelsbach et al. |
| 2010/0209506 A1 | 8/2010 | Eisenreich |
| 2010/0240879 A1 | 9/2010 | Eckhardt et al. |
| 2010/0249392 A1 | 9/2010 | Eckhardt et al. |
| 2010/0298243 A1 | 11/2010 | Manuchehri et al. |
| 2010/0317847 A1 | 12/2010 | Eckhardt et al. |
| 2011/0014284 A1 | 1/2011 | Eisenreich et al. |
| 2011/0015225 A1 | 1/2011 | Murata et al. |
| 2011/0046076 A1 | 2/2011 | Eickelmann et al. |
| 2011/0046087 A1 | 2/2011 | Eickelmann et al. |
| 2011/0065731 A1 | 3/2011 | Dugi et al. |
| 2011/0077212 A1 | 3/2011 | Seed et al. |
| 2011/0098240 A1 | 4/2011 | Dugi et al. |
| 2011/0178033 A1 | 7/2011 | Eckhardt et al. |
| 2011/0195917 A1 | 8/2011 | Dugi et al. |
| 2011/0206766 A1 | 8/2011 | Friedl et al. |
| 2011/0236477 A1 | 9/2011 | Schneider et al. |
| 2011/0237526 A1 | 9/2011 | Weber et al. |
| 2011/0237789 A1 | 9/2011 | Weber et al. |
| 2012/0041069 A1 | 2/2012 | Sesha |
| 2012/0071403 A1 | 3/2012 | Strumph et al. |
| 2012/0094894 A1 | 4/2012 | Graefe-Mody et al. |
| 2012/0121530 A1 | 5/2012 | Klein et al. |
| 2012/0196812 A1 | 8/2012 | Eickelmann et al. |
| 2012/0219622 A1 | 8/2012 | Kohlrausch et al. |
| 2012/0283169 A1 | 11/2012 | Grempler et al. |
| 2012/0296080 A1 | 11/2012 | Eckhardt et al. |
| 2013/0035281 A1 | 2/2013 | Klein et al. |
| 2013/0035298 A1 | 2/2013 | Broedl et al. |
| 2013/0064887 A1 | 3/2013 | Ito et al. |
| 2013/0096076 A1 | 4/2013 | Dugi et al. |
| 2013/0137646 A1 | 5/2013 | Wienrich et al. |
| 2013/0236543 A1 | 9/2013 | Ito et al. |
| 2013/0252908 A1 | 9/2013 | Mayoux et al. |
| 2014/0031301 A1 | 1/2014 | Eickelmann et al. |
| 2014/0038911 A1 | 2/2014 | Eickelmann et al. |
| 2014/0046046 A1 | 2/2014 | Eckhardt et al. |
| 2014/0087996 A1 | 3/2014 | Klein et al. |
| 2014/0088027 A1 | 3/2014 | Grempler et al. |
| 2014/0256624 A1 | 9/2014 | Grempler et al. |
| 2014/0303097 A1 | 10/2014 | Broedl et al. |
| 2014/0303098 A1 | 10/2014 | Broedl et al. |
| 2014/0315832 A1 | 10/2014 | Broedl et al. |
| 2015/0272977 A1 | 10/2015 | Reiche et al. |
| 2015/0322053 A1 | 11/2015 | Eckhardt et al. |
| 2016/0000816 A1 | 1/2016 | Broedl et al. |
| 2016/0030385 A1 | 2/2016 | Manuchehri et al. |
| 2016/0038523 A1 | 2/2016 | Broedl et al. |
| 2016/0038524 A1 | 2/2016 | Broedl et al. |
| 2016/0038525 A1 | 2/2016 | Broedl et al. |
| 2016/0074415 A1 | 3/2016 | Wienrich et al. |
| 2017/0020907 A1 | 1/2017 | Eickelmann et al. |
| 2017/0095424 A1 | 4/2017 | Ito et al. |
| 2017/0106009 A1 | 4/2017 | Mayoux |
| 2017/0189437 A1 | 7/2017 | Manuchehri et al. |
| 2017/0266152 A1 | 9/2017 | Broedl et al. |
| 2017/0305952 A1 | 10/2017 | Klein et al. |
| 2017/0333465 A1 | 11/2017 | Broedl et al. |
| 2018/0104249 A1 | 4/2018 | Eisenreich |
| 2018/0104268 A1 | 4/2018 | Mayoux et al. |
| 2018/0125813 A1 | 5/2018 | von Eynatten et al. |
| 2018/0169126 A1 | 6/2018 | Broedl et al. |
| 2018/0177794 A1 | 6/2018 | Wienrich et al. |
| 2018/0185291 A1 | 7/2018 | Ito et al. |
| 2018/0193427 A1 | 7/2018 | Grempler et al. |
| 2018/0214468 A1 | 8/2018 | Broedl et al. |
| 2018/0289678 A1 | 10/2018 | Eisenreich et al. |
| 2018/0318251 A1 | 11/2018 | Broedl et al. |
| 2018/0344647 A1 | 12/2018 | Boeck et al. |

FOREIGN PATENT DOCUMENTS

| | | |
|---|---|---|
| CA | 2402609 A1 | 9/2001 |
| CA | 2423568 A1 | 4/2002 |
| CA | 2437240 A1 | 8/2002 |
| CA | 2494177 A1 | 2/2004 |
| CA | 2496249 A1 | 3/2004 |
| CA | 2470365 A1 | 6/2004 |
| CA | 2508024 A1 | 6/2004 |

(56) References Cited

FOREIGN PATENT DOCUMENTS

| | | |
|---|---|---|
| CA | 2508226 A1 | 6/2004 |
| CA | 2526145 A1 | 9/2004 |
| CA | 2539032 A1 | 3/2005 |
| CA | 2548353 A1 | 7/2005 |
| CA | 2557269 A1 | 9/2005 |
| CA | 2557320 A1 | 9/2005 |
| CA | 2557801 A1 | 10/2005 |
| CA | 2569915 A1 | 1/2006 |
| CA | 2572149 A1 | 1/2006 |
| CA | 2572819 A1 | 1/2006 |
| CA | 2573777 A1 | 2/2006 |
| CA | 2574451 A1 | 2/2006 |
| CA | 2574500 A1 | 4/2006 |
| CA | 2586938 A1 | 5/2006 |
| CA | 2649922 A1 | 11/2007 |
| CA | 2651019 A1 | 11/2007 |
| CA | 2720450 A1 | 10/2009 |
| CN | 1930141 A | 3/2007 |
| CN | 101503399 A | 8/2009 |
| CN | 101638423 A | 2/2010 |
| DE | 2758025 A1 | 7/1979 |
| DE | 2951135 A1 | 6/1981 |
| EP | 0206567 A2 | 12/1986 |
| EP | 1224195 B | 7/2002 |
| EP | 1344780 A1 | 9/2003 |
| EP | 1385856 A | 2/2004 |
| EP | 1553094 A1 | 7/2005 |
| EP | 1564210 A1 | 8/2005 |
| EP | 1609785 A1 | 12/2005 |
| EP | 1791852 A2 | 6/2007 |
| EP | 1803729 A1 | 7/2007 |
| EP | 1852108 A1 | 11/2007 |
| JP | 55007256 A | 1/1980 |
| JP | 56039056 A | 4/1981 |
| JP | 58164502 | 9/1983 |
| JP | 62030750 A | 2/1987 |
| JP | H1085502 A | 4/1998 |
| JP | 11124392 A | 5/1999 |
| JP | 2001288178 A | 10/2001 |
| JP | 2002338471 A | 11/2002 |
| JP | 2003511458 A | 3/2003 |
| JP | 2004196788 A | 7/2004 |
| JP | 2004359630 | 12/2004 |
| JP | 2005002092 A | 1/2005 |
| JP | 2005060625 A | 3/2005 |
| JP | 2006176443 A | 7/2006 |
| JP | 2008540373 A | 11/2008 |
| WO | 9831697 A1 | 7/1998 |
| WO | 0116147 A1 | 3/2001 |
| WO | 0127128 A1 | 4/2001 |
| WO | 0174834 A1 | 10/2001 |
| WO | 02064606 A1 | 8/2002 |
| WO | 2002064549 | 8/2002 |
| WO | 2002068420 A1 | 9/2002 |
| WO | 2002083066 A2 | 10/2002 |
| WO | 2003015769 | 2/2003 |
| WO | 2003020737 A1 | 3/2003 |
| WO | 2003031458 A1 | 4/2003 |
| WO | 2003064411 | 8/2003 |
| WO | 2003078404 A1 | 9/2003 |
| WO | 2003099836 A1 | 12/2003 |
| WO | 2004007517 A1 | 1/2004 |
| WO | 2004013118 A1 | 2/2004 |
| WO | 2004018468 A2 | 3/2004 |
| WO | 2004052902 A1 | 6/2004 |
| WO | 2004052903 A1 | 6/2004 |
| WO | 2004063209 A2 | 7/2004 |
| WO | 2004076470 A2 | 9/2004 |
| WO | 2004080990 A1 | 9/2004 |
| WO | 2005011592 A2 | 2/2005 |
| WO | 2005011786 A1 | 2/2005 |
| WO | 2005012318 A2 | 2/2005 |
| WO | 2005012326 A1 | 2/2005 |
| WO | 2005021566 A2 | 3/2005 |
| WO | 2005049022 A2 | 6/2005 |
| WO | 2005063785 A2 | 7/2005 |
| WO | 2005067976 A2 | 7/2005 |
| WO | 2005085237 A1 | 9/2005 |
| WO | 2005085246 A1 | 9/2005 |
| WO | 2005085265 A1 | 9/2005 |
| WO | 2005092877 A1 | 10/2005 |
| WO | 2005117861 A1 | 12/2005 |
| WO | 2006002912 A1 | 1/2006 |
| WO | 2006006496 A1 | 1/2006 |
| WO | 2006008038 A1 | 1/2006 |
| WO | 2006010557 A1 | 2/2006 |
| WO | 2006011469 A1 | 2/2006 |
| WO | 2006018150 A1 | 2/2006 |
| WO | 2006034489 A2 | 3/2006 |
| WO | 2006037537 A2 | 4/2006 |
| WO | 2006048427 A1 | 5/2006 |
| WO | 2006064033 A2 | 6/2006 |
| WO | 2006078593 A2 | 7/2006 |
| WO | 2006089872 A1 | 8/2006 |
| WO | 2006108842 A1 | 10/2006 |
| WO | 2006117359 A1 | 11/2006 |
| WO | 2006117360 A1 | 11/2006 |
| WO | 2006120208 A1 | 11/2006 |
| WO | 2007000445 A1 | 1/2007 |
| WO | 2007014894 A2 | 2/2007 |
| WO | 2007025943 A2 | 3/2007 |
| WO | 2007028814 A1 | 3/2007 |
| WO | 2007031548 A2 | 3/2007 |
| WO | 2007033350 A1 | 3/2007 |
| WO | 2007039417 A1 | 4/2007 |
| WO | 2007041053 A2 | 4/2007 |
| WO | 2007093610 A1 | 8/2007 |
| WO | 2007128724 A1 | 11/2007 |
| WO | 2007128749 A1 | 11/2007 |
| WO | 2007128761 A2 | 11/2007 |
| WO | 2007136116 A2 | 11/2007 |
| WO | 2007144175 A2 | 12/2007 |
| WO | 2008002905 A2 | 1/2008 |
| WO | 2008020011 A1 | 2/2008 |
| WO | 2008022267 A2 | 2/2008 |
| WO | 2008034859 A1 | 3/2008 |
| WO | 2008049923 A1 | 5/2008 |
| WO | 2008055870 A1 | 5/2008 |
| WO | 2008055940 A2 | 5/2008 |
| WO | 2008062273 A2 | 5/2008 |
| WO | 2008089892 A1 | 7/2008 |
| WO | 2008090210 A1 | 7/2008 |
| WO | 2008101938 A1 | 8/2008 |
| WO | 2008101939 A1 | 8/2008 |
| WO | 2008101943 A1 | 8/2008 |
| WO | 2008116179 A1 | 9/2008 |
| WO | 2008116195 A2 | 9/2008 |
| WO | 2008131149 A2 | 10/2008 |
| WO | 2009022007 A1 | 2/2009 |
| WO | 2009022010 A1 | 2/2009 |
| WO | 2009035969 A1 | 3/2009 |
| WO | 2009091082 A1 | 7/2009 |
| WO | 2009099734 A1 | 8/2009 |
| WO | 2009121945 A2 | 10/2009 |
| WO | 2009123194 A1 | 10/2009 |
| WO | 2010045656 A2 | 4/2010 |
| WO | 2010049678 A2 | 5/2010 |
| WO | 2010072776 A1 | 7/2010 |
| WO | 2010092123 A1 | 8/2010 |
| WO | 2010092124 A1 | 8/2010 |
| WO | 2010092125 A1 | 8/2010 |
| WO | 2010092126 A1 | 8/2010 |
| WO | 2010119990 A1 | 10/2010 |
| WO | 2010138535 A1 | 12/2010 |
| WO | 2011039107 A1 | 4/2011 |
| WO | 2011039108 A2 | 4/2011 |
| WO | 2011039337 A1 | 4/2011 |
| WO | 2011060290 A2 | 5/2011 |
| WO | 2011120923 A1 | 10/2011 |
| WO | 2012031124 A2 | 3/2012 |
| WO | 2012062698 A1 | 5/2012 |
| WO | 2012065993 A1 | 5/2012 |
| WO | 2012106303 A1 | 8/2012 |
| WO | 2012107476 A1 | 8/2012 |

(56) References Cited

FOREIGN PATENT DOCUMENTS

| | | |
|---|---|---|
| WO | 2012120040 A1 | 9/2012 |
| WO | 2012163990 A1 | 12/2012 |
| WO | 2013007557 A1 | 1/2013 |
| WO | 2013131967 A1 | 9/2013 |
| WO | 2013139777 A1 | 9/2013 |
| WO | 2014011926 A1 | 1/2014 |
| WO | 2014161918 A1 | 10/2014 |
| WO | 2014170383 A1 | 10/2014 |
| WO | 2016046150 A1 | 3/2016 |

OTHER PUBLICATIONS

Hasnain, Mehrul et al. "Metformin for Atypical Antipsychotic-Induced Weight Gain and Glucose Metabolism Dysregulation—Review of Literature and Clinical Suggestions" (2010) CNS Drugs, 24(3), pp. 194-206.
Hatsuda, Asanorl, et al; A Practical Synthesis of Highly Functionalized Aryl Nitriles Through Cyanation of Aryl Bromides Employing Heterogeneous Pd/C; Tetrahedron Letters (2005) vol. 46 pp. 1849-1853; Elsevier Ltd.
Heise, Tim et al. "Treatment with BI 1356, a Novel and Potent DPP-IV Inhibitor Significantly Reduces Glucose Excursions after an oGTT in Patients with Type 2 Diabetes" (2007) Diabetes, Supp 1, vol. 56, 4 pgs.
Henderson, David C. et al. "Clozapine and Hypertension: A Chart Review of 82 Patients" (2004) J Clin Psychiatry, 65, pp. 686-689.
Holst, Jens Juul et al. "Role of Incretin Hormones in the Regulaion of Insulin Secretion in Diabetic and Nondiabetic Humans" (2004) Am. J Physiol Endocrinol Metab, 287: E199-E206.
Hussey, Elizabeth K. et al. "Safety, Pharmacokinetics and Pharmacodynamics of Remogliflozin Etabonate (SGLT2 Inhibitor) and Metformin When Co-Administered in Type 2 Diabetes Mellitus (T2DM) Patients" Diabetes, American Diabetes Association, (2009) XP00913667, vol. 58, p. A157.
Idris, Iskandar et al "Sodium-glucose co-transporter-2 inhibitors: an emerging new class of oral antidiabetic drug" (2009) Diabetes, Obesity and Metabolism, 11, 79-88.
International Search Report and Written Opinion for PCT/EP2012/062922 dated Aug. 14, 2012.
International Search Report for PCT/EP2011/054734 dated Aug. 12, 2011.
International Search Report for PCT/EP2011/069532 dated Dec. 15, 2011.
International Search Report for PCT/EP2012/052108 dated Mar. 8, 2012.
International Search Report for PCT/EP2012/060194 dated Jul. 17, 2012.
International Search Report for PCT/EP2013/055671 dated Apr. 16, 2013.
International Search Report for PCT/EP2014/056655 filed Apr. 3, 2014.
International Search Report for PCT/EP2014/057754 filed Apr. 16, 2014.
International Search Report for PCT/EP2014/057754 dated May 27, 2014.
International Search Report for PCT/EP2016/074601 dated Dec. 16, 2016.
Isaji, Masayuki "Sodium-glucose cotransporter inhibitors for diabetes" Current Opinion in Investigational Drugs, (2007) vol. 8, No. 4, pp. 285-292.
Jabbour, S.A. et al. "Sodium glucose co-transporter 2 inhibitors: blocking renal tubular reabsorption of glucose to improve glycaemic control in patients with diabetes" (2008) Int J Clin Pract, 62, 8, 1279-1284.
Jabbour, Serge A. "The Importance of Reducing Hyperglycemia While Preserving Insulin Secretion—The Rational for Sodium-coupled Glucose Co-trnasporter 2 Inhibition in Diabetes" Touch Briefings, US Endocrinology (2009) pp. 75-78.
Jagdmann Jr, G. Erik ; Synthesis of 5-(4-Substituted Benzyl)-2,4-Diaminoquinazolines as Inhibitors of Candida albicans Dihydrofolate Reductase; Journal Heterocyclic Chemical (1995) vol. 32 pp. 1461-1465.
Jones, Byrony "Empagliflozin—one step closer to glycaemic control in patients with type II diabetes and CKD?" (2014) Nature Reviews Nephrology 10, 181, 2 pgs.
Joshi, Shashank R. "Metformin: Old Wine in New Bottle—Evolving Technology and Therapy in Diabetes" Journal of Association of Physicians in India, (2005) vol. 53, pp. 963-972.
Kadowaki, T et al. "PPAR gamma agonist and antagonist" Nihon Yakurigaku Zasshi (2001) vol. 118, No. 9, pp. 321-326. (English abstract).
Kashihara, Naoki et al. "Renin-Angiotensin System" (2011) Angiotensin Research, vol. 8, No. 2, pp. 40(96)-46(102).
Katsuno, Kenji et al. "Sergliflozin, a Novel Selective Inhibitor of Low-Affinity Sodium Glucose Cotransporter (SGLT2) Validates the Critical Role of SGLT2 in Renal Glucose Reabsorption and Modulates Plasma Glucose Level" the Journal of Pharmacology and Experimental Therapeutics (2007) vol. 320, No. 1, pp. 323-330.
Kautz, S. et al. "Early insulin therapy prevents beta cell loss in a mouse model for permanent neonatal diabetes (Munich Ins2C95s)" Diabetologia (2012) vol. 55, pp. 382-391.
Kojima, Naoki et al. "Effects of a New SGLT2 Inhibitor, Luseogliflozin on Diabetic Nephropathy in T2DN Rats" the Journal of Pharmacology and Experimental Therapeutics, (2013) V 345, pp. 464-472.
Lancet "Getting to the heart of the matter in type 2 diabetes" Editorial, (2015) 1 pg.
Lebovitz, Harold E. "Insulin secretagogues: old and new" (1999) Diabetes Review, vol. 7, 139-153.
Levetan, Claresa "Oral antidiabetic agents in type 2 diabetes" (2007) Current Medical Research and Opinion, vol. 23, No. 4, 945-952.
Lewin, Andrew et al "Initial Combination of Empagliflozin and Linagliptin in Subjects with Type 2 Diabetes" (2015) Diabetes Care, vol. 38, 394-402.
Li, T, et al. "Lack of Pharmacokinetic Interaction between Dapagliflozin and Pioglitazone in Healthy Subjects" Journal of Clinical Pharmacology, (2009) vol. 49, No. 9, pp. 1093.
Li, Yazhou, et al. "Glucagon-like Peptide-1 Receptor Signaling Modulates b Cell Apoptosis" (2003) The Journal of Biological Chemistry, vol. 278, No. 1, 471-478.
Lieberman, Herbert A. et al. "Pharmaceutical Dosage Forms: Tablets, vol. 1" (1989) pp. 5-6.
Lieberman, Joseph A. "Metabolic Changes Associated with Antipsychotic Use" Prim Care Companion J Clinc Psychiatry (2004) 6, pp. 8-13.
Lipworth, Brian J. "Clinical pharmacology of b3-adrenoceptors" Br J Clin Pharmacol (1996) pp. 291-300.
Maayan, Lawrence et al. "Effectiveness of Medications Used to Attenuate Antipsychotic-Related Weight Gain and Metabolic Antipsychotic-Related Weight Gain and Metabolic Abnormalities: A Systematic Review and Meta-Analysis" (2010) Neuropsychopharmacology, vol. 35, pp. 1520-1530.
Maeda, Yasutaka et al. "Oxidative Stress" (2010) Nippon Rinsho, vol. 68, No. 5, 814-818.
Magee, G.M. et al. "Is hyperfiltration associated with the future risk of developing diabetic nephropathy? A meta-analysis" Diabetologia (2009) 52: pp. 691-697.
Malatiali, Slava et al. "Phlorizin Prevents Glomerular Hyperfiltration but not Hypertrophy in Diabetic Rats" (2008) Experimental Diabetes Research, vol. 2008, 7 pgs.
Marchetti, Piero et al. "Pancreatic Islets from Type 2 Diabetic Patients Have Functional Defects and Increased Apoptosis that are Ameliorated by Metformin" the Journal of Clinical Endocrinology & Metabolism, (2004) vol. 89,(11) pp. 5535-5541.
Matsuyama, Tatsuo et al. "Glucagon-like peptide-1 (7-36 amide): a potent glucagonostatic and insulinotropic hormone" Diabetes Research and Clincial Practice (1988) 5, 281-284.
McMaster University, Chem2006 Lab Manual, 1997/98, Expt 1, Part B, pp. 1-9.

(56) References Cited

OTHER PUBLICATIONS

Meng, Wei et al "Discovery of Dapagliflozin: A Potent, Selective Renal Sodium-Dependent Glucose Cotransporter 2 (SGLT2) Inhibitor for the Treatment of Type 2 Diabetes" J. Med. Chem. (2008) vol. 51, pp. 1145-1149.
Merck Manual Online Edition, "Diabetes Mellitus" http://www.merckmanuals.com/professional/endocrine_and_metabolic_disorders/diabetes_mellitus_and_disorders of carbohyrate_metabolism/diabetes_mellitus_dm.html#v987998. last revision Jun. 2008 by Preeti Kishore M.D.
Merriam-Webster's Collegiate Dictionary,definition of prevent, published 1998 by Merriam-Webster Inc. p. 924.
Miller, Del D. "Review and Management of Clozapine Side Effects" (2000) J Clinc Psychiatry, 61 (Suppl 8) pp. 14-17.
Miyagawa, Junichiro et al. "Combined use between incretin-related meidcations and other medications" (2010) Diagnosis and Treatment, vol. 98, No. 3, 423-436.
Abstract ASN09L1_307a "Contact View (TH-P0751) Kidney Function and Response to Diabetes in Mice Lacking SGLT2", Vallon, Volker et al, Oct. 29, 2009, 1 pg.
Abstract ASN09L1_4153a, "Contact View (SA-P02723) Chronic SGLT2 Blockade Reduces Proximal Reabsorption and Normalizes State of Tubuloglomerular Feedback Activation in Hyperffitering Diabetic Rats" Thomson, Scott et al., Oct. 31, 2009, 1 pg.
Adachi, Tetsuya., et al; T-1095, A Renal Na+-Glucose Transporter Inhibitor, Improves Hyperglycemia in Streptozotocin-Induced Diabetic Rats; Metabolism (2000) vol. 49 No. 8 pp. 990-995.
Aires, Ines et al. "B1-10773, a sodium-glucose cotransporter 2 inhibitor for the potential oral treatment of type 2 diabetes mellitus" (2010) Current Opinion in Investigational Drugs, vol. 11 (10), pp. 1182-1190.
American Diabetes Association "Consensus Development Conference on Antipyschotic Drugs and Obesity and Diabetes" (2004) Diabetes Care, vol. 27, No. 2, pp. 596-601.
American Diabetes Association "Diagnosis and Classification of Diabetes Mellitus" Diabetes Care, vol. 33, Supplement 1, Jan. 2010. pp. S62-S69.
Anonymous, "Composition with a High Drug Load of Empagliflozin" Feb. 26, 2016, 3 pgs.
Ashiya, Mona et al. "Non-insulin therapies for type 2 diabetes" (2007) Nature Reviews, Drug Discovery vol. 6, 777-778.
Aulton, Michael E. "Pharmaceutics, the Science of Dosage Form Design" (2002) 2nd Edition, 404-409.
Bailey, Clifford J. "Renal Glucose Reabsorption Inhibitors to Treat Diabetes" (2011) Trends in Pharmacological Sciences, vol. 32, No. 2, 63-71.
Banker, Gilbert S. et al. "Modern Pharmaceutics, Third Edition, Revised and Expanded" (1996) Marcel Dekker, p. 596.
Baptista, Trino et al. "Pharmacological Management of Atypical Antipsychotic-Induced Weight Gain" (2008) CNS Drugs, 22, 6, pp. 478-495.
Bauer, Kurt H. et al. "Pharmazeutische Technologie" (1993) p. 293.
Bloomgarden, Zachary T. "Diabetes Treatment" Diabetes Care, (Mar. 2009) vol. 32, No. 3 pp. e25-e30.
Boyda, Heidi N. et al. "Preclinical models of antipsychotic drug-induced metabolic side effects" (2010) Trends in Pharmacological Sciences vol. 31, pp. 484-497.
Byrn, Stephen et al. "Pharmaceutical Solids: A Strategic Approach to Regulatory Considerations" Pharmaceutical Research, vol. 12, No. 7, (1995) pp. 945-954.
Campbell, R. Keith "Rationale for Dipeptidyl Peptidase 4 Inhibitors: A New Class of Oral Agents for the Treatment of Type 2 Diabetes Mellitus" (2007) The Annals of Pharmacotherapy, vol. 41, 51-60.
Cernea Simona. et al. "ß-Cell Protection and Therapy for Latent Autoimmune Diabetes in Adults" Diabetes Care (2009) vol. 32, Supplement 2, pp. S246-S252.
Cetrone, Michela et al. "Effects of the antidiabetic drugs on the age-related atrophy and sarcopenia associated with diabetes type II" Current Diabetes Reviews (2014) vol. 10, No. 4, pp. 231-237.

Chen, L. H. et al. "Inhibition of the sodium glucose co-transporter-2: its beneficial action and potential combination therapy for type 2 diabetes mellitus" Diabetes, Obesity and Metabolism, (2013) vol. 15, pp. 392-402.
Chow, Francis CC, et al. "Challenges in achieving optimal glycemic control in type 2 diabetes patients with declining renal function: The Southeast Asia perspective" Journal of Diabetes Investigation, (2012) vol. 3, Issue 6, pp. 481-489.
Chyan, Yau-Jan, et al. "Dipeptidyl Peptidase-IV Inhibitors: An Evolving Treatment for Tyep 2 Diabetes from the Incretin Concept" (2007) Recent Patents on Endocrine, Metabolic & Immune Drug Discovery, vol. 1, No. 1, 15-24.
Clinical Trials: NCT01011868 "Efficacy and Safety of BI 10773 in Combination with Insulin in Patients with Type 2 Diabetes" Sponsor Boehringer Ingelheim Pharmaceuticals, Oct. 18, 2010, 3 pgs.
Clinical Trials: NCT01131676. "BI 10773 Cardiovascular Outcome Event Trail in Type 2 Diabetes Mellitus Patients" Sponsor: Boehringer Ingelheim Pharmaceuticals, Updated date: Mar. 7, 2012. 5 pgs.
Clinical Trials: NCT01131676. "BI 10773 Cardiovascular Outcome Event Trail in Type 2 Diabetes Mellitus Patients" Sponsor: Boehringer Ingelheim Pharmaceuticals, Updated date: May 26, 2010. 4 pgs.
Clinical Trials: NCT01131676. "BI 10773 Cardiovascular Outcome Event Trail in Type 2 Diabetes Mellitus Patients" Sponsor: Boehringer Ingelheim Pharmaceuticals, Updated date: Nov. 14, 2012. 4 pgs.
Clinical Trials: NCT01167881. "Efficacy and Safety of Empagliflozin (BI 10773) With Metformin in Patients with Type 2 Diabetes" Sponsor Boehringer Ingelheim Pharmaceuticals, Updated Date: Apr. 3, 2013, 4 pgs.
Deacon, Carolyn F. "Perspectives in Diabetes Therapeutic Strategies Based on Glucagon-Like Peptide 1" Diabetes, (2004) vol. 53 pp. 2181-2189.
Defronzo, Ralph A. et al. "Combination of Empagliflozin and Linagliptin as Second-Line Therapy in Subjects with Type 2 Diabetes Inadequately Controlled on Metformin" (2015) Diabetes Care, 38, 384-393.
Diabetes Mellitus, Merck Manual Online Edition, (retrieved Sep. 13, 2011) http://www.merckmanuals.com/professional/endocrine_and_metabolic_disorders/diabetes_mellitus_and_disorders_of_carbohydrate_metabolism/diabetes_mellitus_dm.html#v987998. Revision Jun. 2008.
Drucker, Daniel J. et al. "Glucagon-like peptide I stimulates insulin gene expression and increases cyclic AMP levels in a rat islet cell line" (1987) Proc. Natl. Acad. Sci. USA, vol. 84, 3434-3438.
Drug Watch "Type 2 Diabetes Mellitus" Formulary vol. 43 Aug. 2008 p. 304.
Drugbank. Metformin. Accession No. DB00331 (APRD01099) https://www.drugbank.ca/drugs/DB00331. Drug created on Jun. 13, 2005/Updated on May 9, 2017.
Ellinger, Lara K. et al. "Efficacy of Metformin and Topiramate in Prevention and Treatment of Second-Generation Antipsychotic-Induced Weight Gain" Annals of Pharmacotherapy (2010) vol. 44, No. 4, pp. 668-679.
EMBASE Database. Accession No. 0050872772. Jelsing, J et al. "Empagliflozin a novel sodium glucose cotransporter-2 inhibitor improves glucose homeostasis and preserves pancreatic beta cell mass in db/db mice" (2012) 2 pgs.
EMBASE database: Accession No. 0050781595. Jelsing, Jacob et al. "The sodium glucose cotransporter-2 (SGLT-2) inhibitor empagliflozin has a durable effect on the restoration of glucose homeostasis by preserving beta-cell mass in zucker diabetic fatty rats" (2012) 2 pgs.
Ettmayer, Peter et al. "Lessons Learned from Marketed and Investigational Prodrugs" (2004) Journal of Medicinal Chemistry, vol. 47, No. 10, pp. 2393-2404.
Ferrannini, Ele et al. "CV Protection in the EMPA-REG Outcome Trial: A "Thrifty Substrate" Hypothesis" Diabetes Care, Jun. 11, 2016, pp. 1-7.
Fiese, Eugene F et al. "Preformulation" (1987) The Theory and Practice of Industrial Pharmacy, 28 pgs.
Fitchett, David et al. "Heart failure outcomes with empagliflozin in patients with type 2 diabetes at high cardiovascular risk: results of the EMPA-REG Outcome® trial" (2016) European Heart Journal vol. 37, pp. 1526-1534.

(56) References Cited

OTHER PUBLICATIONS

Foote, Celine et al. "Effects of SGLT2 inhibitors on cardiovascular outcomes" (2012) Diabetes & Vascular Disease Research, vol. 9, (2) pp. 117-123.
Fujii, Masakazu et al. "Oxidative Stress and Diabetic Vascular Diseases" (2009) Angiology Frontier, vol. 8, No. 1, pp. 47-54.
Fujimori, Yoshikazu et al. "Remogliflozin Etabonate in a Novel Category of Selective Low-Affinity Sodium Glucose Cotransporter (SGLT2) Inhibitors, Exhibits Antidiabetic Efficacy in Rodent Models" (2008) Journal of Pharmacology and Experimental Therapeutics vol. 327 No. 1, pp. 268-276.
Garber, A.J. et al. "Vildagliptin in combination with pioglitazone improves glycaemic control in patients with type 2 diabetes failing thiazolidinedione monotherapy: a randomized, placebo-controlled study" (2007) Diabetes, Obesity and Metabolism, 9, 166-174.
Gennaro, Alfonso R. "Remington: The Science and Practice of Pharmacy" Twentieth Edition (2000) 4 pgs.
Golay A. et al. "Link Between Obesity and Type 2 Diabetes" (2005) Best Practice & Research Clinical Endocrinology & Metabolism, vol. 19, No. 4, 649-663.
Goodwin, Nicole C. et al. "Novel L-Xylose Derivatives as Selective Sodium-Dependent Glucose Cotransporter 2 (SGLT2) Inhibitors for the Treatment of Type 2 Diabetes" (2009) Journal Medicinal Chemistry vol. 52 pp. 6201-6204.
Graefe-Mody, E.U., et al., "Evaluation of the potential for steady-state pharmacokinectic and pharmacodynamic interactions between the DPP-4 inhibitor linagliptin and metformin in healthy subjects". Current Medical Research and Opinion, Informa Healthcare, GB, vol. 25. No. 8, Aug. 1, 2009, pp. 1963-1972.
Greco, Gary T. et al. "Segregation of Active Constituents from Tablet Formulations During Grinding: Theoretical Considerations" Drug Development and Industrial Pharmacy, (1982) 8(4), pp. 565-578.
Gupta, Rajesh et al. "Emerging Drug Candidates of Dipeptidyl Peptidase IV (DPP IV) Inhibitor Class for the Treatment of Type 2 Diabetes" (2009) Current Drug Targets, vol. 10, No. 1, 71-87.
Anonymous "Efficacy and Safety of Empagliflozin (BI 10773) in Patients with Type 2 Diabetes and Renal Impairment" Jan. 8, 2013, XP055120166, www.clinicaltrials.gov/ct2/show/study/NCT01164501?term=empagliflozin&rank=26.
Anonymous "Prevalence of Chronic Kidney Disease and Associated Risk Factors—United States, 1999-2004", Mar. 2, 2007, XP055119515, http://www.cdc.gov/mmwr/preview/mmwrhtml/mm5608a2.htm.
Barnett, Anthony H. et al. "Efficacy and safety of empagliflozin added to existing antidiabetes treatments in patients with type 2 diabetes and chronic kidney disease: a randomised, double-blind, placebo-controlled trial" the Lancet, (2014) vol. 2, pp. 369-384.
Baron, Kyle T. et al. "Population Pharmacokinetics and Exposure-Response (Efficacy and Safety/Tolerability) of Empagliflozin in Patients with Type 2 Diabetes" (2016) Diabetes Ther, 7: 455-471.
Cherney, David et al. "The effect of sodium glucose cotransporter 2 inhibition with empagliflozin on microalbuminuria and macroalbuminuria in patients with type 2 diabetes" (2016) Diabetologia, 11pgs.
Cherney, David Z.I. et al. "Pooled analysis of Phase III trials indicate contrasting influences of renal function on blood pressure, body weight, and HbA1c reductions with empagliflozin" (2017) Kidney International, 1-14.
Cherney, David Z.I. et al. "Renal Hemodynamic Effect of Sodium-Glucose Cotransporter 2 Inhibition in Patients with Type 1 Diabetes Mellitus" Circulation, (2014) V 129, pp. 587-597.
Clinical Trials: NCT01164501 "Efficacy and Safety of BI 10773 in Patients with Type 2 Diabetes and Renal Impairment" Sponsor: Boehringer Ingelheim Pharmaceuticals, Jul. 15, 2010, 4 pgs.
Clinical Trials: NCT01164501 "Efficacy and Safety of BI 10773 in Patients with Type 2 Diabetes and Renal Impairment" Sponsor: Boehringer Ingelheim Pharmaceuticals, Mar. 7, 2012, 3 pgs.
European Patent Application 14715578.2, EP2981271; "Third party observations pursuant to article 115 EPC" (2017) 28 pgs.
Farxiga, Prescribing Information, Reference ID 3433133, Manufactured by Bristol-Myers Squibb Company, published by the FDA on Jan. 8, 2014, 43 pgs.
Ferrannini, E. et al. "A Phase IIb, randomized, placebo-controlled study of the SGLT2 inhibitor empagliflozin in patients with type 2 diabetes" (2013) Diabetes, Obesity and Metabolism, 15: 721-728.
Ferrannini, Ele et al. "Renal Glucose Handling: Impact of Chronic Kidney Disease (CKD) and SGLT2 Inhibition in Patients with Type 2 Diabetes" (2012) Clinical Diabetes/Therapeutics Posters, 1028-P, A264.
Grempler, R et al. "Empagliflozin, a novel selective sodium glucose cotransporter-2 (SGLT-2) inhibitor: characterisation and comparsion with other SGLT-2 inhibitors" Diabetes, Obesity and Metabolism, (2012) vol. 14, pp. 33-90.
International Search Report for PCT/EP2014/056657 filed Apr. 3, 2014.
Invokana, Prescribing Information, Manufactured by Janssen Ortho LLC., published by the FDA on Mar. 29, 2013, 41 pgs.
Kasichayanula, Sreeneeranj et al. "The Influence of Kidney Function on Dapagliflozin Exposure, Metabolism and Pharmacodynamics in Healthy Subjects and in Patients with Type 2 Diabetes Mellitus" (2012) British Journal of Clinical Pharmacology, vol. 76, Issue 3, pp. 432-444.
Kohan, Donald E. et al. "Abstract: [TH-P0524] Efficacy and Safety of Dapagliflozin in Patients with Type 2 Diabetes and Moderate Renal Impairment" Nov. 10, 2011, Abstract Sessions, 1 pg, http://www.abstracts2view.com.
Kohan, Donald E. et al. "Long-term study of patients with type 2 diabetes and moderate renal impairment shows that dapagliflozin reduces weight and blood pressure but does not improve glycemic control" (2013) Kidney International; 85, 962-971.
Macha, S. et al. "Pharmacokinetics, pharmacodynamics and safety of empagliflozin, a sodium glucose cotransporter 2 (SGLT2) inhibitor, in subjects with renal impairment" (2014) Diabetes, Obesity and Metabolism, 16: 215-222.
Panchapakesan, Usha et al. Effects of SGLT2 Inhibition in Human Kidney Proximal Tubular Cells—Renoprotection in Diabetic Nephropathy? PLOS one, (2013) vol. 8, Issue 2, e54442, 8 pgs.
Rosenstock, J. et al. "Efficacy and safety of empagliflozin, a sodium glucose cotransporter (SGLT2) inhibitor, as add-on to metformin in type 2 diabetes with mild hyperglycaemia" (2013) Diabetes, Obesity and Metabolism, 15: 1154-1160.
Rosenstock, J. et al. "Impact of empagliflozin added on to basal insulin in type 2 diabetes inadequately controlled on basal insulin: a 78-week randomized, double-blind, placebo-controlled trial" (2015) Diabetes, Obesity and Metabolism, 17: 936-948.
Skrtic, Marko et al. "Characterisation of glomerular haemodynamic responses to SGLT2 inhibition in patients with type 1 diabetes and renal hyperfiltration" (2014) Diabetolgia, 4 pgs.
Suzuki, Masayuki et al. "Tofogliflozin, a Potent and Nightly Specific Sodium/Glucose Cotransporter 2 Inhibitor, Improves Glycemic Control in Diabetic Rats and Mice" the Journal of Pharmacology and Experimental Therapeuticals, vol. 341, No. 3 pp. 692-701.
Thomson, Scott C. et al. "Acute and chronic effects of SGLT2 blockade on glomerular and tubular function in the early diabetic rat" (2012) Am J Physiol Regul Integr Comp Physiol, 302, R75-R83.
Vallon, Volker et al. "Glomerular Hyperfiltration in Experimental Diabetes Melliutes: Potential Role of Tubular Reabsorption" (1999) J. Am. Soc. Nephrol., V 10: pp. 2569-2576.
Vallon, Volker et al. "SGLT2 inhibitor empagliflozin reduces renal growth and albuminuria in proportion to hyperglycemia and prevents glomerular hyperfiltration in diabetic Akita mice" (2013) Am J Physiol Renal Physiol, 306, F194-F204.
Veltkamp, Stephan A. et al. "[1127-P] The Effect of Renal Impairment on the Pharmacokinetics and Urinary Glucose Excretion of the SGLT2 Inhibitor ASP1941 in Type 2 Diabetes Mellitus Patients" Clinical Therapeutics/New Technology, A309-A310.
Wanner, Christoph et al. "Empagliflozin and Clinical Outcomes in Patients with Type 2 Diabetes, Established Cardiovascular and Chronic Kidney Disease" (2017) Circulation, American Heart Association, 66 pgs.

(56) References Cited

OTHER PUBLICATIONS

Wanner, Christoph et al. "Empagliflozin and Progression of Kidney Disease in Type 2 Diabetes" (2016) The New England Journal of Medicine, 1-12.
Yale, J.F. et al. "Efficacy and safety of canagliflozin in subjects with type 2 diabetes and chronic kidney disease" Diabetes, Obesity and Metabolism (2013) vol. 15, pp. 463-473.
Yale, Jean-Francois et al. "Canagliflozin, a Sodium Glucose Co-Transporter 2 Inhibitor, Improves Glycemia and is Well Tolerated in Type 2 Diabetes Mellitus Subjects with Moderate Renal Impairment" Jun. 8, 2012, Poster presented at the 72nd Scientific Session of the American Diabetes Association, 2 pgs.
Yamout, Hala et al. "Efficacy and Safety of Canagliflozin in Patients with Type 2 Diabetes and Stage 3 Nephropathy" (2014) Am J Nephrol, 40: 64-74.
Exhibit submitted on Dec. 14, 2017 in parent U.S. Appl. No. 14/918,727.
Mogensen, Carl Erik "Perspectives in Diabetes Prediction of Clinical Diabetic Nephropathy in IDDM Patients Alternatives to Microalbuminuria?" Diabetes (1990) vol. 39, pp. 761-767.
Mojsov, Svetlana "Insulinotropin: Glucagon-like Peptide I (7-37) Co-encoded in the Glucagon Gene is a Potent Stimulator of Insulin Release in the Perfused Rat Pancreas" J. Clin. Invest. (1987) vol. 79, 616-619.
Mooradian, Arsharg D. et al. "Narrative Review: A Rational Approach to Starting Insulin Therapy" (2006) Annals of Internal Medicine, vol. 145, pp. 125-134.
Nair, S. et al. "From history to reality: sodium glucose co-transporter 2 inhibitors—a novel therapy for type 2 diabetes mellitus" (2010) Pract Diab Int, vol. 27, No. 7, pp. 311-316.
Nathan, D.M. et al. "Medical management of hyperglycaemia in type 2 diabetes mellitus: a consensus algorithm for the initiation and adjustment of therapy" Diabetologia (2009) 52, 17-30.
Neamati, Ouri., et al;, "Depsides and Depsidones as Inhibiton of HIV-1 Integrase: Dimvery of Novel Inhibitors Through 3D Database Searclung", J. Med. Chem., 1997, vol. 40, pp. 942-951.
Oku, Akira et al. "T-1095, an Inhibitor of Renal Na+ -Glucose Cotransporters, May Provide a Novel Approach to Treating Diabetes" (1999) Diabetes, vol. 48, 1794-1800.
Oku, Akira., et al; Jan. 1095, An Inhibitor or renal Na+ -Glucose Cotransporters, May Provide a Novel Approach to Treating Diabetes; Diabetes (1999) vol. 48 pp. 1794-1800.
Osorio, Horacio et al. "Sodium-Glucose Cotransporter Inhibition Prevents Oxidative Stress in the Kidney of Diabetic Rats" (2012) Oxidative Medicine and Cellular Longevity, vol. 2012, Article ID 542042, 7 pgs.
Patane, Giovanni et al. "Metformin Restores Insulin Secretion Altered by Chronic Exposure to Free Fatty Acids or High Glucose, a Direct Metformin Effect on Pancreatic b-Cells" (2000) Diabetes, vol. 49, pp. 735-740.
Patil, Basanagouda M. et al. "Elevation of systolic blood pressure in an animal model of olanzapine induced weight gain" (2006) European Journal of Pharmacology, vol. 551, pp. 112-115.
Perkins, Bruce A. et al. "Sodium-Glucose Cotransporter 2 Inhibition and Glycemic Control in Type 1 Diabetes: Results of an 8-Week Open-Label Proof-of-Concept Trial" (2014) Diabetes Care, vol. 37, pp. 1480-1483.
Pham, David et al. "Impact of empagliflozin in patients with diabetes and heart failure" (2017) Trends in Cardiovascular Medicine, vol. 27, pp. 144-151.
Piya, Milan K. et al. "Emerging treatment options for type 2 diabetes" British Journal of Clinical Pharmacology, (2010) vol. 70, No. 5, pp. 631-644.
Poole, Chris D. et al. "The prescription cost of managing people with type 1 and type 2 diabetes following initiation of treatment with either insulin glargine or insulin detemir in routine general practice in the UK: a retrospective database analysis" (2007) Current Medical Research and Opinion, vol. 23, S. 1, pp. 541-S48.

Powers, Richard E. et al. "Understanding the Side Effects of Neuroleptics" (2008) Bureau of Geriatric Psychiatry/DETA, pp. 17-24.
Pratley, Richard E. et al. "Inhibition of DPP-4: a new therapeutic approach for the treatment of type 2 diabetes" (2007) Current Medical Research and Opinion, vol. 23, No. 4, 919-931.
Printz, Richard L. et al. "Tweaking the Glucose Sensor: Adjusting Glucokinase Activity with Activator Compounds" Endocrinology, (2005) vol. 146, No. 9, pp. 3693-3695.
Profit, Louise et al. "Vildagliptin: the evidence for its place in the treatment of type 2 diabetes mellitus" (2008) Core Evidence, 3(1), 13-30.
Pschyrembel et al. Clinical Dictionary, 257th Edition, Diabetes Mellitus, (1993) 320-321.
Redenti, Enrico et al. "Drug/Cyclodextrin/Hydroxy Acid Multicomponent Systems. Properties and Pharmaceutical Applications" Journal of Pharmaceutical Sciences, (2000) vol. 89, No. 1, pp. 1-8.
Richardson, H. et al. "Effects of rosiglitazone and metformin on pancreatic beta cell and gene expression" (2006) Diabetologia V 49, pp. 685-696.
Rieusset, Jennifer et al. "Insulin Acutely Regulates the Expression of the Peroxisome Proliferator-Activated Receptor -y in Human Adipocytes" (1999) Diabetes, vol. 48, pp. 699-705.
Ritchie, C.W. et al. "The impact upon extra-pyramidal side effects, clinical symptoms and quality of life of a switch from conventional to atypical antipsychotics (risperidone or olanzapine) in elderly patients with schizophrenia" (2003) International Journal of Geriatric Psychiatry, vol. 18, pp. 432-440.
Rosenstock, J. et al. "Efficacy and safety of empagiiflozin, a sodium glucose cotransporter (SGLT2) inhibitor, as add-on to metformin in type 2 diabetes with mild hyperglycaemia" (2013) Diabetes, Obesity and Metabolism, 15: 1154-1160.
Rosenstock, Julio et al. "Improved Glucose Control with Weight Loss, Lower Insulin Doses, and No Increased Hypogiycemia with Empagliflozin Added to Titrated Multiple Daily Injections of Insulin in Obese Inadequately Controlled Type 2 Diabetes" (2014) Diabetes Care, vol. 37, pp. 1815-1823.
Rudnic, Edward et al. "Oral Solid Dosage Forms" Remington's Pharmaceutical Sciences, 18th Ed, Gennaro, A.R. Ed, Macie Pub. Co. (1990) pp. 1633-1665.
Schernthaner, G et al. "How attractive is the combination of a sodium glucose co-transporter 2 inhibitor with a dipeptidyl peptidase 4 inhibitor in the treatment of type 2 diabetes" (2015) Diabetes, Obesity and Metabolism, 17, 613-615.
Shannon, James A. et al. "The Excretion of Inulin, Xylose and Urea by Normal and Phlorizinized Man" New York University College of Medicine, Department of Physiology, Feb. 13, 1935, 393-401.
Sherwin, Robert S. et al. "The Prevention or Delay of Type 2 Diabetes" Diabetes Care, (2002) vol. 25, No. 4, pp. 742-749.
Shioi, Atsushi "Vascular Calcification and Remodeling in Diabetes" (2010) The Journal of Japanese College of Angiology, vol. 50, No. 5, 561-567.
Singhal, Dharmendra et al. "Drug polymorphism and dosage form design: a practical perspective" Advanced Drug Delivery Reviews, 56, (2004) pp. 335-347.
Softeland, Eirik et al. "Empagliflozin as Add-on Therapy in Patients with Type 2 Diabetes Inadequately Controlled With Linagliptin and Mefformin: A 24-Week Randomized, Double-Blind, Parallel-Group Trial" (2016) Diabetes Care, DOI:10.2337/dc16-1347, pp. 1-9.
Stella, Valentino J. "Prodrugs as therapeutics" (2004) Ashley Publications, vol. 14, No. 3, pp. 277-280.
Svegliati-Baroni, Gianluca et al. "Glucagon-like peptide-1 receptor activation stimulates hepatic lipid oxidation and restores hepatic signalling alteration induced by a high-fat diet in nonalcholic steatohepatitis" (2011) Liver International, vol. 31, 9, pp. 1285-1297.
Swarbrick et al., Encyclopedia of Pharmaceutical Technology, 2nd Edition, (2002) 4 pgs.
Tanaka, Chikako "Therapeutic Drugs for Metabolic Diseases, Chapter 2" (2002) New Yakurigaku (New Pharmacology) pp. 524-527.
Testa, Bernard "Prodrug research: futile or fertile?" (2004) Biochemical Pharmacology vol. 68, pp. 2097-2106.

(56) References Cited

OTHER PUBLICATIONS

Thomas, L., "Chronic treatment with the Dipeptidyl Peptidase-4 Inhibitor BI 1356[9R)-8-(3-Amino-piperidin-1-yl)-7-but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" the Journal of Pharmacology and Experimental Therapeutics, Feb. 2009, vol. 328, No. 2, 556-563.
Thomas, Leo et al. "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics (2008) 325, pp. 175-182.
Tsujihara, Kenji et al. "Na+ -Glucose Cotransporter (SGLT) Inhibitors as Antidiabetic Agents. 4. Synthesis and Pharmacological Properties of 4'-Dehydroxyphlorizin Derivatives Substituted on the B Ring" J. Med. Chem. (1999) vol. 42, pp. 5311-5324.
Ueta, Kiichiro., et al; Long-Term Treatment with the Na' -Glucose Cotransporter Inhibitor T-1095 Causes Sustained Improvement in Hyperglycemia and Prevents Diabetic Neuropathy in Goto-Kakizaki Rats; Life Sciences (2005) vol. 76 pp. 2655-2668.
United States Pharmacopoeia, the National Formulary, (2005) USP 28, NF 23, p. 2711.
Unknown "Intensification of Development of SGLT inhibitor—New Alternative of Antidiabetic" Aug. 21, 2007; 2 pgs; http://www.yakuji.co.jp/entry4100.html.
Valk, Harold W. de "DPP-4 Inhibitors and Combined Treatment in Type 2 Diabetes: Re-evaluation of Clinical Success and Safety" (2007) The Review of Diabetic Studies, vol. 4, No. 3, 126-133.
Vallon, Volker et al. "Knockout of Na-glucose transporter SGLT2 attenuates hyperglycemia and glomerular hypertiltration but not kidney growth or injury in diabetes mellitus" (2012) Am J Physiol Renal Physiol, vol. 304, F156-F167.
Vervoort, G. et al. "Glomerular hyperfiltration in type 1 diabetes mellitus results from primary changes in proximal tubular sodium handling without changes in volume expansion" (2005) European Journal of Clinical Investigation vol. 35, pp. 330-336.
Wang Y et al: "BI-1356. Dipeptidyl-peptidase IV inhibitor, antidiabetic agent" Drugs of the Future, Prous Science, ES,vol. 33, No. 6, Jun. 1, 2008, pp. 473-477.
Weber, Ann E. "Dipeptidyl Peptidase IV Inhibitors for the Treatment of Diabetes" (2004) J. Med. Chem., 47, 4135-4141.
Websters Third New International Dictionary, Editor: GOVE, definition of prevent; 1963, 2 pgs.
Wettergren, Andre et al. "Truncated GLP-1 (Proglucagon 78-107-Amide) Inhibits Gastric and Pancreatic Functions in Man" (1993) Digestive Diseases and Sciences, vol. 38, No. 4, 665-673.
Wolff, Manfred E., et al., "Burger's Medicinal Chemistry and Drug Discovery, Fifth Edition, vol. 1, Principles and Practices", (1995) Wiley-Interscience Publication pp. 975-977.
Woo, Young Sup et al. "Blood pressure changes during clozapine or olanzapine treatment in Korean schizophrenic patients" (2009) The World Journal of Biological Psychiatry, vol. 10(4); pp. 420-425.
Wu, Ren-Rong et al. "Lifestyle Intervention and Metformin for Treatment of Antipsychotic-Induced Weight Gain, a Randomized Controlled Trial" Journal of American Medical Association (2008) V 299, pp. 185-193.
Yamada, Yuichiro et al. "Clinic: Careful Progress in the Field and new Therapeutic Methods" Medical Online, (2007) vol. 220, No. 13, pp. 1219-1221.
Yao, Chun-Hsu et al. "Discovery of Novel N-b-D-Xylosylindole Derivatives as Sodium-Dependent Glucose Cotransporter 2 (SGLT2) Inhibitors for the Management of Hyperglycemia in Diabetes" (2011) J. Med. Chem. vol. 54, pp. 166-178.
Wang, L. et al "Dapagliflozin treatment in patients with different stages of type 2 diabetes mellitus: effects on glycaemic control and body weight" Diabetes, Obesity and Metabolism (2010) vol. 12, No. 6, p. 510-515.
Zhang, Wenbin et al. "EGT1442, a potent and selective SGLT2 inhibitor, attenuates blood glucose and HbA1c levels in db/db mice an prolongs the survival of stroke-prone rats" (2011) Pharmacological Research, vol. 63, pp. 284-293.
Zimmermann, Grant R et al. "Multi-target therapeutics: when the whole is greater than the sum of the parts" (2007) Drug Discovery Today, vol. 12, 34-42.
Zinman, Bernard et al. "Empagliflozin, Cardiovascular Outcomes and Mortality in Type 2 Diabetes" (2015) The New England Journal of Medicine, 373:22 pp. 2117-2128.
Zinman, Bernard et al. "Empagliflozin, Cardiovascular Outcomes, and Mortality in Type 2 Diabetes" (2015) The New England Journal of Medicine, vol. 373;22, pp. 2117-2128.
International Search Report for PCT/EP2017/078577 dated Feb. 1, 2018.
Heise, T. et al. "Safety, tolerability, pharmacokinetics and pharmacodynamics following 4 weeks' treatment with empagliflozin once daily in patients with type 2 diabetes" (2013) Diabetes, Obesity and Metabolism, 15: 613-621.
Stenlof, K. et al. "Efficacy and safety of canagliflozin monotherapy in subjects with type 2 diabetes mellitus inadequately controlled with diet and exercise" (2013) Diabetes, Obesity and Metabolism 15, 372-382.
Chen, Lu-Lu "1000 questions about endocrine metabolic disease" Hubei Changjiang Publishing Group, Aug. 2006, ISBN 7-5352-3595-6, 3 pages.
Du, Dong Hui "Challenges faced in primary care of diabetic patients with renal insufficiency" Diabetes World, Clinical Periodical, Nov. 2012, vol. 6, No. 11, 498-502.
Zhang, Wen Bin et al. "Renal SGLT2 inhibitors: A novel type of oral antidiabetic drug" (2010) Progress in Physiological Sciences, vol. 41, No. 6, 453-460.
Kuritzky, Louis "Addition of Basal Insulin to Oral Antidiabetic Agents: A Goal-Directed Approach to Type 2 Diabetes Therapy" (2006) MedGenMed. 8(4) 34, 19 pgs.
U.S. Appl. No. 15/918,477, filed Mar. 12, 2018. Inventor: Uli Christian Broedl.
U.S. Appl. No. 15/945,236, filed Apr. 4, 2018. Inventor: Uli Christian Broedl.
Yale, J.F. et al. "Efficacy and safety of canagliflozin in subjects with type 2 diabetes and chronic kidney disease" Diabetes, Obesity and Metabolism (Mar. 2013) vol. 15, 24 pgs, [online], [retrieved on Sep. 6, 2018]. Retrieved from the Internet <URL: <https://onlinelibrary.wiley.com/doi/full/10.1111/dom.12090>>.
Abdul-Ghani, Muhammad "Where does Combination Therapy with an SGLT2 Inhibitor Plus a DPP-4 Inhibitor Fit in the Management of Type 2 Diabetes?" (2015) Diabetes Care, 38, 373-375.
Abdul-Ghani, Muhammad A. et al. "Role of Sodium-Glucose Cotransporter 2 (SGLT 2) Inhibitors in the Treatment of Type 2 Diabetes" (2011) Endocrine Reviews, 32(4), 515-531.
Ahren, Bo "Dipeptidyl Peptidase-4 Inhibitors" (2007) Diabetes Care, vol. 30, No. 6, 1344-1350.
Ahren, Bo et al. "Twelve—and 52-Week Efficacy of the Dipeptidyl Peptidase IV Inhibitor LAF237 in Metformin-Treated Patients with Type 2 Diabetes" (2004) Diabetes Care, vol. 27, No. 12, 2874-2880.
Baati, Rachid et al. "A Convenient Synthesis of 2-Tetrahydrofuranyl Ethers" (2000) Organic Letters, vol. 2, No. 4, 185-487.
Baggio, Laurie L. et al. "Biology of Incretins: GLP-1 and GIP" Gastroenterology (2007) vol. 132, 2131-2157.
Brazg, R et al."Effect of Adding MK-0431 to Ongoing Metformin Therapy in Type 2" (2005) Diabetes, vol. 54, Suppl. 1, A3.
Bristol-Myers Squibb Company, Label "Glucophage (metformin hydrochloride) Tablets, Glucophage XR (metformin hydrochloride) Extended-Release Tablets" Apr. 2017, 35 pgs.
Caira, Mino R. "Crystalline Polymorphism of Organic Compounds" (1998) Topics in Current Chemistry, vol. 198, 164-208.
Clinical Trials: NCT00328172 "Efficacy and Safety of 3 Doses of BI1356 (Linagliptin) in Type 2 Diabetes Patients" Sponsor: Boehringer Ingelheim, Last Update Posted Mar. 14, 2014, 4 pgs.
Clinical Trials: NCT00554450 "Renal Impairment in Type 2 Diabetic Subjects" Sponsor: AstraZeneca, Last Update posted Oct. 17, 2016, 5 pgs.

(56) References Cited

OTHER PUBLICATIONS

Clinical Trials: NCT01064414 "An Efficacy, Safety and Tolerability Stude of Canagliflozin in Patients with Type 2 Diabetes Mellitus who have Moderate Renal Impairment" Sponsor: Janssen Research & Development LLC, Last Update Posted Aug. 14, 2013, 7 pgs.
Clinical Trials: NCT01164501 "Efficacy and Safety of BI 10773 in Patients with Type 2 Diabetes and Renal mpairment" Sponsor: Boehringer Ingelheim Pharmaceuticals, Last Update Posted: Jun. 16, 2014, 6 pgs.
Clinical Trials: NCT01210001 "Efficacy and Safety of Empagliflozin (BI 10773) in Type 2 Diabetes Patients on a 3ackground of Pioglitazone Alone or with Metformin" Sponsor: Boehringer Ingelheim, Last Update Posted Jun. 17, 2014, 7 pgs.
Crepaldi, G. et al. "Dipeptidyl peptidase 4 (DPP-4) inhibitors and their role in Type 2 diabetes management" (2007) J. Endocrinol. Invest., 30, 610-614.
European Medicines Agency, Science Medicines Health, "Assessment Report Forxiga dapagliflozin" (2012) 170 pgs.
Ferrannini, Ele et al. "SGLT2 inhibition in diabetes mellitus: rationale and clinical prospects" (2012) Nat. Rev. Endocrinol. vol. 8, 495-502.
Ghosh, Raktim Kumar et al. "SGLT2 Inhibitors: A New Emerging Therapeutic Class in the Treatment of Type 2 Diabetes Mellitus" (2012) Journal of Clinical Pharmacology, 52, 457-463.
Goldstein, Barry J. et al. "Effect of Initial Combination Therapy with Sitagliptin, a Dipeptidyl Peptidase-4 Inhibitor and Metformin on Glycemic Control in Patients with Type 2 Diabetes" (2007) Diabetes Care, vol. 30, No. 8, 1979-1987.
Guillory, J. Keith "Generation of Polymorphs, Hydrates, Solvates and Amorphous Solids" Polymorphism in Pharmaceutical Solids (1999) 46 pgs.
Handlon, Anthony L. "Sodium glucose co-transporter 2 (SGLT2) inhibitors as potential antidiabetic agents" (2005) Expert Opinion on Therapeutic Patents, 15:11, 1531-1540.
Hansch, C. "Search for New Drugs, Use of Quantitative Structure—Activity Relationships (QSAR) in Drug Design" (1980) Pomona College, Clermont, CA, Translated from Khimiko-Farmatsevticheskii Zhurnal, vol. 14, No. 10, 15-30.
Henry Ford Health System, "Chronic Kidney Disease, Clinical Practice Recommendations for Primary Care Physicians and Healthcare Providers, A Collaborative Approach", (Edition 6.0), 76 pgs.
Hummel, Charles S. et al. "Glucose transport by human renal Na+/D-glucose co-transporters" (2010) Am J Physiol Cell Physiol, 34 pgs.
Inzucchi, Silvo E. "Oral Antihyperglycemic Therapy for Type 2 Diabetes" (2002) JAMA, vol. 287, No. 3, 360-372.
Johnson & Johnson "FDA Advisory Committee Recommends Approval of Canagliflozin for Treatment of Adults with Type 2 Diabetes" (2013) Press Release, 3 pgs.
Larsen, Mogens Lytken et al. "Effect of Long-Term Monitoring of Glycosylated Hemoglobin Levels in Insulin-Dependent Diabetes Mellitus" (1990) The New England Journal of Medicine, vol. 323, No. 15, 1021-1025.
Levey, Andrew S. et al. "Definition and classification of chronic kidney disease: A position statement from Kidney Disease: Improving Global Outcomes (KDIGO)" (2005) Kidney International, vol. 67, 2089-2100.
Liu, Sheng et al. "Chemically induced (streptozotocin alloxan) diabetes mellitus in dogs" (2000) Bull Hunan Med University, vol. 25, No. 2, pp. 125-128 (English Translation).
Mckinney, James D. et al. "The Practice of Structure Activity Relationships (SAR) in Toxicology" (2000) Toxicological Sciences, vol. 56, 8-17.
Meyer, Timothy W. "Tubular injury in glomerular disease" (2003) Kidney International, vol. 63, pp. 774-787.
Munir, Kashif et al. "Differential pharmacology and clinical utility of empagliflozin in type 2 diabetes" (2016) Clinical 3harmacology: Advances and Applications, vol. 8, 19-34.
Murray, Michael "Encyclopedia of Nurtritional Supplements" (1996) pp. 283-287.

Nathan, David M. et al. "Management of Hyperglycemia in Type 2 Diabetes: A Consensus Algorithm for the Initiation and Adjustment of Therapy" (2006) Diabetes Care, vol. 29, No. 8, 1963-1972.
National Institute for Health Research, Horizon Scanning Centre, "Empagliflozin for type 2 diabetes mellitus" Apr. 2012, 10 pgs.
National Kidney Foundation, "Clinical Practice Guidelines, for Chronic Kidney Disease: Evaluation, Classification and Stratification" (2002) 356 pgs.
Nauck, Michael A. et al. "Cardiovascular Actions and Clincial Outcomes with Glucagon-Like Peptide-1 Receptor Agonists and Dipeptidyl Peptidase-4 Inhibitors" Circulation (2017) vol. 136, 849-870.
Pan, Qi et al. "Changes of streptomycin induced tyep I diabetes mellitus in serum oxygen free radicals and antioxidant function thereof in rats" (2006) Journal of China, Prescription Drug, vol. 56, pp. 65-66.
Plosker, Greg L. "Dapagliflozin: A Review of Its Use in Patients with Type 2 Diabetes" (2014) Drugs, 74, 2191-2209.
Riddle, Matthew C. "Oral Pharmacologic Management of Type 2 Diabetes" (1999) American Family Physician, 60(9), 2613-2620.
Robinson, J.A. "Chemical and Biochemical Aspects of Polyetherlonophore Antibiotic Biosynthesis" (1991) Progress in the Chemistry of Organic Natural Products, 1-81.
Scheen, Andre J. "Pharmacokinetic considerations for the treatment of diabetes in patients with chronic kidney lisease" (2013) Expert Opinion on Drug Metabolism and Toxicology, 9:5, 529-550.
Scottish Medicines Consortium, Product Assessment "dapagliflozin 5mg and 10mg (Forxiga)" Sep. 2012, 14 pgs.
Sturtevant Inc. "Micronizer Jet Mill" (2000), 6 pgs.
The American Association of Clinical Endocrinologists Medical Guidelines for the Management of Diabetes Mellitus: The AACE System of Intensive Diabetes Self-Management—2002 Update, (2002) Endocrine Practice, vol. 1, Supp 1, 43 pgs.
Thomas, Leo "Long-term treatment with empagliflozin, a novel, potent and selective SGLT-2 inhibitor, improves glycaemic control and features of metabolic syndrome in diabetic rats" (2012) Diabetes, Obesity and Metabolism, vol. 14, No. 1, 94-96.
Thomson, Scott C. et al. "Acute and chronic effects of SGLT2 blockade on glomerular and tubular function in the early diabetic rat" (2011) Am J Physiol Regul Integr Comp Physiol, V 302, pp. R75-R83.
Torrance, Christopher J. et al. "Combinatorial chemoprevention of intestinal neoplasia" (2000) Nature Medicine, Vo 5, No. 8, 1024-1028.
Twigger, Simon N. "Meeting Report of Rats and Men: The Rat Genome and Comparative Genomics" Genome Biology (2004) vol. 5, Issue 3, Article 314, 2 pgs.
U.S. Department of Health and Human Services, CDER, FDA, "Guideline for Submitting Supporting Documentation in Drug Applications for the Manufacture of Drug Substances" Feb. 1987, 48 pages.
U.S. Department of Health and Human Services, FDA, Endocrinologic and Metabolic Drugs Advisory Committee; Notice of Meeting, Federal Register, vol. 76, No. 80, Apr. 26, 2011, 23324-23325.
U.S. Department of Health and Human Services, FDA, "Guidance for Industry, Diabetes Mellitus—Evaluating Cardiovascular Risk in New Antidiabetic Therapies to Treat Type 2 Diabetes" Dec. 2008, 8 pages.
U.S. Department of Health and Human Services, FDA, "Guidance for Industry, Pharmacokinetics in Patients with Impaired Renal Function—Study Design, Data Analysis, and Impact on Dosing and Labeling" May 1998, 19 pages.
U.S. Department of Health and Human Services, FDA, Center for Drug Evaluation and Research "Application No. 2046290rig1s000 Summary Review (Jardiance) " 2014, 20 pages.
Valentine, Virginia "The Role of the Kidney and Sodium-Glucose Cotransporter-2 Inhibition in Diabetes Management" (2012) Clinical Diabetes, vol. 30, No. 4, 151-155.
Wielert-Badt, Susanne et al. "Probing the Conformation of the Sugar Transport Inhibitor Phlorizin by 2D-NMR, Molecular Dynamics Studies, and Pharmacophore Analysis" (2000) J. Med. Chem., vol. 43, 1692-1698.

(56) References Cited

OTHER PUBLICATIONS

Wielert-Badt, Susanne et al. "Single Molecule Recognition of Protein Binding Epitopes in Brush Border Membranes by Force Microscopy" (2002) Biophysical Journal, vol. 82, 2767-2774.

Woo, Vincent C. "Dapagliflozin: where does it fit in the treatment of type 2 diabetes" (2009) Expert Opinion on Pharmacotherapy, 10(15): 2527-2535.

Zheng, Tiesheng et al. "Clinical Biochemistry Experimental Diagnosis and Case Analysis" (2010) China Medical Science and Technology Press, 201001, p. 152.

* cited by examiner

FIG. 1A

| | Patients with mild renal impairment (eGFR ≥60 to <90 ml/min/1.73 m²) | | | Patients with moderate renal impairment (eGFR ≥30 to <60 ml/min/1.73 m²) | |
|---|---|---|---|---|---|
| | Placebo (n=95) | Empagliflozin 10 mg (n=98) | Empagliflozin 25 mg (n=97) | Placebo (n=187) | Empagliflozin 25 mg (n=187) |
| HbA₁c (%) | | | | | |
| Baseline† (SE) | 8.09 (0.08) | 8.02 (0.09) | 7.96 (0.07) | 8.04 (0.06) | 8.03 (0.06) |
| Change from baseline at week 24 (SE) | 0.06 (0.07) | -0.46 (0.07) | -0.63 (0.07) | 0.05 (0.05) | -0.37 (0.05) |
| Difference vs placebo (95% CI) | | -0.52 (-0.72,-0.32)*** | -0.68 (-0.88,-0.49)*** | | -0.42 (-0.56,-0.28)*** |
| Patients with HbA1c≥7.0% at baseline§ who reached HbA1c <7.0% at week 24, n (%) | 6 (6.7) | 16 (17.0) | 22 (24.2) | 14 (7.9) | 21 (12.0) |
| Odds ratio vs placebo | | 2.65 | 4.46** | | 1.82 |
| FPG (mg/dL) | | | | | |
| Baseline (SE) | 144.78 (3.90) | 145.96 (3.40) | 148.44 (3.47) | 143.78 (3.62) | 142.76 (2.67) |
| Change from baseline at week 24 (SE) | 5.67 (3.50) | -13.88 (3.44)*** | -18.08 (3.47)*** | 10.16 (2.80) | -9.26 (2.82)*** |

FIG. 1B

| | Patients with mild renal impairment (eGFR ≥60 to <90 ml/min/1.73 m²) | | | Patients with moderate renal impairment (eGFR ≥30 to <60 ml/min/1.73 m²) | |
|---|---|---|---|---|---|
| | Placebo (n=95) | Empagliflozin 10 mg (n=98) | Empagliflozin 25 mg (n=97) | Placebo (n=187) | Empagliflozin 25 mg (n=187) |
| Body weight (kg) | | | | | |
| Baseline (SE) | 86.00 (2.05) | 92.05 (2.16) | 88.06 (2.20) | 82.49 (1.32) | 83.22 (1.43) |
| Change from baseline at week 24 (SE) | −0.33 (0.24) | −1.76 (0.23)*** | −2.33 (0.23)*** | −0.08 (0.18) | −0.98 (0.18)*** |
| Systolic BP (mmHg) | | | | | |
| Baseline (SE) | 134.69 (1.75) | 137.37 (1.51) | 133.68 (1.80) | 136.38 (1.34) | 136.64 (1.32) |
| Change from baseline at week 24 (SE) | 0.65 (1.19) | −2.92 (1.17)* | −4.47 (1.18)** | 0.40 (0.94) | −3.88 (0.94)** |
| Diastolic BP (mmHg) | | | | | |
| Baseline (SE) | 77.47 (0.96) | 76.52 (0.90) | 76.67 (0.91) | 74.57 (0.70) | 75.22 (0.73) |
| Change from baseline at week 24 (SE) | 1.09 (0.64) | −1.41 (0.63)** | −2.21 (0.63)*** | 0.22 (0.57) | −1.65 (0.57)* |

FIG. 1C

Adjusted means based on ANCOVA in full analysis set with last observation carried forward imputation. Analysis of patients who reached $HbA_{1c}$ <7.0% at week 24 used non-completers considered to be failures imputation. †Inclusion criteria: $HbA_{1c}$ ≥7.0% to ≤10.0%. §n=89 for placebo, n=94 for empagliflozin 10 mg, n=91 for empagliflozin 25 mg in the mild impairment group; n=178 for placebo, n=175 for empagliflozin 25 mg in the moderate impairment group. *p<0.05 vs placebo; p<0.01 vs placebo; *p<0.001 vs placebo.Confidence intervals only shown for confirmatory analyses. For each dose group within renal impairment subpopulation (mild and moderate only), statistical testing of the primary endpoint was hierarchical at alpha = 0.05.Further endpoints were called significant if p-values were smaller than nominal alpha = 0.05.

FIG. 2

|  | Normal | Renal impairment | | | |
|---|---|---|---|---|---|
|  |  | Mild | Moderate | Severe | Renal failure/ESRD |
| Pharmacokinetics | n=8 | n=9 | n=7 | n=8 | n=8 |
| $AUC_{0-\infty}$, nmol·h/L | 10,600 (16.4) | 12,700 (20.8) | 13,000 (25.1) | 17,700 (17.8) | 16,600 (38.7) |
| $C_{max}$, nmol/L | 1,240 (23.5) | 1,500 (29.4) | 1,290 (37.9) | 1,520 (31.6) | 1,290 (27.5) |
| $t_{max}$, h* | 1.0 (1.0–3.0) | 2.5 (2.0–4.0) | 2.0 (1.5–3.0) | 2.0 (0.7–4.0) | 2.5 (1.5–3.0) |
| $t_{½}$, h | 19.9 (58.8) | 24.6 (84.5) | 23.8 (87.9) | 27.9 (76.8) | 22.0 (74.3) |
| $f_{e0-96}$, % | 16.1 (26.7) | 11.7 (36.4) | 7.7 (70.1) | 3.6 (36.1) | 0.3 (56.4) |
| $CL_{R,0-96}$, mL/min | 28.5 (20.5) | 18.6 (46.9) | 11.8 (69.6) | 4.0 (30.6) | 0.5 (59.1) |
| Pharmacodynamics | n=8 | n=7 | n=5 | n=6 | n=5 |
| $UGE_{0-24}$, baseline, g | 4.49 (2.88) | 4.16 (3.08) | 0.97 (0.49) | 0.97 (0.43) | 2.16 (2.00) |
| $UGE_{0-24}$, g | 102.13 (7.92) | 65.75 (7.31) | 56.64 (17.13) | 19.22 (4.04) | 2.93 (1.28) |
| Change from baseline, g | 97.64 (7.20) | 61.59 (6.89) | 55.67 (16.89) | 18.25 (3.93) | 0.78 (0.90) |

Pharmacokinetic values are mean (coefficient of variation [%]) unless otherwise stated; pharmacodynamic values are mean (standard error).* Data are median (range)

FIG. 3

| Renal impairment group | Parameter | Adjusted GMR (renal impaired/ normal group) | 90% CI for adjusted GMR | |
|---|---|---|---|---|
| | | | Lower limit (%) | Upper limit (%) |
| Mild | $AUC_{0-\infty}$ | 118.2 | 96.2 | 145.4 |
| | $C_{max}$ | 118.8 | 93.62 | 150.8 |
| Moderate | $AUC_{0-\infty}$ | 119.9 | 96.3 | 149.5 |
| | $C_{max}$ | 102.3 | 79.3 | 131.9 |
| Severe | $AUC_{0-\infty}$ | 166.3 | 134.4 | 205.7 |
| | $C_{max}$ | 120.7 | 94.4 | 154.3 |
| Renal failure/ESRD | $AUC_{0-\infty}$ | 148.3 | 119.9 | 183.4 |
| | $C_{max}$ | 103.8 | 81.2 | 132.6 |

FIG. 7A

| | Patients with CKD stage 3A (eGFR ≥45 to <60 ml/min/1.73 m²) | | Patients with CKD stage 3B (eGFR ≥30 to <45 ml/min/1.73 m²) | | Patients with CKD stage 4 (eGFR ≥15 to <30 ml/min/1.73 m²; descriptive statistics only) | |
|---|---|---|---|---|---|---|
| | Placebo (n=89) | EMPA 25 mg (n=91) | Placebo (n=98) | EMPA 25 mg (n=96) | Placebo (n=37) | EMPA 25 mg (n=37) |
| HbA$_{1c}$ (%) | | | | | | |
| Baseline[†] (SE) | 8.08 (0.09) | 8.12 (0.08) | 8.01 (0.08) | 7.95 (0.08) | 8.16 (0.16) | 8.06 (0.17) |
| Change from baseline at week 52 (SE) | 0.06 (0.07) | −0.48 (0.07) | 0.19 (0.08) | −0.18 (0.08) | −0.37 (0.13) | 0.11 (0.24) |
| Difference vs placebo (95% CI) | | −0.54 (−0.74, −0.34)[*] | | −0.37 (−0.61, −0.14)[] | | |
| Patients with HbA$_{1c}$ ≥7.0% at baseline[§] who reached HbA1c <7.0% at week 52, n(%) | 5 (6.0) | 11 (12.8) | 6 (6.4) | 6 (6.7) | 4 (11.8) | 4 (12.1) |
| Odds ratio vs placebo | | 4.0[*] | | 1.1 | | |

FIG. 7B

| | Patients with CKD stage 3A (eGFR ≥45 to <60 ml/min/1.73 m²) | | Patients with CKD stage 3B (eGFR ≥30 to <45 ml/min/1.73 m²) | | Patients with CKD stage 4 (eGFR ≥15 to <30 ml/min/1.73 m²; descriptive statistics only) | |
|---|---|---|---|---|---|---|
| | Placebo (n=89) | EMPA 25 mg (n=91) | Placebo (n=98) | EMPA 25 mg (n=96) | Placebo (n=37) | EMPA 25 mg (n=37) |
| FPG (mg/dL) | | | | | | |
| Baseline (SE) | 154.1 (4.6) | 144.6 (4.14) | 134.4 (5.3) | 141.1 (3.4) | 147.3 (9.6) | 157.1 (8.8) |
| Change from baseline at week 52 (SE) | 2.6 (4.3) | −10.0 (4.3) | 9.0 (4.4) | −4.6 (4.5) | 6.8 (11.5) | −4.7 (12.1) |
| Difference vs placebo (95% CI) | | −12.6 (−24.7, −0.6)* | | −13.6 (−26.2, −1.1)* | | |
| Body weight (kg) | | | | | | |
| Baseline (SE) | 83.2 (1.8) | 84.9 (2.2) | 81.8 (1.9) | 81.6 (1.9) | 84.1 (3.5) | 77.9 (2.7) |
| Change from baseline at week 52 (SE) | −0.1 (0.3) | −1.4 (0.3) | 0.1 (0.31) | −1.0 (0.3) | −0.0 (0.6) | −1.0 (0.5) |
| Difference vs placebo (95% CI) | | −1.3 (−2.1, −0.5)** | | −1.1 (−1.93, −0.20)* | | |

FIG. 7C

|  | Patients with CKD stage 3A (eGFR ≥45 to <60 ml/min/1.73 m²) | | Patients with CKD stage 3B (eGFR ≥30 to <45 ml/min/1.73 m²) | | Patients with CKD stage 4 (eGFR ≥15 to <30 ml/min/1.73 m²; descriptive statistics only) | |
|---|---|---|---|---|---|---|
|  | Placebo (n=89) | EMPA 25 mg (n=91) | Placebo (n=98) | EMPA 25 mg (n=96) | Placebo (n=37) | EMPA 25 mg (n=37) |
| Systolic BP (mmHg) | | | | | | |
| Baseline (SE) | 137.3 (1.9) | 135.0 (2.0) | 135.6 (1.9) | 138.2 (1.7) | 146.2 (3.6) | 145.0 (3.4) |
| Change from baseline at week 52 (SE) | −0.9 (1.4) | −6.6 (1.4) | −0.7 (1.4) | −3.6 (1.4) | 1.0 (2.9) | −11.2 (2.6) |
| Difference vs placebo (95% CI) |  | −5.7 (−9.5, −1.9)** |  | −2.9 (−6.9, 1.1) |  |  |
| Diastolic BP (mmHg) | | | | | | |
| Baseline (SE) | 76.5 (0.9) | 75.0 (1.1) | 72.8 (1.0) | 75.4 (1.0) | 78.0 (2.0) | 77.2 (1.5) |
| Change from baseline at week 52 (SE) | −0.4 (0.7) | −2.9 (0.7) | −0.2 (0.8) | −0.7 (0.8) | 1.4 (1.4) | −4.3 (1.5) |
| Difference vs placebo (95% CI) |  | −2.4 (−4.4, −0.5)* |  | −0.5 (−2.9, 1.8) |  |  |

FIG. 7D

Adjusted means based on ANCOVA in full analysis set with last observation carried forward imputation (CKD stage 3A and 3B). Results in CKD stage 4 are descriptive statistics with last observation carried forward imputation. Analysis of patients who reached $HbA_{1c}$ <7.0% at week 52 used non-completers considered to be failures imputation. †Inclusion criteria: $HbA_{1c}$ ≥7.0% to ≤10.0%. §CKD stage 3A: n=84 for placebo, n=86 for EMPA 25 mg; CKD stage 3B: n=94 for placebo, n=89 for EMPA 25 mg; CKD stage 4: n=34 for placebo, n=33 for EMPA 25 mg. *p<0.05 vs placebo; p<0.01 vs placebo; *p<0.001 vs placebo.

PHARMACEUTICAL COMPOSITION, METHODS FOR TREATING AND USES THEREOF

TECHNICAL FIELD OF THE INVENTION

The present invention relates to certain SGLT-2 inhibitors for treating and/or preventing metabolic disorders, such as type 2 or type 1 diabetes mellitus or pre-diabetes, in patients with renal impairment or chronic kidney disease (CDK).

BACKGROUND OF THE INVENTION

Diabetes is a major public health problem, with a prevalence that is expected to reach 552 million people worldwide by 2030. Type 2 diabetes mellitus (T2DM) accounts for 90% of all diabetes cases. Most medications for the treatment of T2DM act through insulin-dependent mechanisms; the progressive loss of beta-cell function that is characteristic of T2DM means that most patients with T2DM ultimately require multiple therapies to maintain glycemic control.

Nephropathy is a well-established complication of poor glycemic control in patients with diabetes. An estimated 10-36% of patients with T2DM have some degree of renal impairment and chronic kidney disease (CKD) is present in approximately 40% of patients with diabetes. CKD has been classified into 5 stages, where stage 1 is kidney damage with normal GFR (mL/min/1.73 m$^2$) of ≥90; stage 2 is kidney damage with a mild decrease in GFR (GFR 60-89); stage 3 is a moderate decrease in GFR (GFR 30-59); stage 4 is a severe decrease in GFR (GFR 15-29); and stage 5 is kidney failure (GFR <15 or dialysis). The use of a number of anti-diabetes agents is restricted in patients with renal impairment. Metformin is contraindicated in patients with renal dysfunction due to the risk of accumulation and lactic acidosis. Caution is advised with the use of insulin secretagogues in renally impaired patients. The DPP-4 inhibitors saxagliptin, sitagliptin and vildagliptin (but not linagliptin) are predominantly excreted renally, so dose reduction is necessary in patients with advanced chronic kidney disease.

There is therefore a need for methods, medicaments and pharmaceutical compositions for the treatment of metabolic disorders, such as type 2 diabetes, in patients with renal impairment or chronic kidney disease (CDK).

SUMMARY OF THE INVENTION

The present invention relates to certain SGLT-2 inhibitors, in particular empagliflozin, for treating and/or preventing metabolic disorders, such as type 2 diabetes mellitus, in patients with renal impairment or chronic kidney disease (CDK).

Accordingly, in one embodiment, the present invention provides a method for using empagliflozin in one or more of the following methods:
  preventing, slowing the progression of, delaying or treating a metabolic disorder selected from the group consisting of type 2 diabetes mellitus, impaired glucose tolerance, impaired fasting blood glucose, hyperglycemia, postprandial hyperglycemia, hyperinsulinemia and metabolic syndrome; or
  slowing the progression of, delaying or treating of pre-diabetes; or
  preventing, slowing the progression of, delaying or treating of an onset of type 2 diabetes mellitus; or
  improving glycemic control and/or for reducing of fasting plasma glucose, of postprandial plasma glucose and/or of glycosylated hemoglobin HbA1c; or
  preventing, slowing, delaying or reversing progression from impaired glucose tolerance, impaired fasting blood glucose, insulin resistance or from metabolic syndrome to type 2 diabetes mellitus; or
  preventing, slowing the progression of, delaying or treating of a condition or disorder selected from the group consisting of complications of diabetes mellitus such as cataracts and micro- and macrovascular diseases, such as nephropathy, retinopathy, neuropathy, tissue ischaemia, diabetic foot, dyslipidemia, arteriosclerosis, myocardial infarction, acute coronary syndrome, unstable angina pectoris, stable angina pectoris, stroke, peripheral arterial occlusive disease, cardiomyopathy, heart failure, heart rhythm disorders and vascular restenosis; or
  reducing body weight and/or body fat, or preventing an increase in body weight and/or body fat, or facilitating a reduction in body weight and/or body fat; or
  preventing, slowing, delaying or treating the degeneration of pancreatic beta cells and/or the decline of the functionality of pancreatic beta cells and/or for improving and/or restoring the functionality of pancreatic beta cells and/or restoring the functionality of pancreatic insulin secretion; or
  preventing, slowing, delaying or treating diseases or conditions attributed to an abnormal accumulation of ectopic fat, in particular liver fat; or
  for maintaining and/or improving the insulin sensitivity and/or for treating or preventing hyperinsulinemia and/or insulin resistance;
in a patient with renal impairment or chronic kidney disease (CDK), in particular a patient with mild or moderate renal impairment.

In one embodiment, the method comprises treating pre-diabetes, type 1 or type 2 diabetes mellitus. In one embodiment, the method comprises improving glycemic control in a patient with prediabetes, type 1 or type 2 diabetes mellitus.

Accordingly, in one embodiment, the present invention provides a method of treating prediabetes, type 1 or type 2 diabetes mellitus in patient comprising administering empagliflozin to the patient, wherein the patient has moderate renal impairment. In one embodiment, the patient has moderate A renal impairment. In one embodiment, the patient has moderate B renal impairment.

In one embodiment, the present invention further provides a method for improving glycemic control in a patient with prediabetes, type 1 or type 2 diabetes mellitus comprising administering empagliflozin to the patient, wherein the patient has moderate renal impairment. In one embodiment, the patient has moderate A renal impairment. In one embodiment, the patient has moderate B renal impairment.

In one embodiment, the present invention further provides a method of treating prediabetes, type 1 or type 2 diabetes mellitus in patient comprising administering empagliflozin to the patient, wherein the patient has stage 3 chronic kidney disease (CKD). In one embodiment, the patient has stage 3A chronic kidney disease (CKD). In one embodiment, the patient has stage 3B chronic kidney disease (CKD).

In one embodiment, the present invention further provides a method for improving glycemic control in a patient with prediabetes, type 1 or type 2 diabetes mellitus comprising administering empagliflozin to the patient, wherein the patient has stage 3 chronic kidney disease (CKD). In one embodiment, the patient has stage 3A chronic kidney disease (CKD). In one embodiment, the patient has stage 3B chronic kidney disease (CKD).

In one embodiment, the present invention further provides a method of treating prediabetes, type 1 or type 2 diabetes mellitus or improving glycemic control in a patient with prediabetes, type 1 or type 2 diabetes mellitus, said method comprising:
 a) assessing the renal function of a patient;
 b) treating a patient having moderate renal impairment with empagliflozin, but not treating a patient having severe renal impairment or kidney failure with empagliflozin.

In one embodiment, the method further comprises treating a patient having mild renal impairment or normal renal function with empagliflozin.

In one embodiment, the present invention further provides a method comprising:
 a) identifying a patient in need of treatment for type 2 diabetes mellitus;
 b) assessing the renal function of said patient;
 c) treating a patient having moderate renal impairment with empagliflozin, but not treating a patient having severe renal impairment or kidney failure with empagliflozin.

In one embodiment, the method further comprises treating a patient having mild renal impairment or normal renal function with empagliflozin.

In one embodiment, the present invention further provides a method of treating prediabetes, type 1 or type 2 diabetes mellitus or improving glycemic control in a patient with prediabetes, type 1 or type 2 diabetes mellitus, said method comprising:
 a) assessing the renal function of said patient;
 b) treating a patient having moderate A renal impairment with empagliflozin, but not treating a patient having moderate B renal impairment, severe renal impairment or kidney failure with empagliflozin.

In one embodiment, the method further comprises treating a patient having mild renal impairment or normal renal function with empagliflozin.

In one embodiment, the present invention further provides a method comprising:
 a) identifying a patient in need of treatment for type 2 diabetes mellitus;
 b) assessing the renal function of said patient;
 c) treating a patient having moderate A renal impairment with empagliflozin, but not treating a patient having moderate B renal impairment, severe renal impairment or kidney failure with empagliflozin.

In one embodiment, the method further comprises treating a patient having mild renal impairment or normal renal function with empagliflozin.

In one embodiment, the present invention further provides a method of treating type 2 diabetes comprising:
 a) determining the glomerular filtration rate (eGFR) of a patient in need of treatment for prediabetes, type 1 or type 2 diabetes mellitus;
 b) administering empagliflozin to the patient, if the eGFR of the patient is ≥30 ml/min/1.73 m$^2$.

In one embodiment, empagliflozin is administered if the eGFR of the patient is between ≥30 ml/min/1.73 m$^2$ and <60 ml/min/1.73 m$^2$. In one embodiment, the method further comprises discontinuing empagliflozin if the eGFR of the patient falls below 30 ml/min/1.73 m$^2$. In one embodiment, empagliflozin is administered if the eGFR of the patient is between ≥45 ml/min/1.73 m$^2$ and <60 ml/min/1.73 m$^2$. In one embodiment, the method further comprises discontinuing empagliflozin if the eGFR of the patient falls below 45 ml/min/1.73 m$^2$.

In one embodiment, the present invention further provides a method comprising:
 a) assessing the renal function of a patient;
 b) administering empagliflozin to the patient;
 c) discontinuing empagliflozin if the eGFR of the patient falls below 30 ml/min/1.73 m$^2$.

In one embodiment, empagliflozin is administered if the eGFR of the patient is between ≥30 ml/min/1.73 m$^2$ and <60 ml/min/1.73 m$^2$.

In one embodiment, the present invention further provides a method comprising:
 a) assessing the renal function of a patient;
 b) administering empagliflozin to the patient;
 c) discontinuing empagliflozin if the eGFR of the patient falls below 45 ml/min/1.73 m$^2$.

In one embodiment, empagliflozin is administered if the eGFR of the patient is between ≥45 ml/min/1.73 m$^2$ and <60 ml/min/1.73 m$^2$.

In one embodiment, the present invention further provides a method of treating prediabetes, type 1 or type 2 diabetes mellitus comprising:
 a) determining that the eGFR of a patient in need of treatment for type 2 diabetes mellitus is between ≥30 ml/min/1.73 m$^2$ and <60 ml/min/1.73 m$^2$;
 b) administering empagliflozin to the patient.

In one embodiment, the method further comprises discontinuing empagliflozin if the eGFR of the patient falls below 30 ml/min/1.73 m$^2$.

In one embodiment, the present invention further provides a method of treating prediabetes, type 1 or type 2 diabetes mellitus comprising:
 a) determining that the eGFR of a patient in need of treatment for type 2 diabetes mellitus is between ≥45 ml/min/1.73 m$^2$ and <60 ml/min/1.73 m$^2$;
 b) administering empagliflozin to the patient.

In one embodiment, the method further comprises discontinuing empagliflozin if the eGFR of the patient falls below 45 ml/min/1.73 m$^2$.

In one embodiment, the present invention further provides a method of treating prediabetes, type 1 or type 2 diabetes mellitus in a patient having an estimated glomerular filtration rate (eGFR) between ≥30 ml/min/1.73 m$^2$ and <60 ml/min/1.73 m$^2$ comprising:
 a) measuring the patient's estimated glomerular filtration rate (eGFR)
 b) measuring the effectiveness of empagliflozin for treatment of prediabetes, type 1 or type 2 diabetes mellitus in said patients; and
 c) administering empagliflozin to the patient.

In one embodiment, the patient has a glomerular filtration rate (eGFR) between ≥45 ml/min/1.73 m$^2$ and <60 ml/min/1.73 m$^2$. The effectiveness of empagliflozin is for example measured by determining the % HbA1c of the free plasma glucose (FPG) in the patient.

In one embodiment, the present invention further provides a method of treatment comprising:
 a) identifying a patient as being in need of treatment for prediabetes, type 1 or type 2 diabetes mellitus;
 b) determining that the patient's estimated glomerular filtration rate (eGFR) is ≥30 ml/min/1.73 m$^2$;
 c) selecting a prediabetes, type 1 or type 2 diabetes mellitus treatment for the patient that comprises the administration of empagliflozin, based on the recognition that empagliflozin is effective for treatment of type 2 diabetes mellitus in patients whose eGFR is ≥30 ml/min/1.73 m² and not in patients whose eGFR is <30 ml/min/1.73 m²; and d) administering empagliflozin to the patient.

In one embodiment, step b) comprises determining that the patient's estimated glomerular filtration rate (eGFR) is ≥30 ml/min/1.73 m² and <90 ml/min/1.73 m². In one embodiment, step b) comprises determining that the patient's estimated glomerular filtration rate (eGFR) is ≥30 ml/min/1.73 m² and <60 ml/min/1.73 m².

In one embodiment, the present invention further provides a method of treatment comprising:
  a) identifying a patient with prediabetes, type 1 or type 2 diabetes mellitus in need of improvement of glycemic control;
  b) determining that the patient's estimated glomerular filtration rate (eGFR) is ≥30 ml/min/1.73 m²;
  c) selecting a prediabetes, type 1 or type 2 diabetes mellitus treatment for the patient that comprises the administration of empagliflozin, based on the recognition that empagliflozin is effective for treatment of prediabetes, type 1 or type 2 diabetes mellitus in patients whose eGFR is ≥30 ml/min/1.73 m² and not in patients whose eGFR is <30 ml/min/1.73 m²; and
  d) administering empagliflozin to the patient.

In one embodiment, step b) comprises determining that the patient's estimated glomerular filtration rate (eGFR) is ≥30 ml/min/1.73 m² and <90 ml/min/1.73 m². In one embodiment, step b) comprises determining that the patient's estimated glomerular filtration rate (eGFR) is ≥30 ml/min/1.73 m² and <60 ml/min/1.73 m².

In one embodiment, the present invention further provides a method of treatment comprising:
  a) identifying a patient as being in need of treatment for prediabetes, type 1 or type 2 diabetes mellitus;
  b) measuring the patient's estimated glomerular filtration rate (eGFR);
  c) determining that the patient's eGFR is ≥30 ml/min/1.73 m² and <60 ml/min/1.73 m²;
  d) prescribing a prediabetes, type 1 or type 2 diabetes mellitus treatment for the patient that includes use of empagliflozin, based on the recognition that empagliflozin is effective for treatment of type 2 diabetes in patients whose eGFR is ≥30 ml/min/1.73 m² and not in patients whose eGFR is <30 ml/min/1.73 m²; and
  e) administering empagliflozin to the patient.

In one embodiment, the present invention further provides a method of treatment comprising:
  a) identifying a patient as being in need of treatment for prediabetes, type 1 or type 2 diabetes mellitus;
  b) determining that the patient's eGFR is ≥30 ml/min/1.73 m² and <60 ml/min/1.73 m²;
  c) selecting empagliflozin as a treatment for the patient based on the recognition that empagliflozin is effective for treatment of type 2 diabetes mellitus in patients who have an eGFR of ≥30 ml/min/1.73 m² but may lack efficacy in patients with eGFR <30 ml/min/1.73 m²;
  d) administering a pharmaceutical composition comprising empagliflozin to the patient;
  e) determining during treatment with the pharmaceutical composition that the patient's eGFR has dropped below 30 ml/min/1.73 m²; and
  f) ceasing treatment of the patient with the pharmaceutical composition, based on the recognition that empagliflozin may lack efficacy in patients with eGFR <30 ml/min/1.73 m².

In one embodiment, the present invention further provides a method of treatment comprising:
  a) identifying a patient as being in need of treatment for prediabetes, type 1 or type 2 diabetes mellitus;
  b) measuring the patient's estimated glomerular filtration rate (eGFR);
  c) determining that the patient's eGFR is ≥30 ml/min/1.73 m² and <60 ml/min/1.73 m².
  d) prescribing a type 2 diabetes treatment for the patient that includes use of empagliflozin, based on the recognition that empagliflozin is effective for treatment of type 2 diabetes in patients whose eGFR is ≥30 ml/min/1.73 m² and not in patients whose eGFR is <30 ml/min/1.73 m²; and
  e) advising the patient to self-administer empagliflozin.

In one embodiment, the present invention further provides a method of treatment comprising:
  a) identifying a patient as being in need of treatment for prediabetes, type 1 or type 2 diabetes mellitus;
  b) treating the patient with a first treatment regimen that does not comprise use of empagliflozin;
  c) determining that the first treatment regimen does not provide adequate glycemic control in the patient;
  d) measuring the patient's estimated glomerular filtration rate (eGFR);
  e) determining that the patient's eGFR is ≥30 ml/min/1.73 m² and <60 ml/min/1.73 m².
  f) prescribing an altered treatment regimen for the patient that includes use of empagliflozin, based on the recognition that empagliflozin is effective for treatment of prediabetes, type 1 or type 2 diabetes mellitus in patients whose eGFR is ≥30 ml/min/1.73 m² and not in patients whose eGFR is <30 ml/min/1.73 m²;
  g) advising the patient to administer empagliflozin daily as part of the altered treatment regimen; and
  h) confirming that the patient's glycemic control is improved on the altered treatment regimen, compared to on the first treatment regimen.

In one embodiment, the present invention further provides a method of treatment comprising:
  a) identifying a patient as being in need of treatment for prediabetes, type 1 or type 2 diabetes mellitus;
  b) determining that the patient's estimated glomerular filtration rate (eGFR) is ≥45 ml/min/1.73 m² and <60 ml/min/1.73 m²;
  c) selecting a type 2 diabetes treatment for the patient that includes empagliflozin, based on the recognition that empagliflozin is effective for treatment of prediabetes, type 1 or type 2 diabetes mellitus in patients whose eGFR is ≥45 ml/min/1.73 m² and not in patients whose eGFR is <45 ml/min/1.73 m²; and
  d) administering empagliflozin to the patient.

In one embodiment, the present invention further provides a method of treatment comprising:
  a) identifying a patient as being in need of treatment for prediabetes, type 1 or type 2 diabetes mellitus;
  b) measuring the patient's estimated glomerular filtration rate (eGFR);
  c) determining that the patient's eGFR is ≥45 ml/min/1.73 m² and <60 ml/min/1.73 m²;
  d) prescribing a prediabetes, type 1 or type 2 diabetes mellitus treatment for the patient that includes use of empagliflozin, based on the recognition that empagliflozin is effective for treatment of type 2 diabetes mellitus in patients whose eGFR is ≥45 ml/min/1.73 m² and not in patients whose eGFR is <45 ml/min/1.73 m²; and
  e) administering empagliflozin to the patient.

In one embodiment, the present invention further provides a method of treatment comprising:
a) identifying a patient as being in need of treatment for prediabetes, type 1 or type 2 diabetes mellitus;
b) determining that the patient's eGFR is ≥45 ml/min/1.73 m² and <60 ml/min/1.73 m²;
c) selecting empagliflozin as a treatment for the patient based on the recognition that empagliflozin is effective for treatment of prediabetes, type 1 or type 2 diabetes mellitus in patients who have an eGFR of ≥45 ml/min/1.73 m² but may lack efficacy in patients with eGFR <45 ml/min/1.73 m²;
d) administering a pharmaceutical composition comprising empagliflozin to the patient;
e) determining during treatment with the pharmaceutical composition that the patient's eGFR has dropped below 45 ml/min/1.73 m²; and
f) ceasing treatment of the patient with the pharmaceutical composition, based on the recognition that empagliflozin may lack efficacy in patients with eGFR <45 ml/min/1.73 m².

In one embodiment, the present invention further provides a method of treatment comprising:
a) identifying a patient as being in need of treatment for prediabetes, type 1 or type 2 diabetes mellitus;
b) measuring the patient's estimated glomerular filtration rate (eGFR);
c) determining that the patient's eGFR is ≥45 ml/min/1.73 m² and <60 ml/min/1.73 m²;
d) prescribing a type 2 diabetes treatment for the patient that includes use of empagliflozin, based on the recognition that empagliflozin is effective for treatment of prediabetes, type 1 or type 2 diabetes mellitus in patients whose eGFR is ≥45 ml/min/1.73 m² and not in patients whose eGFR is <45 ml/min/1.73 m²; and
e) advising the patient to self-administer empagliflozin.

In one embodiment, the present invention further provides a method of treatment comprising:
a) identifying a patient as being in need of treatment for prediabetes, type 1 or type 2 diabetes mellitus;
b) treating the patient with a first treatment regimen that does not comprise use of empagliflozin;
c) determining that the first treatment regimen does not provide adequate glycemic control in the patient;
d) measuring the patient's estimated glomerular filtration rate (eGFR);
e) determining that the patient's eGFR is ≥45 ml/min/1.73 m² and <60 ml/min/1.73 m²;
f) prescribing an altered treatment regimen for the patient that includes use of empagliflozin, based on the recognition that empagliflozin is effective for treatment of prediabetes, type 1 or type 2 diabetes mellitus in patients whose eGFR is ≥45 ml/min/1.73 m² and not in patients whose eGFR is <45 ml/min/1.73 m²;
g) advising the patient to administer empagliflozin daily as part of the altered treatment regimen; and
h) confirming that the patient's glycemic control is improved on the altered treatment regimen, compared to on the first treatment regimen.

In one embodiment, in any one of the methods above empagliflozin is administered as a pharmaceutical composition, for example a tablet. In one embodiment, the pharmaceutical composition comprises 10 mg or 25 mg of empagliflozin. In one embodiment, empagliflozin is administered once daily.

In one embodiment, the present invention further provides a method of improvement of glycemic control in a patient with prediabetes, type 1 or type 2 diabetes mellitus, wherein the patient's estimated glomerular filtration rate (eGFR) is ≥30 ml/min/1.73 m² comprising the administration of a pharmaceutical composition comprising empagliflozin to the patient. In one embodiment, the patient's estimated glomerular filtration rate (eGFR) is ≥45 ml/min/1.73 m². In one embodiment, the present invention further provides a method of improvement of glycemic control in a type 2 diabetes mellitus patient with moderate renal impairment comprising the administration of a pharmaceutical composition comprising empagliflozin to the patient. In one embodiment, the patient is with moderate A renal (CKD stage 3A) impairment. In one embodiment, the patient is with moderate B renal (CKD stage 3B) impairment. In one embodiment, the pharmaceutical composition comprises 10 mg or 25 mg of empagliflozin. In one embodiment, empagliflozin is administered once daily.

In one embodiment, the present invention further provides empagliflozin for use in the treatment of prediabetes, type 1 or type 2 diabetes mellitus in a patient wherein the patient's estimated glomerular filtration rate (eGFR) is ≥30 ml/min/1.73 m².

In one embodiment, the present invention further provides a pharmaceutical composition comprising empagliflozin for use in the treatment of prediabetes, type 1 or type 2 diabetes mellitus in a patient wherein the patient's estimated glomerular filtration rate (eGFR) is ≥30 ml/min/1.73 m².

In one embodiment, the present invention further provides empagliflozin for use in the improvement of glycemic control in a patient with prediabetes, type 1 or type 2 diabetes mellitus wherein the patient's estimated glomerular filtration rate (eGFR) is ≥30 ml/min/1.73 m².

In one embodiment, the present invention further provides a pharmaceutical composition comprising empagliflozin for use in the improvement of glycemic control in a patient with prediabetes, type 1 or type 2 diabetes mellitus wherein the patient's estimated glomerular filtration rate (eGFR) is ≥30 ml/min/1.73 m².

In one embodiment, in any of the use of empagliflozin or a pharmaceutical composition above, the patient's estimated glomerular filtration rate (eGFR) is ≥30 ml/min/1.73 m² and <90 ml/min/1.73 m². In one embodiment, the patient's estimated glomerular filtration rate (eGFR) is ≥30 ml/min/1.73 m² and <60 ml/min/1.73 m². In one embodiment, the patient's estimated glomerular filtration rate (eGFR) is ≥45 ml/min/1.73 m². In one embodiment, the patient's estimated glomerular filtration rate (eGFR) is ≥45 ml/min/1.73 m² and <90 ml/min/1.73 m². In one embodiment, the patient's estimated glomerular filtration rate (eGFR) is ≥45 ml/min/1.73 m² and <60 ml/min/1.73 m².

In one embodiment, the present invention further provides empagliflozin for use in the treatment of prediabetes, type 1 or type 2 diabetes mellitus in a patient with moderate renal impairment. In one embodiment, the present invention provides a pharmaceutical composition comprising empagliflozin for use in the treatment of prediabetes, type 1 or type 2 diabetes mellitus in a patient with moderate renal impairment. In one embodiment, the present invention provides empagliflozin for use in the improvement of glycemic control in a prediabetes, type 1 or type 2 diabetes mellitus patient with moderate renal impairment. In one embodiment, the present invention provides a pharmaceutical composition comprising empagliflozin for use in the improvement of glycemic control in a prediabetes, type 1 or type 2 diabetes mellitus patient with moderate renal impairment.

In one embodiment, in any use of empagliflozin or a pharmaceutical composition above, the patient is with moderate A renal impairment or with moderate B renal impairment. In one embodiment, the use is as an adjunct to diet and exercise. In one embodiment, the patient is an adult patient. In one embodiment, the use is once daily. In one embodiment, the use is 10 mg or 25 mg once daily.

In a further aspect of the present invention, empagliflozin is administered orally, for example in a total daily amount of 10 mg or 25 mg. In one embodiment, empagliflozin is administering as a pharmaceutical composition comprising 10 mg or 25 mg of empagliflozin, for example as a tablet.

In one aspect of the present invention, in a method or use disclosed herein a patient is patient with type 2 diabetes mellitus (or type 2 diabetes mellitus patient), a patient treated for type 2 diabetes mellitus, a patient diagnosed with type 2 diabetes mellitus or a patient in need of treatment for type 2 diabetes mellitus. In one aspect, a patient is a patient with pre-diabetes.

In a further aspect of the present invention, in a method or use as described herein empagliflozin is administered to a patient at a starting dose of 10 mg daily, for example to a patient as described herein. In one aspect, the dose of empagliflozin is increased to 25 mg daily, for example if the patient requires additional glycemic control. Accordingly, in a further aspect, the present invention provides a method or use as described herein comprising a) administering to a patient 10 mg of empagliflozin daily, b) determining that the patient requires additional glycemic control and c) administering to the patient 25 mg of empagliflozin daily.

In a further aspect, the present invention provides a method of improving glycemic control in a patient with type 2 diabetes mellitus, said method comprising a) administering to a patient 10 mg of empagliflozin daily, b) determining that the patient requires additional glycemic control and c) administering to the patient 25 mg of empagliflozin daily.

In a further aspect of the present invention, in a method or use described herein empagliflozin is administered to a patient at a starting dose of 10 mg daily, for example to a patient having an eGFR ≥30 ml/min/1.73 m$^2$ or to a patient having an eGFR ≥45 ml/min/1.73 m$^2$. In one aspect, in said method or use, the dose is increased to 25 mg daily, for example if the patient requires additional glycemic control. In one aspect, the dose of empagliflozin is increased to 25 mg daily in a patient having an eGFR ≥30 ml/min/1.73 m$^2$, in a patient having an eGFR ≥45 ml/min/1.73 m$^2$ or in a patient having an eGFR ≥60 ml/min/1.73 m$^2$.

In a further aspect, the present invention provides a method of improving glycemic control in a patient with type 2 diabetes mellitus, said method comprising a) administering 10 mg of empagliflozin daily to a patient having an eGFR ≥30 ml/min/1.73 m$^2$ and b) increasing the dose of empagliflozin administered to the patient to 25 mg daily in a patient having an eGFR ≥30 ml/min/1.73 m$^2$. In one aspect, said patient in step a) requires additional glycemic control.

In a further aspect, the present invention provides a method of improving glycemic control in a patient with type 2 diabetes mellitus, said method comprising a) administering 10 mg of empagliflozin daily to a patient having an eGFR ≥30 ml/min/1.73 m$^2$, b) determining that the patient has an eGFR ≥30 ml/min/1.73 m$^2$ and c) administering 25 mg of empagliflozin daily to the patient. In one aspect, step b) further comprises determining that the patient requires additional glycemic control.

In a further aspect, the present invention provides a method of improving glycemic control in a patient with type 2 diabetes mellitus, said method comprising a) administering 10 mg of empagliflozin daily to a patient having an eGFR ≥30 ml/min/1.73 m$^2$ and b) increasing the dose of empagliflozin administered to the patient to 25 mg daily in a patient having an eGFR ≥45 ml/min/1.73 m$^2$. In one aspect, said patient in step a) requires additional glycemic control.

In a further aspect, the present invention provides a method of improving glycemic control in a patient with type 2 diabetes mellitus, said method comprising a) administering 10 mg of empagliflozin daily to a patient having an eGFR ≥30 ml/min/1.73 m$^2$, b) determining that the patient has an eGFR ≥45 ml/min/1.73 m$^2$ and c) administering 25 mg of empagliflozin daily to the patient. In one aspect, step b) further comprises determining that the patient requires additional glycemic control.

In a further aspect, the present invention provides a method of improving glycemic control in a patient with type 2 diabetes mellitus, said method comprising a) administering 10 mg of empagliflozin daily to a patient having an eGFR ≥30 ml/min/1.73 m$^2$ and b) increasing the dose of empagliflozin administered to the patient to 25 mg daily in a patient having an eGFR ≥60 ml/min/1.73 m$^2$. In one aspect, said patient in step a) requires additional glycemic control.

In a further aspect, the present invention provides a method of improving glycemic control in a patient with type 2 diabetes mellitus, said method comprising a) administering 10 mg of empagliflozin daily to a patient having an eGFR ≥30 ml/min/1.73 m$^2$, b) determining that the patient has an eGFR ≥60 ml/min/1.73 m$^2$ and c) administering 25 mg of empagliflozin daily to the patient. In one aspect, step b) further comprises determining that the patient requires additional glycemic control.

In a further aspect, the present invention provides a method of improving glycemic control in a patient with type 2 diabetes mellitus, said method comprising a) administering 10 mg of empagliflozin daily to a patient having an eGFR ≥45 ml/min/1.73 m$^2$ and b) increasing the dose of empagliflozin administered to the patient to 25 mg daily in a patient having an eGFR ≥45 ml/min/1.73 m$^2$. In one aspect, said patient in step a) requires additional glycemic control.

In a further aspect, the present invention provides a method of improving glycemic control in a patient with type 2 diabetes mellitus, said method comprising a) administering 10 mg of empagliflozin daily to a patient having an eGFR ≥45 ml/min/1.73 m$^2$, b) determining that the patient has an eGFR ≥45 ml/min/1.73 m$^2$ and c) administering 25 mg of empagliflozin daily to the patient. In one aspect, step b) further comprises determining that the patient requires additional glycemic control.

In a further aspect, the present invention provides a method of improving glycemic control in a patient with type 2 diabetes mellitus, said method comprising a) administering 10 mg of empagliflozin daily to a patient having an eGFR ≥45 ml/min/1.73 m$^2$ and b) increasing the dose of empagliflozin administered to the patient to 25 mg daily in a patient having an eGFR ≥60 ml/min/1.73 m$^2$. In one aspect, said patient in step a) requires additional glycemic control.

In a further aspect, the present invention provides a method of improving glycemic control in a patient with type 2 diabetes mellitus, said method comprising a) administering 10 mg of empagliflozin daily to a patient having an eGFR ≥45 ml/min/1.73 m$^2$, b) determining that the patient has an eGFR ≥60 ml/min/1.73 m$^2$ and c) administering 25 mg of empagliflozin daily to the patient. In one aspect, step b) further comprises determining that the patient requires additional glycemic control.

In a further embodiment, in a method or use described herein empagliflozin is administered to a patient at a dose of 10 mg daily to a patient having an eGFR ≥60 ml/min/1.73 m² and the patient continues to be administered empagliflozin at a dose of 10 mg daily if the patient's eGFR is reduced to ≥30 to <60 ml/min/1.73 m² or to ≥45 to <60 ml/min/1.73 m². Accordingly, in one aspect, the present invention provides a method of improving glycemic control in a patient with type 2 diabetes mellitus, said method comprising a) administering 10 mg of empagliflozin daily to a patient having an eGFR ≥60 ml/min/1.73 m², b) determining that the patient has an eGFR ≥30 to <60 ml/min/1.73 m² and c) continuing to administer 10 mg of empagliflozin daily to the patient. In an another aspect, the present invention provides a method of improving glycemic control in a patient with type 2 diabetes mellitus, said method comprising a) administering 10 mg of empagliflozin daily to a patient having an eGFR ≥60 ml/min/1.73 m², b) determining that the patient has an eGFR ≥45 to <60 ml/min/1.73 m² and c) continuing to administer 10 mg of empagliflozin daily to the patient.

In a further embodiment, in a method or use described herein empagliflozin is administered to a patient at a starting dose of 10 mg daily to a patient having an eGFR ≥60 ml/min/1.73 m², the dose of empagliflozin is increased to 25 mg daily, for example if the patient requires additional glycemic control, and the dose of empagliflozin administered to the patient stays at a dose of 25 mg daily if the patient's eGFR is reduced to ≥30 to <60 ml/min/1.73 m² or to ≥45 to <60 ml/min/1.73 m². Accordingly, in one aspect, the present invention provides a method of improving glycemic control in a patient with type 2 diabetes mellitus, said method comprising a) administering 10 mg of empagliflozin daily to a patient having an eGFR ≥60 ml/min/1.73 m², b) increasing the dose of empagliflozin administered to the patient to 25 mg daily, for example if the patient requires additional glycemic control, c) determining that the patient has an eGFR ≥30 to <60 ml/min/1.73 m² and d) administering 25 mg of empagliflozin daily to the patient. In a further aspect, the present invention provides a method of improving glycemic control in a patient with type 2 diabetes mellitus, said method comprising a) administering 10 mg of empagliflozin daily to a patient having an eGFR ≥60 ml/min/1.73 m², b) increasing the dose of empagliflozin administered to the patient to 25 mg daily, for example if the patient requires additional glycemic control, c) determining that the patient has an eGFR ≥45 to <60 ml/min/1.73 m² and d) administering 25 mg empagliflozin daily to the patient.

In a further embodiment, in a method or use described herein empagliflozin is administered to a patient at a starting dose of 10 mg daily to a patient having an eGFR ≥60 ml/min/1.73 m², the dose of empagliflozin is increased to 25 mg daily, for example if the patient requires additional glycemic control, and the dose of empagliflozin administered to the patient is reduced to a dose of 10 mg daily if the patient's eGFR is reduced to ≥30 to <60 ml/min/1.73 m² or to ≥45 to <60 ml/min/1.73 m². Accordingly, in one aspect, the present invention provides a method of improving glycemic control in a patient with type 2 diabetes mellitus, said method comprising a) administering 10 mg of empagliflozin daily to a patient having an eGFR ≥60 ml/min/1.73 m², b) increasing the dose of empagliflozin administered to the patient to 25 mg daily, for example if the patient requires additional glycemic control, c) determining that the patient has an eGFR ≥30 to <60 ml/min/1.73 m² and d) administering 10 mg of empagliflozin daily to the patient. In a further aspect, the present invention provides a method of improving glycemic control in a patient with type 2 diabetes mellitus, said method comprising a) administering 10 mg of empagliflozin daily to a patient having an eGFR ≥60 ml/min/1.73 m², b) increasing the dose of empagliflozin administered to the patient to 25 mg daily, for example if the patient requires additional glycemic control, c) determining that the patient has an eGFR ≥45 to <60 ml/min/1.73 m² and d) administering 10 mg of empagliflozin daily to the patient.

In one aspect, in any one of the methods of uses described above, empagliflozin is administered once daily to a patient, i.e. for example 10 mg or 25 mg of empagliflozin is administered once daily to a patient.

In one aspect of the present invention, empagliflozin is administered with one or more other antidiabetic substances. In one embodiment, the other antidiabetic substances are selected from metformin, sulphonylureas, nateglinide, repaglinide, thiazolidinediones, PPARalpha-glucosidase inhibitors, insulin and insulin analogues, GLP-1 and GLP-1 analogues and DPP-4 inhibitors. In one aspect, the present invention comprises administering empagliflozin in combination with metformin and/or a DPP-4 inhibitor, for example linagliptin.

The present invention further provides for empagliflozin or a pharmaceutical composition comprising empagliflozin for use as a medicament in any one of the methods described herein.

The present invention further provides for empagliflozin or a pharmaceutical composition comprising empagliflozin for use in the treatment of any one of the diseases or conditions described herein.

The present invention further provides for empagliflozin or a pharmaceutical composition comprising empagliflozin for use in the manufacture of a medicament for use in any one of the methods described herein.

Definitions

The term "active ingredient" of a pharmaceutical composition according to the present invention means the SGLT2 inhibitor according to the present invention. An "active ingredient" is also sometimes referred to herein as an "active substance".

The term "body mass index" or "BMI" of a human patient is defined as the weight in kilograms divided by the square of the height in meters, such that BMI has units of kg/m².

The term "overweight" is defined as the condition wherein the individual has a BMI greater than or 25 kg/m² and less than 30 kg/m². The terms "overweight" and "pre-obese" are used interchangeably.

The terms "obesity" or "being obese" and the like are defined as the condition wherein the individual has a BMI equal to or greater than 30 kg/m². According to a WHO definition the term obesity may be categorized as follows: the term "class I obesity" is the condition wherein the BMI is equal to or greater than 30 kg/m² but lower than 35 kg/m²; the term "class II obesity" is the condition wherein the BMI is equal to or greater than 35 kg/m² but lower than 40 kg/m²; the term "class III obesity" is the condition wherein the BMI is equal to or greater than 40 kg/m².

The indication obesity includes in particular exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity, central obesity, visceral obesity, abdominal obesity.

The term "visceral obesity" is defined as the condition wherein a waist-to-hip ratio of greater than or equal to 1.0 in men and 0.8 in women is measured. It defines the risk for insulin resistance and the development of pre-diabetes.

The term "abdominal obesity" is usually defined as the condition wherein the waist circumference is >40 inches or 102 cm in men, and is >35 inches or 94 cm in women. With regard to a Japanese ethnicity or Japanese patients abdominal obesity may be defined as waist circumference ≥85 cm in men and ≥90 cm in women (see e.g. investigating committee for the diagnosis of metabolic syndrome in Japan).

The term "euglycemia" is defined as the condition in which a subject has a fasting blood glucose concentration within the normal range, greater than 70 mg/dL (3.89 mmol/L) and less than 100 mg/dL (5.6 mmol/L). The word "fasting" has the usual meaning as a medical term.

The term "hyperglycemia" is defined as the condition in which a subject has a fasting blood glucose concentration above the normal range, greater than 100 mg/dL (5.6 mmol/L). The word "fasting" has the usual meaning as a medical term.

The term "hypoglycemia" is defined as the condition in which a subject has a blood glucose concentration below the normal range, in particular below 70 mg/dL (3.89 mmol/L).

The term "postprandial hyperglycemia" is defined as the condition in which a subject has a 2 hour postprandial blood glucose or serum glucose concentration greater than 200 mg/dL (11.11 mmol/L).

The term "impaired fasting blood glucose" or "IFG" is defined as the condition in which a subject has a fasting blood glucose concentration or fasting serum glucose concentration in a range from 100 to 125 mg/dl (i.e. from 5.6 to 6.9 mmol/l), in particular greater than 110 mg/dL and less than 126 mg/dl (7.00 mmol/L). A subject with "normal fasting glucose" has a fasting glucose concentration smaller than 100 mg/dl, i.e. smaller than 5.6 mmol/l.

The term "impaired glucose tolerance" or "IGT" is defined as the condition in which a subject has a 2 hour postprandial blood glucose or serum glucose concentration greater than 140 mg/dl (7.78 mmol/L) and less than 200 mg/dL (11.11 mmol/L). The abnormal glucose tolerance, i.e. the 2 hour postprandial blood glucose or serum glucose concentration can be measured as the blood sugar level in mg of glucose per dL of plasma 2 hours after taking 75 g of glucose after a fast. A subject with "normal glucose tolerance" has a 2 hour postprandial blood glucose or serum glucose concentration smaller than 140 mg/dl (7.78 mmol/L).

The term "hyperinsulinemia" is defined as the condition in which a subject with insulin resistance, with or without euglycemia, has fasting or postprandial serum or plasma insulin concentration elevated above that of normal, lean individuals without insulin resistance, having a waist-to-hip ratio <1.0 (for men) or <0.8 (for women).

The terms "insulin-sensitizing", "insulin resistance-improving" or "insulin resistance-lowering" are synonymous and used interchangeably.

The term "insulin resistance" is defined as a state in which circulating insulin levels in excess of the normal response to a glucose load are required to maintain the euglycemic state (Ford E S, et al. JAMA. (2002) 287:356-9). A method of determining insulin resistance is the euglycaemic-hyperinsulinaemic clamp test. The ratio of insulin to glucose is determined within the scope of a combined insulin-glucose infusion technique. There is found to be insulin resistance if the glucose absorption is below the 25th percentile of the background population investigated (WHO definition). Rather less laborious than the clamp test are so called minimal models in which, during an intravenous glucose tolerance test, the insulin and glucose concentrations in the blood are measured at fixed time intervals and from these the insulin resistance is calculated. With this method, it is not possible to distinguish between hepatic and peripheral insulin resistance.

Furthermore, insulin resistance, the response of a patient with insulin resistance to therapy, insulin sensitivity and hyperinsulinemia may be quantified by assessing the "homeostasis model assessment to insulin resistance (HOMA-IR)" score, a reliable indicator of insulin resistance (Katsuki A, et al. Diabetes Care 2001; 24: 362-5). Further reference is made to methods for the determination of the HOMA-index for insulin sensitivity (Matthews et al., Diabetologia 1985, 28: 412-19), of the ratio of intact proinsulin to insulin (Forst et al., Diabetes 2003, 52(Suppl. 1): A459) and to an euglycemic clamp study. In addition, plasma adiponectin levels can be monitored as a potential surrogate of insulin sensitivity. The estimate of insulin resistance by the homeostasis assessment model (HOMA)-IR score is calculated with the formula (Galvin P, et al. Diabet Med 1992; 9:921-8):

$$\text{HOMA-IR} = [\text{fasting serum insulin } (\mu U/mL)] \times [\text{fasting plasma glucose(mmol/L)}/22.5]$$

Insulin resistance can be confirmed in these individuals by calculating the HOMA-IR score. For the purpose of this invention, insulin resistance is defined as the clinical condition in which an individual has a HOMA-IR score >4.0 or a HOMA-IR score above the upper limit of normal as defined for the laboratory performing the glucose and insulin assays.

As a rule, other parameters are used in everyday clinical practice to assess insulin resistance. Preferably, the patient's triglyceride concentration is used, for example, as increased triglyceride levels correlate significantly with the presence of insulin resistance.

Individuals likely to have insulin resistance are those who have two or more of the following attributes: 1) overweight or obese, 2) high blood pressure, 3) hyperlipidemia, 4) one or more $1^{st}$ degree relative with a diagnosis of IGT or IFG or type 2 diabetes.

Patients with a predisposition for the development of IGT or IFG or type 2 diabetes are those having euglycemia with hyperinsulinemia and are by definition, insulin resistant. A typical patient with insulin resistance is usually overweight or obese. If insulin resistance can be detected, this is a particularly strong indication of the presence of pre-diabetes. Thus, it may be that in order to maintain glucose homoeostasis a person needs 2-3 times as much insulin as a healthy person, without this resulting in any clinical symptoms.

"Pre-diabetes" is a general term that refers to an intermediate stage between normal glucose tolerance (NGT) and overt type 2 diabetes mellitus (T2DM), also referred to as intermediate hyperglycaemia. As such, it represents 3 groups of individuals, those with impaired glucose tolerance (IGT) alone, those with impaired fasting glucose (IFG) alone or those with both IGT and IFG. IGT and IFG usually have distinct pathophysiologic etiologies, however also a mixed condition with features of both can exist in patients. Therefore in the context of the present invention a patient being diagnosed of having "pre-diabetes" is an individual with diagnosed IGT or diagnosed IFG or diagnosed with both IGT and IFG. Following the definition according to the American Diabetes Association (ADA) and in the context of the present invention a patient being diagnosed of having "pre-diabetes" is an individual with:

a) a fasting plasma glucose (FPG) concentration <100 mg/dL [1 mg/dL=0.05555 mmol/L] and a 2-hour plasma glucose (PG) concentration, measured by a 75-g oral glucose tolerance test (OGTT), ranging between ≥140 mg/dL and <200 mg/dL (i.e., IGT); or b) a fasting plasma glucose (FPG) concentration between ≥100 mg/dL and <126 mg/dL and a 2-hour plasma glucose (PG) concentration, measured by a 75-g oral glucose tolerance test (OGTT) of <140 mg/dL (i.e., IFG); or c) a fasting plasma glucose (FPG) concentration between ≥100 mg/dL and <126 mg/dL and a 2-hour plasma glucose (PG) concentration, measured by a 75-g oral glucose tolerance test (OGTT), ranging between ≥140 mg/dL and <200 mg/dL (i.e., both IGT and IFG).

Patients with "pre-diabetes" are individuals being predisposed to the development of type 2 diabetes. Pre-diabetes extends the definition of IGT to include individuals with a fasting blood glucose within the high normal range ≥100 mg/dL (J. B. Meigs, et al. Diabetes 2003; 52:1475-1484). The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749).

The methods to investigate the function of pancreatic beta-cells are similar to the above methods with regard to insulin sensitivity, hyperinsulinemia or insulin resistance: An improvement of beta-cell function can be measured for example by determining a HOMA-index for beta-cell function (Matthews et al., *Diabetologia* 1985, 28: 412-19), the ratio of intact proinsulin to insulin (Forst et al., *Diabetes* 2003, 52(Suppl. 1): A459), the insulin/C-peptide secretion after an oral glucose tolerance test or a meal tolerance test, or by employing a hyperglycemic clamp study and/or minimal modeling after a frequently sampled intravenous glucose tolerance test (Stumvoll et al., *Eur J Clin Invest* 2001, 31: 380-81).

The term "type 1 diabetes" is defined as the condition in which a subject has, in the presence of autoimmunity towards the pancreatic beta-cell or insulin, a fasting blood glucose or serum glucose concentration greater than 125 mg/dL (6.94 mmol/L). If a glucose tolerance test is carried out, the blood sugar level of a diabetic will be in excess of 200 mg of glucose per dL (11.1 mmol/l) of plasma 2 hours after 75 g of glucose have been taken on an empty stomach, in the presence of autoimmunity towards the pancreatic beta cell or insulin. In a glucose tolerance test 75 g of glucose are administered orally to the patient being tested after 10-12 hours of fasting and the blood sugar level is recorded immediately before taking the glucose and 1 and 2 hours after taking it. The presence of autoimmunity towards the pancreatic beta-cell may be observed by detection of circulating islet cell autoantibodies ["type 1A diabetes mellitus"], i.e., at least one of: GAD65 [glutamic acid decarboxylase-65], ICA [islet-cell cytoplasm], IA-2 [intracytoplasmatic domain of the tyrosine phosphatase-like protein IA-2], ZnT8 [zinc-transporter-8] or anti-insulin; or other signs of autoimmunity without the presence of typical circulating autoantibodies [type 1B diabetes], i.e. as detected through pancreatic biopsy or imaging). Typically a genetic predisposition is present (e.g. HLA, INS VNTR and PTPN22), but this is not always the case.

The term "type 2 diabetes mellitus" or "T2DM" is defined as the condition in which a subject has a fasting blood glucose or serum glucose concentration greater than 125 mg/dL (6.94 mmol/L). The measurement of blood glucose values is a standard procedure in routine medical analysis. If a glucose tolerance test is carried out, the blood sugar level of a diabetic will be in excess of 200 mg of glucose per dL (11.1 mmol/l) of plasma 2 hours after 75 g of glucose have been taken on an empty stomach. In a glucose tolerance test 75 g of glucose are administered orally to the patient being tested after 10-12 hours of fasting and the blood sugar level is recorded immediately before taking the glucose and 1 and 2 hours after taking it. In a healthy subject, the blood sugar level before taking the glucose will be between 60 and 110 mg per dL of plasma, less than 200 mg per dL 1 hour after taking the glucose and less than 140 mg per dL after 2 hours. If after 2 hours the value is between 140 and 200 mg, this is regarded as abnormal glucose tolerance.

The term "late stage type 2 diabetes mellitus" includes patients with a secondary drug failure, indication for insulin therapy and progression to micro- and macrovascular complications e.g. diabetic nephropathy, or coronary heart disease (CHD).

The term "HbA1c" refers to the product of a non-enzymatic glycation of the haemoglobin B chain. Its determination is well known to one skilled in the art. In monitoring the treatment of diabetes mellitus the HbA1c value is of exceptional importance. As its production depends essentially on the blood sugar level and the life of the erythrocytes, the HbA1c in the sense of a "blood sugar memory" reflects the average blood sugar levels of the preceding 4-6 weeks. Diabetic patients whose HbA1c value is consistently well adjusted by intensive diabetes treatment (i.e. <6.5% of the total haemoglobin in the sample), are significantly better protected against diabetic microangiopathy. For example, metformin on its own achieves an average improvement in the HbA1c value in the diabetic of the order of 1.0-1.5%. This reduction of the HbA1C value is not sufficient in all diabetics to achieve the desired target range of <6.5% and preferably <6% HbA1c.

The term "insufficient glycemic control" or "inadequate glycemic control" in the scope of the present invention means a condition wherein patients show HbA1c values above 6.5%, in particular above 7.0%, even more preferably above 7.5%, especially above 8%.

The "metabolic syndrome", also called "syndrome X" (when used in the context of a metabolic disorder), also called the "dysmetabolic syndrome" is a syndrome complex with the cardinal feature being insulin resistance (Laaksonen D E, et al. *Am J Epidemiol* 2002; 156:1070-7). According to the ATP III/NCEP guidelines (Executive Summary of the Third Report of the National Cholesterol Education Program (NCEP) Expert Panel on Detection, Evaluation, and Treatment of High Blood Cholesterol in Adults (Adult Treatment Panel III) *JAMA: Journal of the American Medical Association* (2001) 285:2486-2497), diagnosis of the metabolic syndrome is made when three or more of the following risk factors are present:

1. Abdominal obesity, defined as waist circumference >40 inches or 102 cm in men, and >35 inches or 94 cm in women; or with regard to a Japanese ethnicity or Japanese patients defined as waist circumference ≥85 cm in men and ≥90 cm in women;
2. Triglycerides: ≥150 mg/dL 3. HDL-cholesterol <40 mg/dL in men
4. Blood pressure ≥130/85 mm Hg (SBP ≥130 or DBP ≥85)
5. Fasting blood glucose ≥100 mg/dL The NCEP definitions have been validated (Laaksonen D E, et al. *Am J Epidemiol*. (2002) 156:1070-7). Triglycerides and HDL cholesterol in the blood can also be determined by standard methods in medical analysis and are described for example in Thomas L (Editor): "Labor and Diagnose", TH-Books Verlagsgesellschaft mbH, Frankfurt/Main, 2000.

According to a commonly used definition, hypertension is diagnosed if the systolic blood pressure (SBP) exceeds a value of 140 mm Hg and diastolic blood pressure (DBP) exceeds a value of 90 mm Hg. If a patient is suffering from manifest diabetes it is currently recommended that the systolic blood pressure be reduced to a level below 130 mm Hg and the diastolic blood pressure be lowered to below 80 mm Hg.

The term "glomerular filtration rate (GFR)" is defined as the volume of fluid filtered from the renal (kidney) glomerular capillaries into the Bowman's capsule per unit time. It is indicative of overall kidney function. The glomerular filtration rate (GFR) can be calculated by measuring any chemical that has a steady level in the blood, and is freely filtered but neither reabsorbed nor secreted by the kidneys. The rate therefore measured is the quantity of the substance in the urine that originated from a calculable volume of blood. The GFR is typically recorded in units of volume per time, e.g., milliliters per minute and the formula below can be used:

GFR=(Urine Concentration×Urine Volume)/Plasma Concentration

The GFR can be determined by injecting inulin into the plasma. Since inulin is neither reabsorbed nor secreted by the kidney after glomerular filtration, its rate of excretion is directly proportional to the rate of filtration of water and solutes across the glomerular filter. A normal value is: GFR=90-125 mL/min/1.73 m², in particular GFR=100-125 mL/min/1.73 m².

Other principles to determine GFR involve measuring 51Cr-EDTA, [125I]iothalamate or iohexol.

The "estimated glomerular filtration rate (eGFR)" is defined as derived at screening from serum creatinine values based on e.g., the Chronic Kidney Disease Epidemiology Collaboration (CKD-EPI) equation, the Cockcroft-Gault formula or the Modification of Diet in Renal Disease (MDRD) formula, which are all known in the art.

The term "empagliflozin" refers to the SGLT2 inhibitor 1-chloro-4-(β-D-glucopyranos-1-yl)-2-[4-((S)-tetrahydrofuran-3-yloxy)-benzyl]-benzene of the formula

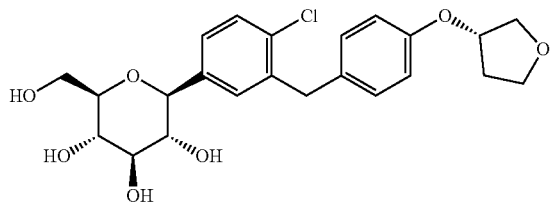 [SMILES: OC[C@H]1O[C@@H](c2ccc(Cl)c(Cc3ccc(O[C@H]4CCOC4)cc3)c2)[C@H](O)[C@@H](O)[C@@H]1O]

as described for example in WO 2005/092877. Methods of synthesis are described in the literature, for example WO 06/120208 and WO 2011/039108. According to this invention, it is to be understood that the definition of empagliflozin also comprises its hydrates, solvates and polymorphic forms thereof, and prodrugs thereof. An advantageous crystalline form of empagliflozin is described in WO 2006/117359 and WO 2011/039107 which hereby are incorporated herein in their entirety. This crystalline form possesses good solubility properties which enables a good bioavailability of the SGLT2 inhibitor. Furthermore, the crystalline form is physico-chemically stable and thus provides a good shelf-life stability of the pharmaceutical composition. Preferred pharmaceutical compositions, such as solid formulations for oral administration, for example tablets, are described in WO 2010/092126, which hereby is incorporated herein in its entirety.

The terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy.

The terms "prophylactically treating", "preventivally treating" and "preventing" are used interchangeably and comprise a treatment of patients at risk to develop a condition mentioned hereinbefore, thus reducing said risk.

The term "tablet" comprises tablets without a coating and tablets with one or more coatings. Furthermore the "term" tablet comprises tablets having one, two, three or even more layers and press-coated tablets, wherein each of the beforementioned types of tablets may be without or with one or more coatings. The term "tablet" also comprises mini, melt, chewable, effervescent and orally disintegrating tablets.

The terms "pharmacopoe" and "pharmacopoeias" refer to standard pharmacopoeias such as the "USP 31-NF 26 through Second Supplement" (United States Pharmacopeial Convention) or the "European Pharmacopoeia 6.3" (European Directorate for the Quality of Medicines and Health Care, 2000-2009).

BRIEF DESCRIPTION OF THE DRAWINGS

FIG. 1 A-C: Change from baseline in $HbA_{1c}$ fasting plasma glucose (FPG), weight and blood pressure (BP) at week 24 in patients with renal impairment treated with empagliflozin versus placebo.

FIG. 2: Pharmacokinetic and pharmacodynamic parameters for empagliflozin after administration of a single oral 50 mg dose in patients with renal impairment.

FIG. 3: Relative bioavailability of empagliflozin (50 mg qd) in subjects with impaired renal function compared with subjects with normal renal function (n=40).

FIG. 7 A-D: Change from baseline in $HbA_{1c}$ fasting plasma glucose (FPG), weight and blood pressure (BP) at week 52 in patients with Type 2 Diabetes Mellitus (T2DM) and Stage 3A, 3B and 4 Chronic Kidney Disease (CKD) treated with empagliflozin versus placebo.

DETAILED DESCRIPTION OF THE INVENTION

Figure 4A:
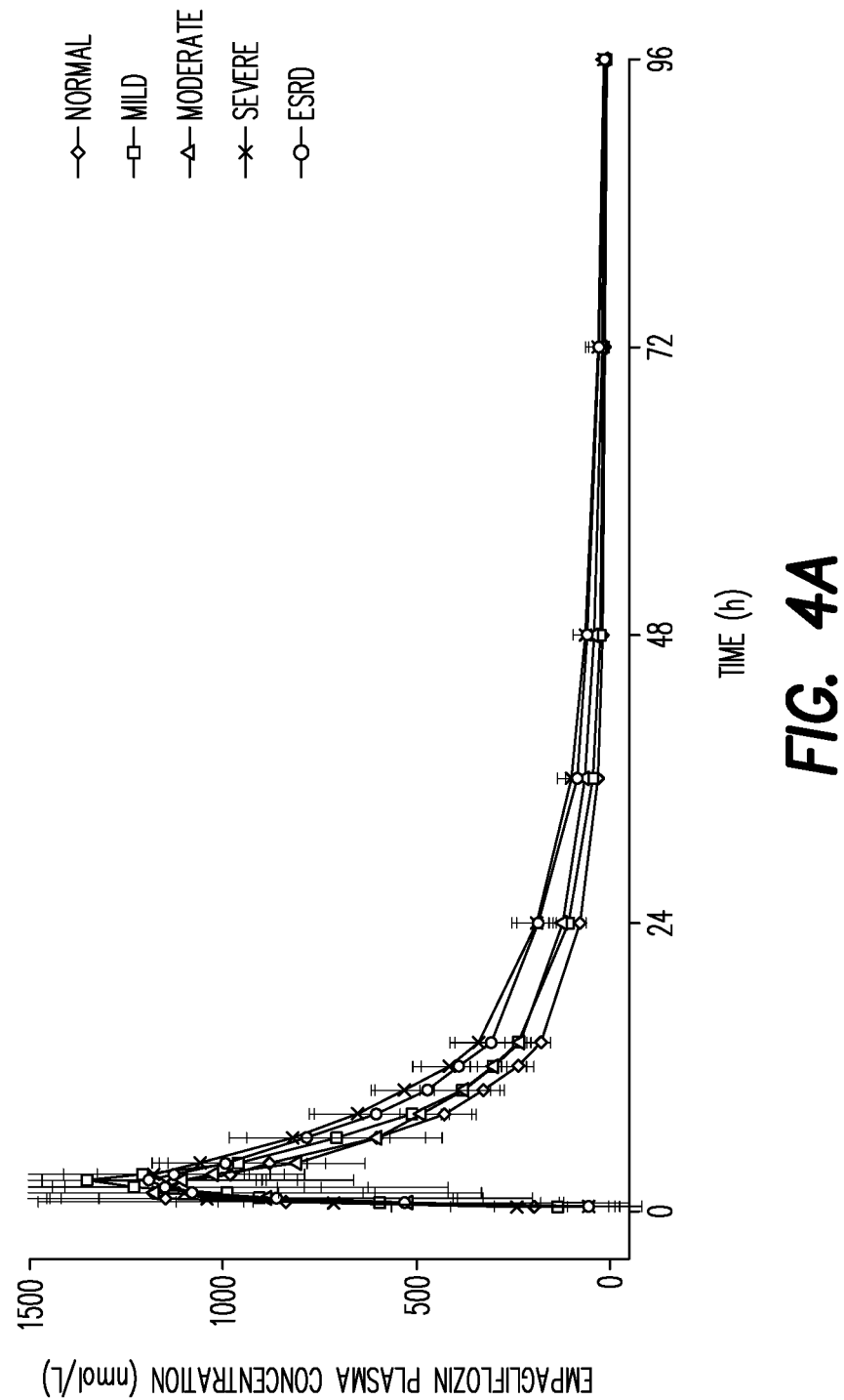
FIG. 4 A-D: Exposure to a single oral 50 mg dose of empagliflozin in subjects with normal and impaired renal function. (A) and (B) Mean plasma concentration-time profiles (insert: semi-log plot) (n=40). (C) $AUC_{0-\infty}$ and (D) $C_{max}$; midline of boxes are medians, and boundaries are 25th and 75th percentiles; whiskers are the standard span for the quartiles (1.5×interquartile range).

The present invention relates to certain SGLT-2 inhibitors, in particular empagliflozin, for treating and/or preventing a metabolic disorder, in particular type 1 or type 2 diabetes or pre-diabetes and/or diseases related thereto (e.g. diabetic complications), in patients with renal impairment or chronic kidney disease (CKD). In one aspect, the present invention relates to certain SGLT-2 inhibitors, in particular empagliflozin, for improving glycemic control in patient with type 1 or type 2 diabetes or pre-diabetes and with renal impairment or chronic kidney disease (CKD).

The treatment of type 2 diabetes typically begins with diet and exercise, followed by oral antidiabetic monotherapy, and although conventional monotherapy may initially control blood glucose in some patients, it is however associated with a high secondary failure rate. The limitations of single-agent therapy for maintaining glycemic control may be overcome, at least in some patients, and for a limited period of time by combining multiple drugs to achieve reductions in blood glucose that cannot be sustained during long-term therapy with single agents. Available data support the conclusion that in most patients with type 2 diabetes current monotherapy will fail and treatment with multiple drugs will be required.

But, because type 2 diabetes is a progressive disease, even patients with good initial responses to conventional combination therapy will eventually require an increase of the dosage or further treatment with insulin because the blood glucose level is very difficult to maintain stable for a long period of time. Although existing combination therapy has the potential to enhance glycemic control, it is not without limitations (especially with regard to long term efficacy). Further, traditional therapies may show an increased risk for side effects, such as hypoglycemia or weight gain, which may compromise their efficacy and acceptability.

Thus, for many patients, these existing drug therapies result in progressive deterioration in metabolic control despite treatment and do not sufficiently control metabolic status especially over long-term and thus fail to achieve and to maintain glycemic control in advanced or late stage type 2 diabetes, including diabetes with inadequate glycemic control despite conventional oral or non-oral antidiabetic medication.

Therefore, although intensive treatment of hyperglycemia can reduce the incidence of chronic damages, many patients with type 2 diabetes remain inadequately treated, partly because of limitations in long term efficacy, tolerability and dosing inconvenience of conventional antihyperglycemic therapies.

This high incidence of therapeutic failure is a major contributor to the high rate of long-term hyperglycemia-associated complications or chronic damages (including micro- and makrovascular complications such as e.g. diabetic nephrophathy, retinopathy or neuropathy, or cardiovascular complications such as e.g. myocardial infarction, stroke or vascular mortality or morbidity) in patients with type 2 diabetes.

Oral antidiabetic drugs conventionally used in therapy (such as e.g. first- or second-line, and/or mono- or (initial or add-on) combination therapy) include, without being restricted thereto, metformin, sulphonylureas, thiazolidindiones, glinides and α-glucosidase inhibitors.

Non-oral (typically injected) antidiabetic drugs conventionally used in therapy (such as e.g. first- or second-line, and/or mono- or (initial or add-on) combination therapy) include, without being restricted thereto, GLP-1 or GLP-1 analogues, and insulin or insulin analogues.

However, the use of these conventional antidiabetic or antihyperglycemic agents can be associated with various adverse effects. For example, metformin can be associated with lactic acidosis or gastrointestinal side effects; sulfonylureas, glinides and insulin or insulin analogues can be associated with hypoglycemia and weight gain; thiazolidindiones can be associated with edema, bone fracture, weight gain and heart failure/cardiac effects; and alpha-glucosidase blockers and GLP-1 or GLP-1 analogues can be associated with gastrointestinal adverse effects (e.g. dyspepsia, flatulence or diarrhea, or nausea or vomiting) and, most seriously (but rare), pancreatitis.

Type 1 diabetes mellitus (Type 1 diabetes), also called insulin dependent diabetes mellitus or juvenile diabetes, is a form of diabetes mellitus that results from autoimmune destruction of insulin-producing beta cells of the pancreas. The subsequent lack of insulin leads to increased blood glucose concentrations and increased urinary glucose excretion. The classical symptoms are polyuria, polydipsia, polyphagia, and weight loss. Type 1 diabetes may be fatal unless treated with insulin. Complications from type I diabetes are the same or similar to complications from type 2 diabetes. Standard therapy of type 1 diabetes is insulin treatment. Therapies for type 1 diabetes are for example described in WO 2012/062698.

SGLT2 inhibitors (sodium-glucose co-transporter 2) represent a novel class of agents that are being developed for the treatment or improvement in glycemic control in patients with type 2 diabetes. Glucopyranosyl-substituted benzene derivative are described as SGLT2 inhibitors, for example in WO 01/27128, WO 03/099836, WO 2005/092877, WO 2006/034489, WO 2006/064033, WO 2006/117359, WO 2006/117360, WO 2007/025943, WO 2007/028814, WO 2007/031548, WO 2007/093610, WO 2007/128749, WO 2008/049923, WO 2008/055870, WO 2008/055940. The glucopyranosyl-substituted benzene derivatives are proposed as inducers of urinary sugar excretion and as medicaments in the treatment of diabetes.

Renal filtration and reuptake of glucose contributes, among other mechanisms, to the steady state plasma glucose concentration and can therefore serve as an antidiabetic target. Reuptake of filtered glucose across epithelial cells of the kidney proceeds via sodium-dependent glucose cotransporters (SGLTs) located in the brush-border membranes in the tubuli along the sodium gradient. There are at least 3 SGLT isoforms that differ in their expression pattern as well as in their physico-chemical properties. SGLT2 is exclusively expressed in the kidney, whereas SGLT1 is expressed additionally in other tissues like intestine, colon, skeletal and cardiac muscle. SGLT3 has been found to be a glucose sensor in interstitial cells of the intestine without any transport function. Potentially, other related, but not yet characterized genes, may contribute further to renal glucose reuptake. Under normoglycemia, glucose is completely reabsorbed by SGLTs in the kidney, whereas the reuptake capacity of the kidney is saturated at glucose concentrations higher than 10 mM, resulting in glucosuria ("diabetes mellitus"). This threshold concentration can be decreased by SGLT2-inhibition. It has been shown in experiments with the SGLT inhibitor phlorizin that SGLT-inhibition will partially inhibit the reuptake of glucose from the glomerular filtrate into the blood leading to a decrease in blood glucose concentration and to glucosuria.

Empagliflozin is a novel SGLT2 inhibitor that is described for the treatment or improvement in glycemic control in patients with type 2 diabetes mellitus, for example in WO 05/092877, WO 06/117359, WO 06/120208, WO 2010/092126, WO 2010/092123, WO 2011/039107, WO 2011/039108.

Accordingly, in a particular embodiment, a SGLT-2 inhibitor within the meaning of this invention is empagliflozin.

The present invention relates to a therapeutic (treatment or prevention) method as described herein, said method comprising administering an effective amount of a SGLT-2 inhibitor as described herein and, optionally, one or more other active or therapeutic agents as described herein to a patient with renal impairment.

Patients with renal disease, renal dysfunction or renal impairment may include patients with chronic renal insufficiency or impairment, which can be stratified (if not otherwise noted) according to glomerular filtration rate (GFR, ml/min/1.73 m$^2$) into 5 disease stages: stage 1 characterized by normal GFR ≥90 plus either persistent albuminuria (e.g. UACR ≥30 mg/g) or known structural or hereditary renal disease; stage 2 characterized by mild reduction of GFR (GFR 60-89) describing mild renal impairment; stage 3 characterized by moderate reduction of GFR (GFR 30-59) describing moderate renal impairment; stage 4 characterized by severe reduction of GFR (GFR 15-29) describing severe renal impairment; and terminal stage 5 characterized by requiring dialysis or GFR <15 describing established kidney failure (end-stage renal disease, ESRD).

Accordingly, chronic kidney disease and its stages (CKD 1-5) can be usually characterized or classified accordingly, such as based on the presence of either kidney damage (albuminuria) or impaired estimated glomerular filtration rate (GFR <60 [ml/min/1.73 m$^2$], with or without kidney damage).

For the purpose of the present invention, the degree of renal impairment in a patient is defined by the following estimated glomerular filtration rate (eGFR):
Normal renal function: eGFR ≥90 ml/min/1.73 m$^2$
Mild renal impairment: eGFR ≥60 to <90 ml/min/1.73 m$^2$
Moderate renal impairment: eGFR ≥30 to <60 ml/min/1.73 m$^2$
Severe renal impairment: eGFR ≥15 to <30 ml/min/1.73 m$^2$
Kidney failure: eGFR <15 ml/min/1.73 m$^2$ Accordingly, in the context of the present invention, a patient with normal renal function has an eGFR ≥90 ml/min/1.73 m$^2$, a patient with mild renal impairment has an eGFR ≥60 to <90 ml/min/1.73 m$^2$, a patient with moderate renal impairment has an eGFR ≥30 to <60 ml/min/1.73 m$^2$, a patient with severe renal impairment has an eGFR ≥15 to <30 ml/min/1.73 m$^2$, a patient with kidney failure has an eGFR <15 ml/min/1.73 m$^2$.

According to the present invention moderate renal impairment can be further divided into two sub-stages:
Moderate A renal impairment (CKD 3A): eGFR ≥45 to <60 ml/min/1.73 m$^2$
Moderate B renal impairment (CKD 3B): eGFR ≥30 to <45 ml/min/1.73 m$^2$ Accordingly, in the context of the present invention, a patient with moderate A renal impairment has an eGFR ≥45 to <60 ml/min/1.73 m$^2$ and a patient with moderate B renal impairment has an eGFR ≥30 to <45 ml/min/1.73 m$^2$.

For the purpose of the present invention, the estimated glomerular filtration rate (eGFR) is derived from the serum creatinine (SCr) value based on the MDRD formula below:

$$\text{eGFR (mL/min/1.73 m2)} = 175 \times [\text{SCr}(\mu\text{mol/L})/88.4]^{-1.154} \times [\text{age}]^{-0.203} \times [0.742 \text{ if patient is female}] \times [1.212 \text{ if patient is of African origin}]$$

For additional analyses, renal function can also be classified by the estimated creatinine clearance rate (eCCr) value, based on the Cockcroft-Gault formula below:

$$\text{eCCr (mL/min)} = (140-\text{age}) \times (\text{weight in kg}) \times [0.85 \text{ if patient is female}]/(72 \times \text{SCr}(\text{mg/dL}))$$

Renal function classification based on eCCr is similar to the eGFR classification: normal renal function (≥90 mL/min), mild impairment (60 to <90 mL/min), moderate impairment (30 to <60 mL/min), and severe impairment (≥15 to <30 mL/min).

Generally, mild renal impairment according to the present invention corresponds to stage 2 chronic kidney disease, moderate renal impairment according to the present invention generally corresponds to stage 3 chronic kidney disease, and severe renal impairment according to the present invention generally corresponds to stage 4 chronic kidney disease. Likewise, moderate A renal impairment according to the present invention generally corresponds to stage 3A chronic kidney disease and moderate B renal impairment according to the present invention generally corresponds to stage 3B chronic kidney disease. Therefore, the methods and uses of SGLT-2 inhibitors, particularly empagliflozin, in the context of the present invention and applied to patients having renal impairment as defined herein also apply to patients having the corresponding stage of chronic kidney disease.

In some aspects, renal disease, renal dysfunction, or insufficiency or impairment of renal function (including mild, moderate and/or severe renal impairment) may also be suggested (if not otherwise noted) by elevated serum creatinine levels (e.g. serum creatinine levels above the upper limit of normal for their age, e.g. ≥130-150 µmol/l, or ≥1.5 mg/dl (≥136 µmol/l) in men and ≥1.4 mg/dl (≥124 µmol/l) in women) or abnormal creatinine clearance (e.g. glomerular filtration rate (GFR) ≤30-60 ml/min).

In some further aspects, mild renal impairment may be also suggested (if not otherwise noted) by a creatinine clearance of 50-80 ml/min (approximately corresponding to serum creatine levels of ≤1.7 mg/dL in men and ≤1.5 mg/dL in women); moderate renal impairment may be e.g. suggested (if not otherwise noted) by a creatinine clearance of 30-50 ml/min (approximately corresponding to serum creatinine levels of >1.7 to ≤3.0 mg/dL in men and >1.5 to ≤2.5 mg/dL in women); and severe renal impairment may be e.g. suggested (if not otherwise noted) by a creatinine clearance of <30 ml/min (approximately corresponding to serum creatinine levels of >3.0 mg/dL in men and >2.5 mg/dL in women). Patients with end-stage renal disease require dialysis (e.g. hemodialysis or peritoneal dialysis).

Albuminuria stages may be for example classified as disclosed herein and/or by urine albumin creatinine ratio (such as usually UACR ≥30 mg/g, in some instances ≥20 µg/min albumin excretion rate), such as e.g. microalbuminuria may be for example classified by UACR 30-300 mg/g (in some instances 20-200 µg/min) or, in another embodiment, by UACR 30-200 mg/g, and/or macroalbuminuria may be for example classified by UACR >300 mg/g (in some instances >200 μg/min), or, in another embodiment, by UACR >200 mg/g. Very high UACR ≥2000 mg/g may be classified as nephrotic.

Accordingly, in one embodiment, the present invention provides a method of treating type 2 diabetes in patient comprising administering empagliflozin to the patient, wherein the patient has moderate renal impairment (or CKD stage 3). In one embodiment, the patient has moderate A renal impairment (or CKD stage 3A). In one embodiment, the patient has moderate B renal impairment (or CKD stage 3B).

In a further embodiment, the present invention provides a method for improving glycemic control in a patient with type 2 diabetes comprising administering empagliflozin to the patient, wherein the patient has moderate renal impairment (or CKD stage 3). In one embodiment, the patient has moderate A renal impairment (or CKD stage 3A). In one embodiment, the patient has moderate B renal impairment (or CKD stage 3B).

In one aspect, in a method of the present invention, the renal function of a patient is monitored during the treatment with empagliflozin, for example by measuring the eGFR of the patient. For example, the renal function of a patient is monitored during the treatment with empagliflozin if the eGFR of the patient is below 60 ml/min/1.73 m$^2$ or below 45 ml/min/1.73 m$^2$. In one aspect, in such a method, the treatment with empagliflozin is discontinued if the eGFR of the patient falls below a certain value, for example below 30 ml/min/1.73 m$^2$ or below 45 ml/min/1.73 m$^2$.

In one embodiment, diabetes patients within the meaning of this invention may include patients who have not previously been treated with an antidiabetic drug (drug-naïve patients). Thus, in an embodiment, the therapies described herein may be used in naïve patients. In another embodiment, diabetes patients within the meaning of this invention may include patients with advanced or late stage type 2 diabetes mellitus (including patients with failure to conventional antidiabetic therapy), such as e.g. patients with inadequate glycemic control on one, two or more conventional oral and/or non-oral antidiabetic drugs as defined herein, such as e.g. patients with insufficient glycemic control despite (mono-)therapy with metformin, a thiazolidinedione (particularly pioglitazone), a sulphonylurea, a glinide, GLP-1 or GLP-1 analogue, insulin or insulin analogue, or an α-glucosidase inhibitor, or despite dual combination therapy with metformin/sulphonylurea, metformin/thiazolidinedione (particularly pioglitazone), sulphonylurea/α-glucosidase inhibitor, pioglitazone/sulphonylurea, metformin/insulin, pioglitazone/insulin or sulphonylurea/insulin. Thus, in an embodiment, the therapies described herein may be used in patients experienced with therapy, e.g. with conventional oral and/or non-oral antidiabetic mono- or dual or triple combination medication as mentioned herein.

A further embodiment of the diabetes patients which may be amenable to the therapies of this invention may include, without being limited, those diabetes patients (especially type 2 diabetes) with advanced age and/or with advanced diabetes disease, such as e.g. patients on insulin treatment, patients on triple antidiabetic oral therapy, patients with pre-existing cardiovascular events and/or patients with advanced disease duration (e.g. >/=5 to 10 years).

The present invention further relates to a pharmaceutical composition comprising a certain SGLT-2 inhibitor as defined herein, empagliflozin, for use in the therapies described herein.

When this invention refers to patients requiring treatment or prevention, it relates primarily to treatment and prevention in humans. In the scope of this invention adult patients are preferably humans of the age of 18 years or older. Also in the scope of this invention, patients are adolescent humans, i.e. humans of age 10 to 17 years, preferably of age 13 to 17 years. It is assumed that in a adolescent population the administration of the pharmaceutical composition according to the invention a very good HbA1c lowering and a very good lowering of the fasting plasma glucose can be seen. In addition it is assumed that in an adolescent population, in particular in overweight and/or obese patients, a pronounced weight loss can be observed.

As described hereinbefore by the administration of the pharmaceutical composition according to this invention and in particular in view of the high SGLT2 inhibitory activity of the SGLT2 inhibitors therein, excessive blood glucose is excreted through the urine of the patient, so that no gain in weight or even a reduction in body weight may result. Therefore, a treatment or prophylaxis according to this invention is advantageously suitable in those patients in need of such treatment or prophylaxis who are diagnosed of one or more of the conditions selected from the group consisting of overweight and obesity, in particular class I obesity, class II obesity, class III obesity, visceral obesity and abdominal obesity. In addition a treatment or prophylaxis according to this invention is advantageously suitable in those patients in which a weight increase is contraindicated. The pharmaceutical composition as well as the methods according to the present invention allow a reduction of the HbA1c value to a desired target range, for example <7% and preferably <6.5%, for a higher number of patients and for a longer time of therapeutic treatment compared with a corresponding monotherapy or a therapy using only two of the combination partners.

The pharmaceutical composition according to this invention and in particular the SGLT2 inhibitor therein exhibits a very good efficacy with regard to glycemic control, in particular in view of a reduction of fasting plasma glucose, postprandial plasma glucose and/or glycosylated hemoglobin (HbA1c). By administering a pharmaceutical composition according to this invention, a reduction of HbA1c equal to or greater than preferably 0.5%, even more preferably equal to or greater than 1.0% can be achieved and the reduction is particularly in the range from 1.0% to 2.0%.

Furthermore, the method and/or use according to this invention is advantageously applicable in those patients who show one, two or more of the following conditions:
(a) a fasting blood glucose or serum glucose concentration greater than 100 mg/dL, in particular greater than 125 mg/dL;
(b) a postprandial plasma glucose equal to or greater than 140 mg/dL;
(c) an HbA1c value equal to or greater than 6.5%, in particular equal to or greater than 7.0%, especially equal to or greater than 7.5%, even more particularly equal to or greater than 8.0%.

The present invention also discloses the use of the pharmaceutical composition for improving glycemic control in patients having type 1 or type 2 diabetes or showing first signs of pre-diabetes. Thus, the invention also includes diabetes prevention. If therefore a pharmaceutical composition according to this invention is used to improve the glycemic control as soon as one of the above-mentioned signs of pre-diabetes is present, the onset of manifest type 2 diabetes mellitus can be delayed or prevented.

Furthermore, the pharmaceutical composition according to this invention is particularly suitable in the treatment of patients with insulin dependency, i.e. in patients who are treated or otherwise would be treated or need treatment with an insulin or a derivative of insulin or a substitute of insulin or a formulation comprising an insulin or a derivative or substitute thereof. These patients include patients with diabetes type 2 and patients with diabetes type 1.

Therefore, according to a preferred embodiment of the present invention, there is provided a method for improving glycemic control and/or for reducing of fasting plasma glucose, of postprandial plasma glucose and/or of glycosylated hemoglobin HbA1c in a patient in need thereof who is diagnosed with impaired glucose tolerance (IGT), impaired fasting blood glucose (IFG) with insulin resistance, with metabolic syndrome and/or with type 2 or type 1 diabetes mellitus characterized in that an SGLT2 inhibitor as defined hereinbefore and hereinafter is administered to the patient.

According to another preferred embodiment of the present invention, there is provided a method for improving glycemic control in patients, in particular in adult patients, with type 2 diabetes mellitus as an adjunct to diet and exercise.

It can be found that by using a pharmaceutical composition according to this invention, an improvement of the glycemic control can be achieved even in those patients who have insufficient glycemic control in particular despite treatment with an antidiabetic drug, for example despite maximal recommended or tolerated dose of oral monotherapy with metformin. A maximal recommended dose with regard to metformin is for example 2000 mg per day or 850 mg three times a day or any equivalent thereof.

Therefore, the method and/or use according to this invention is advantageously applicable in those patients who show one, two or more of the following conditions:
(a) insufficient glycemic control with diet and exercise alone;
(b) insufficient glycemic control despite oral monotherapy with metformin, in particular despite oral monotherapy at a maximal tolerated dose of metformin;
(c) insufficient glycemic control despite oral monotherapy with another antidiabetic agent, in particular despite oral monotherapy at a maximal tolerated dose of the other antidiabetic agent.

The lowering of the blood glucose level by the administration of an SGLT2 inhibitor according to this invention is insulin-independent. Therefore, a pharmaceutical composition according to this invention is particularly suitable in the treatment of patients who are diagnosed having one or more of the following conditions
 insulin resistance,
 hyperinsulinemia,
 pre-diabetes,
 type 2 diabetes mellitus, particular having a late stage type 2 diabetes mellitus,
 type 1 diabetes mellitus.

Furthermore, a pharmaceutical composition according to this invention is particularly suitable in the treatment of patients who are diagnosed having one or more of the following conditions
(a) obesity (including class I, II and/or III obesity), visceral obesity and/or abdominal obesity,
(b) triglyceride blood level ≥150 mg/dL,
(c) HDL-cholesterol blood level <40 mg/dL in female patients and <50 mg/dL in male patients,
(d) a systolic blood pressure ≥130 mm Hg and a diastolic blood pressure ≥85 mm Hg,
(e) a fasting blood glucose level ≥100 mg/dL.

It is assumed that patients diagnosed with impaired glucose tolerance (IGT), impaired fasting blood glucose (IFG), with insulin resistance and/or with metabolic syndrome suffer from an increased risk of developing a cardiovascular disease, such as for example myocardial infarction, coronary heart disease, heart insufficiency, thromboembolic events.

Furthermore, a pharmaceutical composition according to this invention is particularly suitable in the treatment of patients after organ transplantation, in particular those patients who are diagnosed having one or more of the following conditions
(a) a higher age, in particular above 50 years,
(b) male gender;
(c) overweight, obesity (including class I, II and/or III obesity), visceral obesity and/or abdominal obesity,
(d) pre-transplant diabetes,
(e) immunosuppression therapy.

Furthermore, a pharmaceutical composition according to this invention is particularly suitable in the treatment of patients who are diagnosed having one or more of the following conditions:
(a) hyponatremia, in particular chronical hyponatremia;
(b) water intoxication;
(c) water retention;
(d) plasma sodium concentration below 135 mmol/L.

The patient may be a diabetic or non-diabetic mammal, in particular human.

Furthermore, a pharmaceutical composition according to this invention is particularly suitable in the treatment of patients who are diagnosed having one or more of the following conditions:
(a) high serum uric acid levels, in particular greater than 6.0 mg/dL (357 µmol/L);
(b) a history of gouty arthritis, in particular recurrent gouty arthritis;
(c) kidney stones, in particular recurrent kidney stones;
(d) a high propensity for kidney stone formation.

In certain embodiments, the patients which may be amenable to the therapies of this invention may have or are at-risk of one or more of the following diseases, disorders or conditions: type 1 diabetes, type 2 diabetes, impaired glucose tolerance (IGT), impaired fasting blood glucose (IFG), hyperglycemia, postprandial hyperglycemia, postabsorptive hyperglycemia, latent autoimmune diabetes in adults (LADA), overweight, obesity, dyslipidemia, hyperlipidemia, hypercholesterolemia, hypertriglyceridemia, hyper-NEFA-emia, postprandial lipemia, hypertension, atherosclerosis, endothelial dysfunction, osteoporosis, chronic systemic inflammation, non alcoholic fatty liver disease (NAFLD), polycystic ovarian syndrome, metabolic syndrome, nephropathy, micro- or macroalbuminuria, proteinuria, retinopathy, cataracts, neuropathy, learning or memory impairment, neurodegenerative or cognitive disorders, cardiovascular diseases, tissue ischaemia, diabetic foot or ulcus, atherosclerosis, hypertension, endothelial dysfunction, myocardial infarction, acute coronary syndrome, unstable angina pectoris, stable angina pectoris, peripheral arterial occlusive disease, cardiomyopathy (including e.g. uremic cardiomyopathy), heart failure, cardiac hypertrophy, heart rhythm disorders, vascular restenosis, stroke, (renal, cardiac, cerebral or hepatic) ischemia/reperfusion injuries, (renal, cardiac, cerebral or hepatic) fibrosis, (renal, cardiac, cerebral or hepatic) vascular remodeling; a diabetic disease, especially type 2 diabetes, mellitus may be preferred (e.g. as underlying disease).

In a further embodiment, the patients which may be amenable to the therapies of this invention have a diabetic disease, especially type 2 diabetes mellitus, and may have or are at-risk of one or more other diseases, disorders or conditions, such as e.g. selected from those mentioned immediately above.

Within the scope of the present invention it has now been found that certain SGLT-2 inhibitors as defined herein, optionally in combination with one or more other therapeutic substances (e.g. selected from those described herein), as well as pharmaceutical combinations, compositions or combined uses according to this invention of such SGLT-2 inhibitors as defined herein have properties, which make them suitable for the purpose of this invention and/or for fulfilling one or more of above needs.

The present invention thus relates to a certain SGLT-2 inhibitor as defined herein, preferably empagliflozin, for use in the therapies described herein.

Furthermore, it can be found that the administration of a pharmaceutical composition according to this invention results in no risk or in a low risk of hypoglycemia. Therefore, a treatment or prophylaxis according to this invention is also advantageously possible in those patients showing or having an increased risk for hypoglycemia.

A pharmaceutical composition according to this invention is particularly suitable in the long term treatment or prophylaxis of the diseases and/or conditions as described hereinbefore and hereinafter, in particular in the long term glycemic control in patients with type 2 diabetes mellitus.

The term "long term" as used hereinbefore and hereinafter indicates a treatment of or administration in a patient within a period of time longer than 12 weeks, preferably longer than 25 weeks, even more preferably longer than 1 year.

Therefore, a particularly preferred embodiment of the present invention provides a method for therapy, preferably oral therapy, for improvement, especially long term improvement, of glycemic control in patients with type 2 diabetes mellitus, especially in patients with late stage type 2 diabetes mellitus, in particular in patients additionally diagnosed of overweight, obesity (including class I, class II and/or class III obesity), visceral obesity and/or abdominal obesity.

It will be appreciated that the amount of the pharmaceutical composition according to this invention to be administered to the patient and required for use in treatment or prophylaxis according to the present invention will vary with the route of administration, the nature and severity of the condition for which treatment or prophylaxis is required, the age, weight and condition of the patient, concomitant medication and will be ultimately at the discretion of the attendant physician. In general, however, the SGLT2 inhibitor according to this invention is included in the pharmaceutical composition or dosage form in an amount sufficient that by its administration the glycemic control in the patient to be treated is improved.

For the treatment of hyperuricemia or hyperuricemia associated conditions the SGLT2 inhibitor according to this invention is included in the pharmaceutical composition or dosage form in an amount sufficient that is sufficient to treat hyperuricemia without disturbing the patient's plasma glucose homeostasis, in particular without inducing hypoglycemia.

For the treatment or prevention of kidney stones the SGLT2 inhibitor according to this invention is included in the pharmaceutical composition or dosage form in an amount sufficient that is sufficient to treat or prevent kidney stones without disturbing the patient's plasma glucose homeostasis, in particular without inducing hypoglycemia.

For the treatment of hyponatremia and associated conditions the SGLT2 inhibitor according to this invention is included in the pharmaceutical composition or dosage form in an amount sufficient that is sufficient to treat hyponatremia or the associated conditions without disturbing the patient's plasma glucose homeostasis, in particular without inducing hypoglycemia.

In the following preferred ranges of the amount of the SGLT2 inhibitor to be employed in the pharmaceutical composition and the methods and uses according to this invention are described. These ranges refer to the amounts to be administered per day with respect to an adult patient, in particular to a human being, for example of approximately 70 kg body weight, and can be adapted accordingly with regard to an administration 2, 3, 4 or more times daily and with regard to other routes of administration and with regard to the age of the patient. Within the scope of the present invention, the pharmaceutical composition is preferably administered orally. Other forms of administration are possible and described hereinafter. Preferably the one or more dosage forms comprising the SGLT2 inhibitor is oral or usually well known.

In general, the amount of the SGLT2 inhibitor in the pharmaceutical composition and methods according to this invention is preferably the amount usually recommended for a monotherapy using said SGLT2 inhibitor.

The preferred dosage range of the SGLT2 inhibitor is in the range from 0.5 mg to 200 mg, even more preferably from 1 to 100 mg, most preferably from 1 to 50 mg per day. In one aspect, a preferred dosage of the SGLT2 inhibitor empagliflozin is 10 mg or 25 mg per day. The oral administration is preferred. Therefore, a pharmaceutical composition may comprise the hereinbefore mentioned amounts, in particular from 1 to 50 mg or 1 to 25 mg. Particular dosage strengths (e.g. per tablet or capsule) are for example 1, 2.5, 5, 7.5, 10, 12.5, 15, 20, 25 or 50 mg of the SGLT2 inhibitor, in particular empagliflozin. In one aspect, a pharmaceutical composition comprises 10 mg or 25 mg of empagliflozin. The application of the active ingredient may occur up to three times a day, preferably one or two times a day, most preferably once a day.

A pharmaceutical composition which is present as a separate or multiple dosage form, preferably as a kit of parts, is useful in combination therapy to flexibly suit the individual therapeutic needs of the patient.

According to a first embodiment a preferred kit of parts comprises a containment containing a dosage form comprising the SGLT2 inhibitor and at least one pharmaceutically acceptable carrier.

A further aspect of the present invention is a manufacture comprising the pharmaceutical composition being present as separate dosage forms according to the present invention and a label or package insert comprising instructions that the separate dosage forms are to be administered in combination or alternation.

According to a first embodiment a manufacture comprises (a) a pharmaceutical composition comprising a SGLT2 inhibitor according to the present invention and (b) a label or package insert which comprises instructions that the medicament is to be administered.

The desired dose of the pharmaceutical composition according to this invention may conveniently be presented in a once daily or as divided dose administered at appropriate intervals, for example as two, three or more doses per day.

The pharmaceutical composition may be formulated for oral, rectal, nasal, topical (including buccal and sublingual), transdermal, vaginal or parenteral (including intramuscular, sub-cutaneous and intravenous) administration in liquid or solid form or in a form suitable for administration by inhalation or insufflation. Oral administration is preferred. The formulations may, where appropriate, be conveniently presented in discrete dosage units and may be prepared by any of the methods well known in the art of pharmacy. All methods include the step of bringing into association the active ingredient with one or more pharmaceutically acceptable carriers, like liquid carriers or finely divided solid carriers or both, and then, if necessary, shaping the product into the desired formulation.

The pharmaceutical composition may be formulated in the form of tablets, granules, fine granules, powders, capsules, caplets, soft capsules, pills, oral solutions, syrups, dry syrups, chewable tablets, troches, effervescent tablets, drops, suspension, fast dissolving tablets, oral fast-dispersing tablets, etc.

The pharmaceutical composition and the dosage forms preferably comprises one or more pharmaceutical acceptable carriers which must be "acceptable" in the sense of being compatible with the other ingredients of the formulation and not deleterious to the recipient thereof. Examples of pharmaceutically acceptable carriers are known to the one skilled in the art.

Pharmaceutical compositions suitable for oral administration may conveniently be presented as discrete units such as capsules, including soft gelatin capsules, cachets or tablets each containing a predetermined amount of the active ingredient; as a powder or granules; as a solution, a suspension or as an emulsion, for example as syrups, elixirs or self-emulsifying delivery systems (SEDDS). The active ingredients may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The pharmaceutical composition according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilisation from solution, for constitution with a suitable vehicle, e.g. sterile, pyrogen-free water, before use.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the active compound(s) with the softened or melted carrier(s) followed by chilling and shaping in moulds.

The pharmaceutical compositions and methods according to this invention show advantageous effects in the treatment and prevention of those diseases and conditions as described hereinbefore. Advantageous effects may be seen for example with respect to efficacy, dosage strength, dosage frequency, pharmacodynamic properties, pharmacokinetic properties, fewer adverse effects, convenience, compliance, etc.

Methods for the manufacture of SGLT2 inhibitors according to this invention and of prodrugs thereof are known to the one skilled in the art. Advantageously, the compounds according to this invention can be prepared using synthetic methods as described in the literature, including patent applications as cited hereinbefore. Preferred methods of manufacture are described in the WO 2006/120208 and WO 2007/031548. With regard to empagliflozin an advantageous crystalline form is described in the international patent application WO 2006/117359 which hereby is incorporated herein in its entirety.

The active ingredients may be present in the form of a pharmaceutically acceptable salt. Pharmaceutically acceptable salts include, without being restricted thereto, such as salts of inorganic acid like hydrochloric acid, sulfuric acid and phosphoric acid; salts of organic carboxylic acid like oxalic acid, acetic acid, citric acid, malic acid, benzoic acid, maleic acid, fumaric acid, tartaric acid, succinic acid and glutamic acid and salts of organic sulfonic acid like methanesulfonic acid and p-toluenesulfonic acid. The salts can be formed by combining the compound and an acid in the appropriate amount and ratio in a solvent and decomposer. They can be also obtained by the cation or anion exchange from the form of other salts.

The active ingredients or a pharmaceutically acceptable salt thereof may be present in the form of a solvate such as a hydrate or alcohol adduct.

Pharmaceutical compositions or combinations for use in these therapies comprising the SGLT-2 inhibitor as defined herein optionally together with one or more other active substances are also contemplated.

Further, the present invention relates to the SGLT-2 inhibitors, optionally in combination with one, two or more further active agents, each as defined herein, for use in the therapies as described herein.

Further, the present invention relates to the use of the SGLT-2 inhibitors, optionally in combination with one, two or more further active agents, each as defined herein, for preparing pharmaceutical compositions which are suitable for the treatment and/or prevention purposes of this invention.

The present invention further relates to a pharmaceutical composition comprising a certain SGLT-2 inhibitor as defined herein, preferably empagliflozin, and metformin and/or a DPP-4 inhibitor, for example linagliptin, for use in the therapies described herein.

The present invention further relates to a combination comprising a certain SGLT-2 inhibitor (particularly empagliflozin) and one or more other antidiabetics selected from the group consisting of metformin, a sulphonylurea, nateglinide, repaglinide, a thiazolidinedione, an alpha-glucosidase inhibitor, insulin or an insulin analogue, GLP-1 or a GLP-1 analogue and a DPP-4 inhibitor, particularly for simultaneous, separate or sequential use in the therapies described herein.

The present invention further relates to a method for treating and/or preventing metabolic diseases, especially type 2 diabetes mellitus and/or conditions related thereto (e.g. diabetic complications) comprising the combined (e.g. simultaneous, separate or sequential) administration of an effective amount of one or more other antidiabetics selected from the group consisting of metformin, a sulphonylurea, nateglinide, repaglinide, a thiazolidinedione, a PPAR-gamma-agonist, an alpha-glucosidase inhibitor, insulin or an insulin analogue, GLP-1 or a GLP-1 analogue and a DPP-4 inhibitor, to the patient (particularly human patient) in need thereof, such as e.g. a patient as described herein.

The present invention further relates to therapies or therapeutic methods described herein, such as e.g. a method for treating and/or preventing metabolic diseases, especially type 2 diabetes mellitus and/or conditions related thereto (e.g. diabetic complications), comprising administering a therapeutically effective amount of empagliflozin and, optionally, one or more other therapeutic agents, such as e.g. antidiabetics selected from the group consisting of metformin, a sulphonylurea, nateglinide, repaglinide, a thiazolidinedione, a PPAR-gamma-agonist, an alpha-glucosidase inhibitor, insulin or an insulin analogue, GLP-1 or a GLP-1 analogue and a DPP-4 inhibitor, to the patient (particularly human patient) in need thereof, such as e.g. a patient as described herein.

Within this invention it is to be understood that the combinations, compositions or combined uses according to this invention may envisage the simultaneous, sequential or separate administration of the active components or ingredients.

In this context, "combination" or "combined" within the meaning of this invention may include, without being limited, fixed and non-fixed (e.g. free) forms (including kits) and uses, such as e.g. the simultaneous, sequential or separate use of the components or ingredients.

The combined administration of this invention may take place by administering the active components or ingredients together, such as e.g. by administering them simultaneously in one single or in two separate formulations or dosage forms. Alternatively, the administration may take place by administering the active components or ingredients sequentially, such as e.g. successively in two separate formulations or dosage forms.

For the combination therapy of this invention the active components or ingredients may be administered separately (which implies that they are formulated separately) or formulated altogether (which implies that they are formulated in the same preparation or in the same dosage form). Hence, the administration of one element of the combination of the present invention may be prior to, concurrent to, or subsequent to the administration of the other element of the combination.

Unless otherwise noted, combination therapy may refer to first line, second line or third line therapy, or initial or add-on combination therapy or replacement therapy.

The present invention further relates to a certain SGLT-2 inhibitor as defined herein, preferably empagliflozin, in combination with metformin, for use in the therapies described herein.

Metformin is usually given in doses varying from about 500 mg to 2000 mg up to 2500 mg per day using various dosing regimens from about 100 mg to 500 mg or 200 mg to 850 mg (1-3 times a day), or about 300 mg to 1000 mg once or twice a day, or delayed-release metformin in doses of about 100 mg to 1000 mg or preferably 500 mg to 1000 mg once or twice a day or about 500 mg to 2000 mg once a day. Particular dosage strengths may be 250, 500, 625, 750, 850 and 1000 mg of metformin hydrochloride.

For children 10 to 16 years of age, the recommended starting dose of metformin is 500 mg given once daily. If this dose fails to produce adequate results, the dose may be increased to 500 mg twice daily. Further increases may be made in increments of 500 mg weekly to a maximum daily dose of 2000 mg, given in divided doses (e.g. 2 or 3 divided doses). Metformin may be administered with food to decrease nausea.

An example of a DPP-4 inhibitor is linagliptin, which is usually given in a dosage of 5 mg per day. Therefore, a pharmaceutical composition may comprise 5 mg linagliptin in addition to the SGLT2 inhibitor, in particular empagliflozin in an amount of 10 mg or 25 mg.

A dosage of pioglitazone is usually of about 1-10 mg, 15 mg, 30 mg, or 45 mg once a day.

Rosiglitazone is usually given in doses from 4 to 8 mg once (or divided twice) a day (typical dosage strengths are 2, 4 and 8 mg).

Glibenclamide (glyburide) is usually given in doses from 2.5-5 to 20 mg once (or divided twice) a day (typical dosage strengths are 1.25, 2.5 and 5 mg), or micronized glibenclamide in doses from 0.75-3 to 12 mg once (or divided twice) a day (typical dosage strengths are 1.5, 3, 4.5 and 6 mg).

Glipizide is usually given in doses from 2.5 to 10-20 mg once (or up to 40 mg divided twice) a day (typical dosage strengths are 5 and 10 mg), or extended-release glibenclamide in doses from 5 to 10 mg (up to 20 mg) once a day (typical dosage strengths are 2.5, 5 and 10 mg).

Glimepiride is usually given in doses from 1-2 to 4 mg (up to 8 mg) once a day (typical dosage strengths are 1, 2 and 4 mg).

The non-sulphonylurea insulin secretagogue nateglinide is usually given in doses from 60 to 120 mg with meals (up to 360 mg/day, typical dosage strengths are 60 and 120 mg); repaglinide is usually given in doses from 0.5 to 4 mg with meals (up to 16 mg/day, typical dosage strengths are 0.5, 1 and 2 mg). A dual combination of repaglinide/metformin is available in dosage strengths of 1/500 and 2/850 mg.

Further embodiments, features and advantages of the present invention may become apparent from the following examples. The following examples serve to illustrate, by way of example, the principles of the invention without restricting it.

EXAMPLES

Example 1: Empagliflozin in Patients with Type 2 Diabetes Mellitus (T2DM) and Renal Impairment (RI)

A Phase III trial investigated the efficacy and safety of empagliflozin (EMPA) as add-on to existing therapy for 52 weeks in patients with T2DM and RI. Patients with mild RI (eGFR [MDRD equation]≥60 to <90 mL/min/1.73 m$^2$; n=290; mean age 62.6 years; mean BMI 31.5 kg/m$^2$) received EMPA 10 or 25 mg qd or placebo (PBO). Patients with moderate RI (eGFR ≥30 to <60 mL/min/1.73 m$^2$; n=374; mean age 64.9 years; mean BMI 30.2 kg/m$^2$) received EMPA 25 mg qd or PBO. The primary endpoint was change from baseline in HbA$_{1c}$ at week 24. Exploratory endpoints included changes from baseline in fasting plasma glucose (FPG), weight and blood pressure (BP) at week 24 (FIG. 1).

EMPA significantly reduced HbA$_{1c}$ vs PBO at week 24. Further analyses showed significant reductions in FPG, weight and BP. At week 24, adverse events (AEs) were reported by 79.6%, 75.4% and 72.7% of all patients (including an exploratory group with severe RI [n=74] on EMPA 25 mg or PBO) on EMPA 10 mg, 25 mg and PBO, respectively. Hypoglycemia (plasma glucose ≤70 mg/dL and/or requiring assistance) was reported in 23.5% of patients on EMPA 10 mg, 22.1% on EMPA 25 mg and 22.9% on PBO. AEs consistent with urinary tract infection were reported in 10.2% of patients on EMPA 10 mg, 9.0% on EMPA 25 mg and 8.2% on PBO. AEs consistent with genital infection were reported in 6.1% of patients on EMPA 10 mg, 2.5% on EMPA 25 mg and 1.3% on PBO.

To conclude, in patients with T2DM and mild or moderate RI, EMPA reduced $HbA_{1c}$, weight, and BP vs PBO, and was well tolerated.

The primary endpoint was also analysed for patients with moderate A and moderate B renal impairment. For the patients with moderate A renal impairment, the difference to placebo for the adjusted mean change in $HbA_{1c}$ from baseline at Week 24 was −0.46% (95% CI: −0.66, −0.27). For the patients with moderate B renal impairment, the difference to placebo for the adjusted mean change in $HbA_{1c}$ from baseline at Week 24 was −0.39% (95% CI: −0.58, −0.19).

Example 2: Mixed Effects Modeling to Quantify the Effect of Empagliflozin Exposure on the Renal Glucose Threshold in Patients with Type 2 Diabetes Mellitus Empagliflozin, a selective and potent SGLT2 inhibitor, reduces renal glucose reabsorption by lowering the renal threshold for glucose ($RT_G$) leading to increased urinary glucose excretion (UGE) and decreased plasma glucose (PG) in patients with type 2 diabetes mellitus (T2DM). This analysis aimed to quantify the impact of empagliflozin on $RT_G$ by characterizing the relationship between empagliflozin exposure and UGE in patients with T2DM using nonlinear mixed-effects modeling.

A pharmacokinetic (PK)-pharmacodynamic (PD) model was developed using UGE, PG, PK and estimated glomerular filtration rate (eGFR) data from three Phase I/II trials (N=223; placebo, empagliflozin 1 to 100 mg once daily [QD]). The model assumed that when PG>$RT_G$, UGE increased with increasing PG and eGFR; and when PG≤$RT_G$ slight glucose leakage into urine occurred (estimated as fraction reabsorbed [FRAC]). Reabsorption was estimated by a nonlinear function parameterized in terms of maximum reabsorbed glucose concentration ($G_{max}$) and PG concentration to reach half maximum transport ($K_m$). Maximum inhibitory effect ($I_{max}$) and half maximal inhibitory concentration ($IC_{50}$) described inhibition of renal glucose absorption. $RT_G$ was calculated as the difference between maximum reabsorption (including drug effect) and $K_M$. The model was evaluated via bootstrap and external predictive check of an empagliflozin renal impairment study.

The parameter estimates (95% CI) were $G_{max}$: 374 (347, 391) mg/dL; $K_m$: 144 (113, 163) mg/dL; $I_{max}$: 0.559 (0.545, 0.607); $IC_{50}$: 5.28 (3.53, 8.91) nmol/L; FRAC: 0.999 (0.998, 0.999).

The calculated $RT_G$ for placebo was 230 mg/dL. $RT_G$ decreased with increasing empagliflozin concentration; doses of 1, 5, 10, and 25 mg yielded $RT_G$ values of 100.5, 43.8, 33.1, and 26.0 mg/dL, respectively. External predictive check demonstrated unbiased prediction of UGE across a range of eGFR values (end-stage renal disease to normal renal function). Simulation indicated that for 10 and 25 mg QD, >50% and 90% of subjects, respectively, maintained steady-state empagliflozin concentrations >$IC_{80}$ for $RT_G$ lowering over the dosing interval.

Example 3: Pharmacokinetics and Pharmacodynamics of Empagliflozin in Subjects with Renal Impairment Subjects.

Male and female subjects aged 18 to 75 years weighing at least 45 kg (females only) and with a body mass index (BMI) of 18 to 34 kg/m² were eligible for inclusion in this study. Participants with normal renal function (eGFR >90 mL/min/1.73 m²; control) were required to have T2DM. Patients with mild renal impairment (eGFR 60-89 mL/min/1.73 m²), moderate renal impairment (eGFR 30-59 mL/min/1.73 m²), severe renal impairment (eGFR <30 mL/min/1.73 m²) or renal failure/ESRD (requiring dialysis) did not need to have T2DM. eGFR was calculated using the Modification of Diet in Renal Disease (MDRD) formula: 186×serum creatinine$^{-1.154}$×age$^{-0.203}$×[0.742 if female].

Subjects were excluded from the study if they had recently participated in a study (multiple-dose: within 2 months; single-dose: within 1 month), were abusing alcohol (males >60 g/day; females >40 g/day) or drugs, had donated >100 mL blood in the previous 4 weeks, were taking concomitant medications known to inhibit or induce p-glycoprotein or cytochrome P450 3A, or had any medical or laboratory results deviating from normal and of clinical relevance.

Subjects with renal impairment were excluded if they had significant diseases other than renal impairment or T2DM, including moderate and severe concurrent hepatic impairment, hemoglobin <8 g/dL indicating severe renal anemia (erythropoietin could be used to maintain hemoglobin levels), and intake of drugs with a long half-life (>24 h) within the previous month (or within 10 half-lives of that drug, if longer), except for those being taken for the treatment of renal disease.

The investigators, in cooperation with nephrology centers, aimed to recruit 8 subjects for every group. Subjects with normal renal function were matched to those in the renal impairment groups by age (±5 years) and weight (±15%), where possible.

Study Design.

This 2-center, open-label, parallel-group study was undertaken to assess the effect of renal function on the pharmacokinetics, pharmacodynamics, and safety of a single 50 mg dose of empagliflozin. Subjects were screened for eligibility up to 21 days prior to study drug administration. Following an overnight fast, subjects were admitted to the research unit and received a 50 mg dose of empagliflozin with 240 mL of water (day 1). Water was allowed ad libitum except for 1 h before and 1 h after study drug administration. Following medical surveillance for 24 h, subjects were discharged (day 2) and were monitored as outpatients until they attended an end-of-study examination (within 14 days after the last trial procedure).

Pharmacokinetic Endpoints.

One objective of the study was to determine the effect of renal impairment on the relative bioavailability of empagliflozin, based on the primary endpoints of $AUC_{0-\infty}$ and $C_{max}$. Secondary pharmacokinetic endpoints included: $t_{max}$, $t_{1/2}$, $fe_{0-96}$, $CL_{R,0-96}$, and plasma protein binding of empagliflozin.

Pharmacodynamic Endpoint.

The pharmacodynamic endpoint of the study was the cumulative amount of UGE over a 24 h period following drug administration ($UGE_{0-24}$), relative to baseline, with a baseline measurement obtained over 24 h preceding administration of study drug.

Sample Collection and Analysis.

Approximately 124 mL of blood was taken from every subject over the course of the study for clinical laboratory tests (44 mL), pharmacokinetic assessments (50 mL), and determination of protein binding (30 mL). Blood samples for clinical laboratory testing were collected after subjects had fasted for at least 10 h.

For quantification of empagliflozin plasma concentrations 2.7 mL of blood was taken from a forearm vein in a $K_3$-EDTA (tripotassium ethylenediaminetetraacetic acid)-anticoagulant blood drawing tube at pre-dose and 0.33, 0.67, 1, 1.5, 2, 2.5, 3, 4, 6, 8, 10, 12, 14, 24, 36, 48, 72, and 96 h post-dose. Within 30 min of collection, the samples were centrifuged for 10 min at 2000-4000 g and 4-8° C. The EDTA plasma obtained was stored at −18° C. until it was shipped on dry ice for analysis.

Urine was collected over 24 h prior to drug administration and at the following intervals following drug administration: 0-4, 4-8, 8-12, 12-24, 24-36, 36-48, 48-72, and 72-96 h. Urine containers were weighed empty and at the end of every sampling period and the difference was recorded as the urine volume (weight was set equal to volume, i.e. 1 kg=1 L). Urine containers were refrigerated until 25 h after drug administration and aliquots were stored at −18° C. until shipped on dry ice for analysis.

Empagliflozin concentrations in plasma and urine were determined by validated high performance liquid chromatography, tandem mass spectrometry (HPLC-MS/MS) assays. Empagliflozin and the internal standard [$^{13}C_6$]-empagliflozin were extracted from urine or plasma by supported liquid extraction. After evaporation under nitrogen, the residue was reconstituted and analyzed using liquid chromatography with MS/MS detection. The lower limit of quantification for empagliflozin in human plasma was 1.11 nmol/L, with linearity to 1110 nmol/L using a sample volume of 0.15 mL, and in human urine was 4.44 nmol/L, with linearity to 4440 nmol/L using a sample volume of 0.05 mL. For both plasma and urine, results were calculated using peak area ratios and calibration curves were created using weighted ($1/x^2$) quadratic regression.

For determination of protein binding of empagliflozin, 10 mL blood was collected at pre-dose, 1.5 and 3 h post-dose. Blood was centrifuged for 10 min at 4000 g and 4° C., and the plasma was stored at −20° C. until it was shipped on dry ice for analysis. The binding of empagliflozin and the internal standard [$^{13}C_6$]-empagliflozin to human plasma protein was determined by equilibrium dialysis at 37° C. As a quality control measure, protein binding analyses were performed using the pre-dose plasma samples.

Figure 4B:
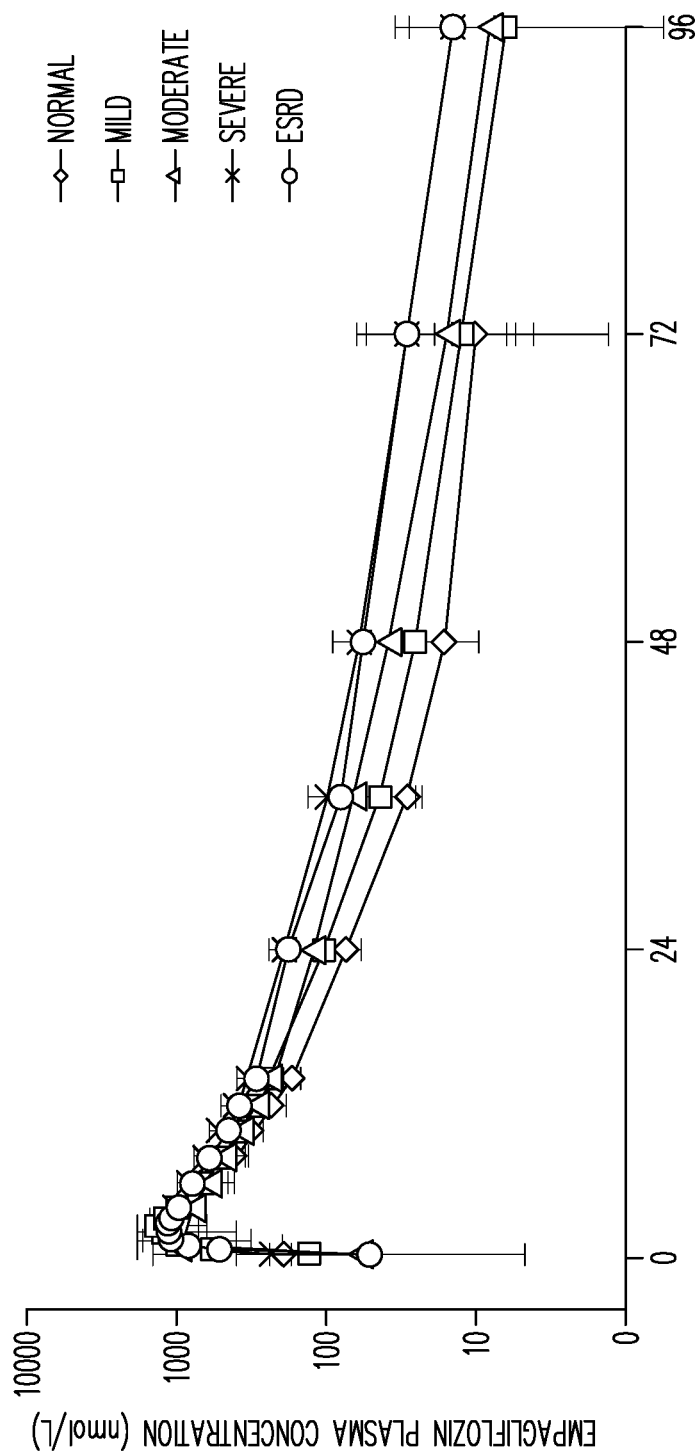
Figure 4C:
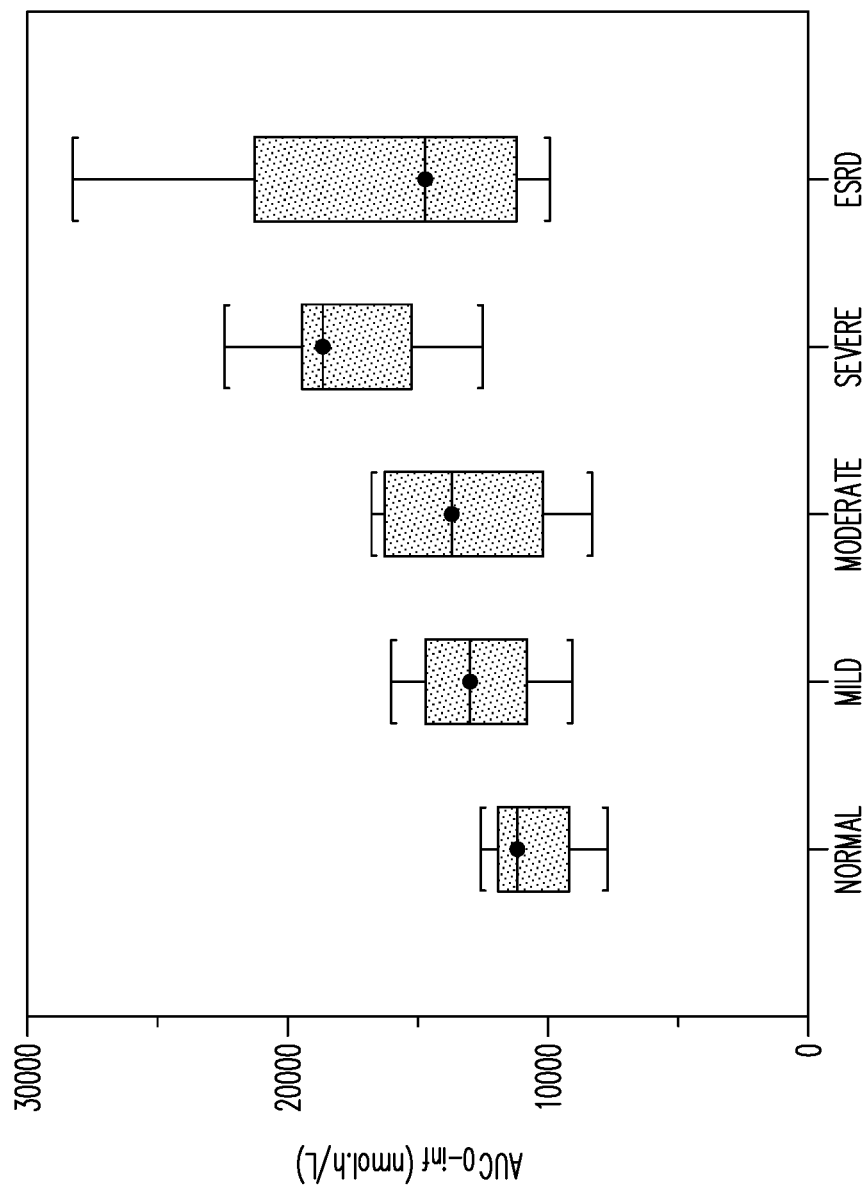
Figure 4D:
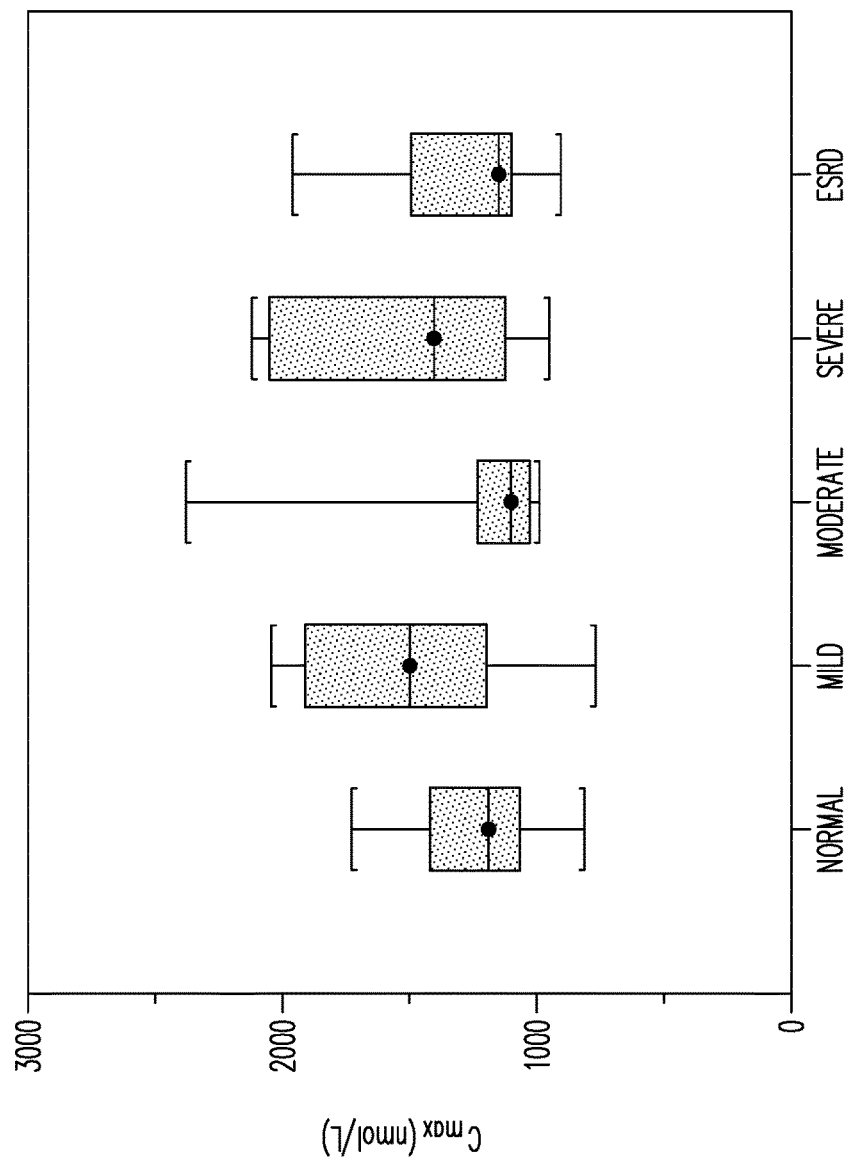
Figure 5A:
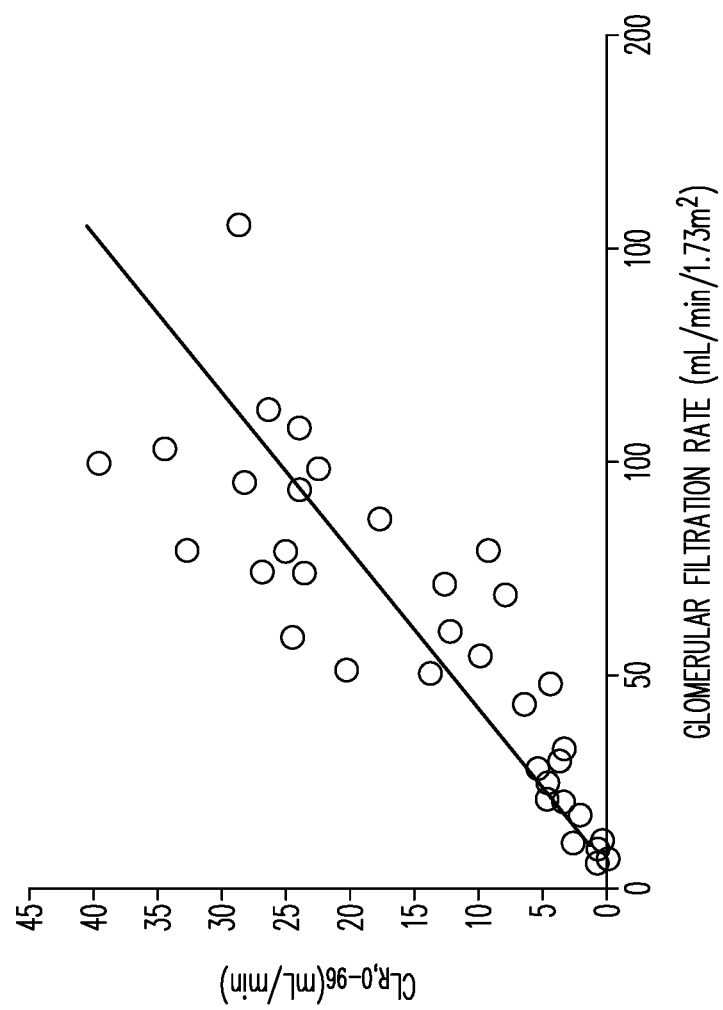
FIG. 5 A-C: (A) $CL_R$ from 0-96 h; (B) $AUC_{0-\infty}$, and (C) cumulative amount of glucose excreted in urine in 24 h versus estimated glomerular filtration rate after administration of a single oral 50 mg dose in subjects with normal and impaired renal function (n=40).
Figure 5B:
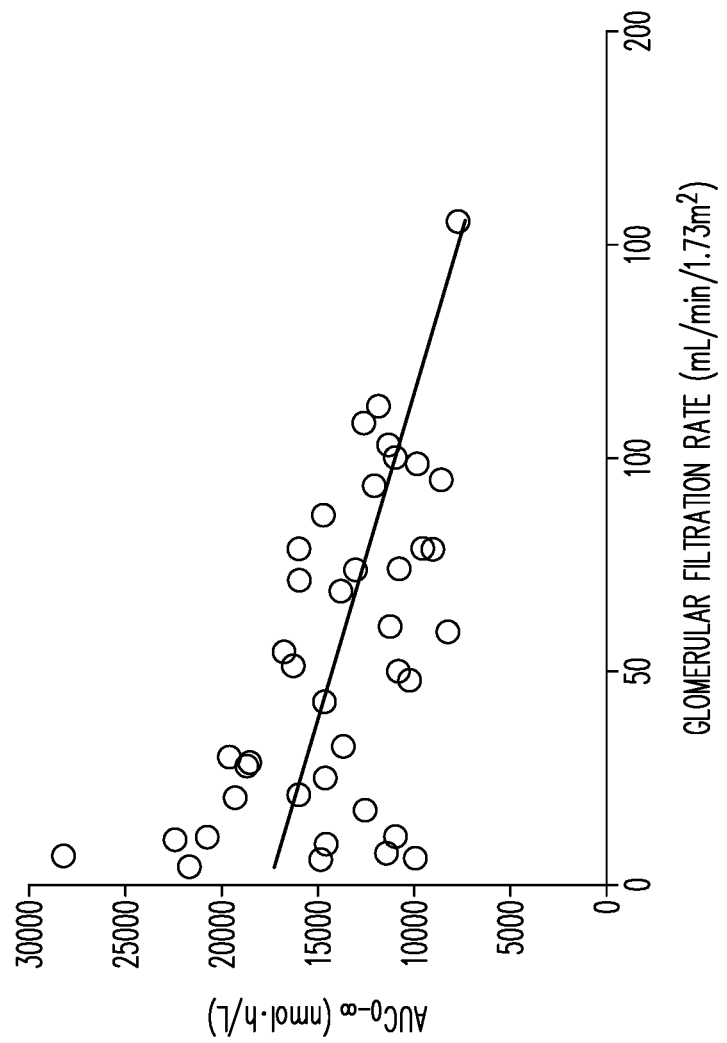
Figure 5C:
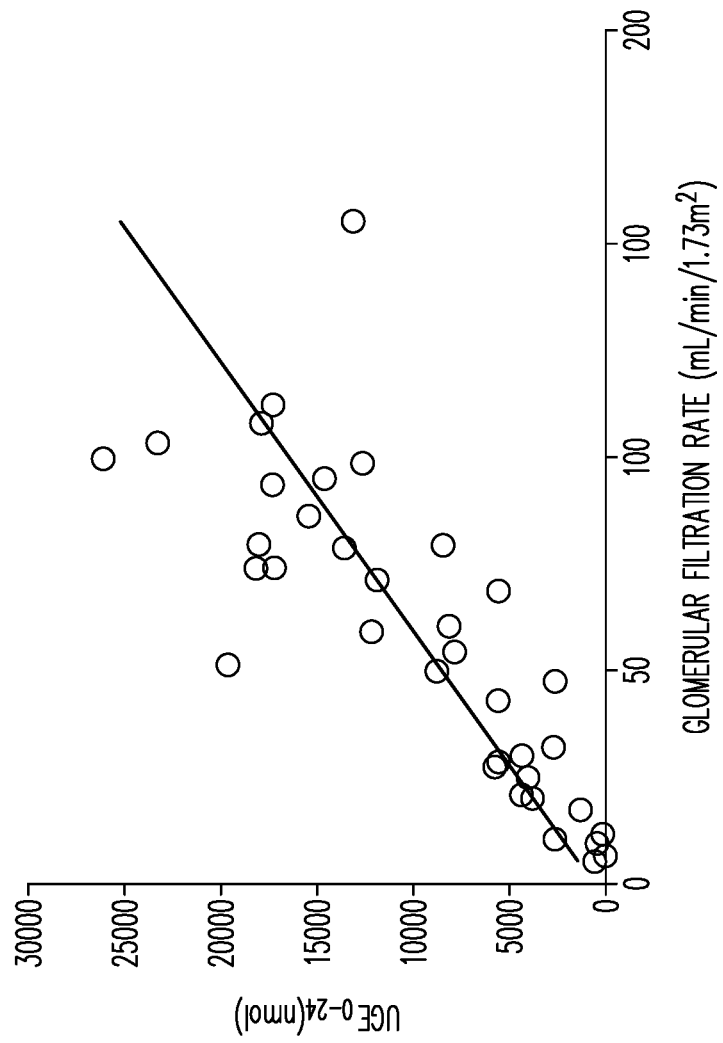
Figure 6:
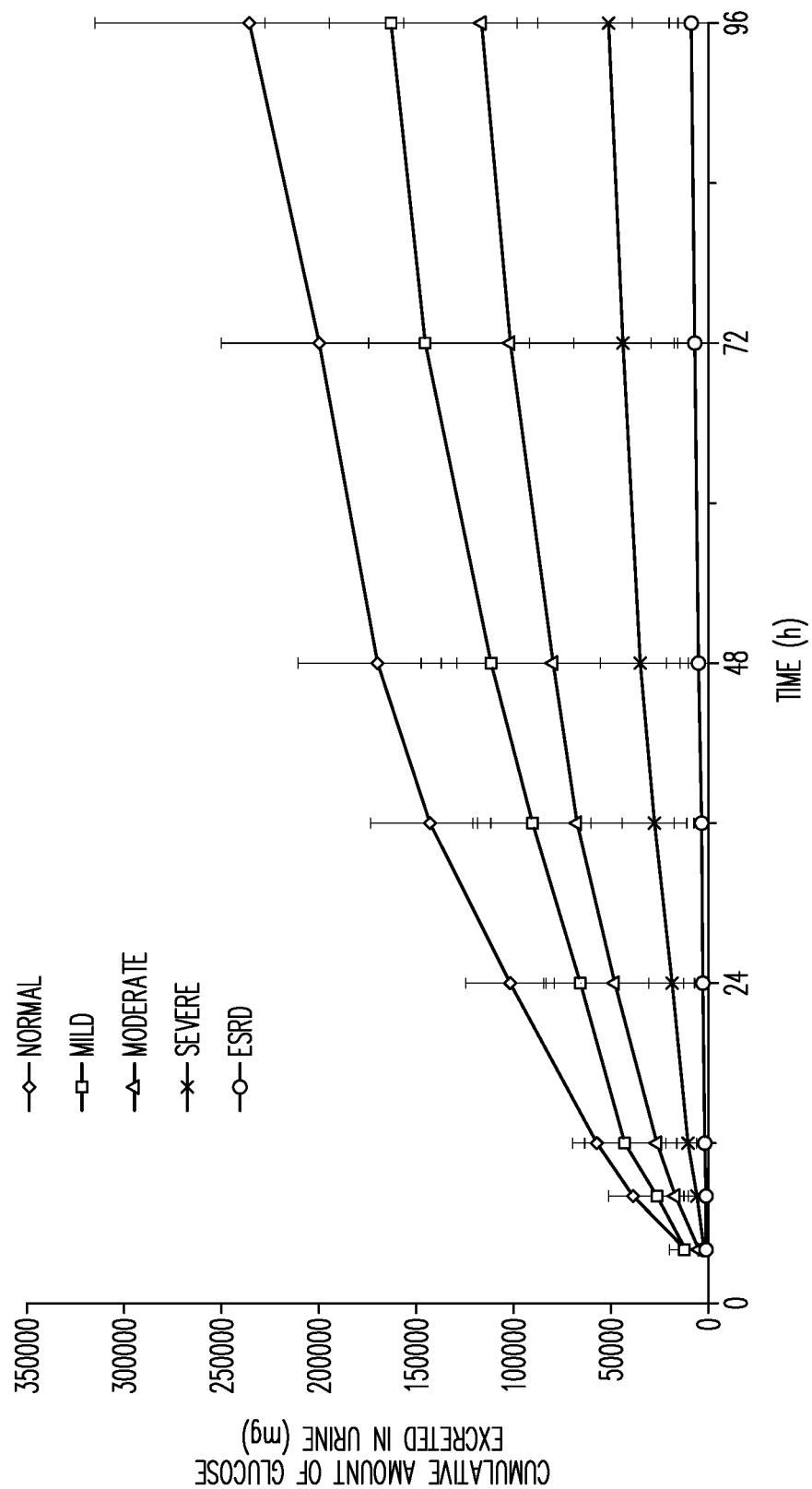
FIG. 6: Mean cumulative amounts of glucose excreted in urine after administration of a single oral 50 mg dose in subjects with normal and impaired renal function (n=31).

Pharmacokinetic parameters were calculated using WinNonlin™ software (v5.01, Pharsight Corporation, Mountain View, Calif., USA). $C_{max}$ and $t_{max}$ values were directly determined from the plasma concentration time profiles of each subject. The apparent terminal rate constant ($\lambda_z$) was estimated from a regression of ln(C) versus time over the terminal log-linear drug disposition portion of the concentration-time profiles. The $t_{1/2}$ was calculated as the quotient of ln(2) and $\lambda_z$. Area under the plasma concentration-time curve to the last time point ($AUC_{0-tz}$) was calculated using the linear trapezoidal method for ascending concentrations and the log trapezoidal method for descending concentrations. The $AUC_{0-\infty}$ value was estimated as the sum of AUC to the last measured concentration, with the extrapolated area given by the quotient of the last measured concentration and $\lambda_z$. The amount of drug ($A_e$) excreted unchanged in urine in each collection interval was determined by the product of the urine concentration and the urine volume. The fraction of the dose ($f_e$) that was excreted unchanged in urine was determined by the quotient of the sum of drug excreted over all dosing intervals and the dose administered. Renal clearance ($CL_R$) was determined as the quotient of $A_e$ over AUC. Cumulative UGE was calculated using the glucose concentration measured in every urine sample collected from −24-0 h and 0-96 h after dosing. UGE (mg) was calculated as follows: glucose concentration [mg/dL]×urine volume [dL]). Results are shown in FIGS. 2 to 6.

Statistical Analysis.

All subjects who provided at least one observation for at least one primary endpoint without any protocol violations relevant to pharmacokinetic evaluation were included in the analysis of relative bioavailability (pharmacokinetic analysis set). All subjects with a baseline UGE value (0-24 h pre-dose) and a UGE value from 0-24 h post-dose without any protocol violations relevant to UGE analysis were included in the UGE analysis set. All safety analyses were performed on all subjects who received study drug (treated set). One objective of the study was to investigate the relative bioavailability of empagliflozin in subjects with normal renal function (R) compared with subjects with various degrees of renal impairment (T1-4), by presenting point estimators (adjusted geometric mean [gMean] T/R ratios) of $AUC_{0-\infty}$ and $C_{max}$ and their 2-sided 90% CIs. $AUC_{0-\infty}$ and $C_{max}$ were analyzed using an analysis of variance (ANOVA) model on the logarithmic scale including a fixed effect corresponding to the renal function (normal, mild impairment, moderate impairment, severe impairment, or renal failure/ESRD). The change in UGE 0-24 h from baseline after drug administration was analyzed by an analysis of covariance (ANCOVA) model including baseline UGE values as a continuous covariate, and a fixed effect corresponding to the renal function. Descriptive statistics were calculated for all pharmacokinetic and pharmacodynamic parameters. Safety analyses were descriptive in nature.

Example 4: Empagliflozin in Patients with Type 2 Diabetes Mellitus (T2DM) and Stage 3A, 3B and 4 Chronic Kidney Disease (CKD)

A Phase III trial investigated the efficacy and safety of empagliflozin (EMPA) as add-on to existing therapy for 52 weeks in patients with T2DM and CKD stage 3A, 3B and 4.

Patients with CKD stage 3A (eGFR [MDRD equation] ≥45 to <60 ml/min/1.73 m²; n=180; mean [SD] age 64.5 [8.0] years; mean [SD] BMI 30.5 [5.2] kg/m²), CKD stage 3B (eGFR ≥30 to <45 ml/min/1.73 m²; n=194; mean [SD] age 65.2 [9.0] years; mean [SD] BMI 30.0 [5.4] kg/m²) or CKD stage 4 (eGFR ≥15 to <30 ml/min/1.73 m²; n=74; mean [SD] age 64.1 [11.1] years; mean [SD] BMI 30.4 [5.6] kg/m²) received EMPA 25 mg qd or PBO for 52 weeks. In exploratory analyses, we assessed the long-term efficacy and safety of EMPA, including changes from baseline in $HbA_{1c}$, fasting plasma glucose (FPG), weight and systolic and diastolic blood pressure (SBP and DBP) at week 52 (FIG. 7).

EMPA 25 mg significantly reduced $HbA_{1c}$ vs PBO at week 52 in patients with CKD stage 3A and 3B (Table). EMPA 25 mg did not reduce $HbA_{1c}$ in patients with CKD stage 4 (Table). EMPA significantly reduced FPG, weight, SBP and DBP in patients with CKD stage 3A, and significantly reduced FPG and weight in patients with CKD stage 3B (Table). Reductions in FPG, weight and BP were observed in patients with CKD stage 4 (Table). During 52 weeks' treatment, adverse events (AEs) were reported by 86.8% and 79.8% of patients with CKD stage 3A on EMPA 25 mg and PBO, respectively, by 80.2% and 86.7% of patients with CKD stage 3B on EMPA 25 mg and PBO, respectively, and by 91.9% and 83.8% of patients with CKD stage 4 on EMPA 25 mg and PBO, respectively. AEs consistent with volume depletion were reported by 4.4% and 2.2% of patients with CKD stage 3A on EMPA 25 mg and PBO, respectively, by 3.1% of patients with CKD stage 3B on EMPA 25 mg or PBO, and by 5.4% patients with CKD stage 4 on EMPA 25 mg or PBO. AEs consistent with urinary tract infection were reported by 16.5% and 18.0% of patients with CKD stage 3A on EMPA 25 mg and PBO, respectively, by 16.7% and 13.3% of patients with CKD stage 3B on EMPA 25 mg and PBO, respectively, and by 18.9% and 8.1% of patients with CKD stage 4 on EMPA 25 mg and PBO, respectively.

EMPA 25 mg for 52 weeks was associated with significant and clinically meaningful reductions in $HbA_{1c}$ compared with placebo in patients with T2DM and CKD stage 3A or 3B. EMPA led to favourable reductions in body weight and BP in patients with T2DM and CKD stage 3A, 3B or 4.

Example 5: Treatment of Type 2 Diabetes Mellitus

Treating patients with type 2 diabetes mellitus with empagliflozin, in addition to producing an acute improvement in the glucose metabolic situation, prevents a deterioration in the metabolic situation in the long term. This can be observed is patients are treated for a longer period, e.g. 3 months to 1 year or even 1 to 6 years, with a combination according to the invention and are compared with patients who have been treated with other antidiabetic and/or anti-obesity medicaments. There is evidence of therapeutic success compared with other treatments if no or only a slight increase in the fasting glucose and/or HbA1c value is observed. Further evidence of therapeutic success is obtained if a significantly smaller percentage of the patients treated with a combination according to the invention, compared with patients who have received another treatment, undergo a deterioration in the glucose metabolic position (e.g. an increase in the HbA1c value to >6.5% or >7%) to the point where treatment with an (additional) oral antidiabetic medicament or with insulin or with an insulin analogue is indicated.

Example 6: Treatment of Insulin Resistance

In clinical studies running for different lengths of time (e.g. 2 weeks to 12 months) the success of the treatment is checked using a hyperinsulinaemic euglycaemic glucose clamp study. A significant rise in the glucose infusion rate at the end of the study, compared with the initial value or compared with a placebo group, or a group given a different therapy, proves the efficacy of a treatment according to the invention in the treatment of insulin resistance.

Example 7: Treatment of Hyperglycaemia

In clinical studies running for different lengths of time (e.g. 1 day to 24 months) the success of the treatment in patients with hyperglycaemia is checked by determining the fasting glucose or non-fasting glucose (e.g. after a meal or a loading test with oGTT or a defined meal). A significant fall in these glucose values during or at the end of the study, compared with the initial value or compared with a placebo group, or a group given a different therapy, proves the efficacy of a combination treatment according to the invention in the treatment of hyperglycaemia.

Example of Pharmaceutical Composition and Dosage Form

The following example of solid pharmaceutical compositions and dosage forms for oral administration serves to illustrate the present invention more fully without restricting it to the contents of the example. Further examples of compositions and dosage forms for oral administration, are described in WO 2010/092126. The term "active substance" denotes empagliflozin according to this invention, especially its crystalline form as described in WO 2006/117359 and WO 2011/039107.

| Tablets containing 2.5 mg, 5 mg, 10 mg, 25 mg, 50 mg of active substance ||||||
| --- | --- | --- | --- | --- | --- |
| Active substance | 2.5 mg/ per tablet | 5 mg/ per tablet | 10 mg/ per tablet | 25 mg/ per tablet | 50 mg/ per tablet |
| Wet granulation ||||||
| active substance | 2.5000 | 5.000 | 10.00 | 25.00 | 50.00 |
| Lactose Monohydrate | 40.6250 | 81.250 | 162.50 | 113.00 | 226.00 |
| Microcrystalline Cellulose | 12.5000 | 25.000 | 50.00 | 40.00 | 80.00 |
| Hydroxypropyl Cellulose | 1.8750 | 3.750 | 7.50 | 6.00 | 12.00 |
| Croscarmellose Sodium | 1.2500 | 2.500 | 5.00 | 4.00 | 8.00 |
| Purified Water | q.s. | q.s. | q.s. | q.s. | q.s. |
| Dry Adds ||||||
| Microcrystalline Cellulose | 3.1250 | 6.250 | 12.50 | 10.00 | 20.00 |
| Colloidal silicon dioxide | 0.3125 | 0.625 | 1.25 | 1.00 | 2.00 |
| Magnesium stearate | 0.3125 | 0.625 | 1.25 | 1.00 | 2.00 |
| Total core | 62.5000 | 125.000 | 250.00 | 200.00 | 400.00 |
| Film Coating ||||||
| Film coating system | 2.5000 | 4.000 | 7.00 | 6.00 | 9.00 |
| Purified Water | q.s. | q.s. | q.s. | q.s. | q.s. |
| Total | 65.000 | 129.000 | 257.00 | 206.00 | 409.00 |

Details regarding the manufacture of the tablets, the active pharmaceutical ingredient, the excipients and the film coating system are described in WO 2010/092126, in particular in the Examples 5 and 6, which hereby is incorporated herein in its entirety.

The invention claimed is:

1. A method for improving glycemic control in a patient with type 2 diabetes mellitus comprising administering empagliflozin to the patient if the eGFR of the patient is ≥45 ml/min/1.73 m$^2$ and <60 ml/min/1.73 m$^2$, wherein empagliflozin is administered orally in a total daily amount of 5 mg, 10 mg, 12.5 mg or 25 mg, wherein the glycemic control in said patient is improved, and discontinuing empagliflozin if the eGFR of the patient falls below 45 ml/min/1.73 m$^2$.

2. The method according to claim 1, wherein empagliflozin is administered in a total daily amount of 5 mg.

3. The method according to claim 1, wherein empagliflozin is administered in a total daily amount of 10 mg.

4. The method according to claim 1, wherein empagliflozin is administered in a total daily amount of 12.5 mg.

5. The method according to claim 1, wherein empagliflozin is administered in a total daily amount of 25 mg.

6. The method according to claim 1, further comprising administering metformin to the patient.

7. A method for improving glycemic control in a patient with type 2 diabetes mellitus comprising:
   a) assessing the renal function of a patient;
   b) administering empagliflozin to the patient if the eGFR of the patient is ≥45 ml/min/1.73 m$^2$ and <60 ml/min/1.73 m$^2$, wherein empagliflozin is administered orally in a total daily amount of 5 mg, 10 mg, 12.5 mg or 25 mg,
   wherein the glycemic control in said patient is improved;
   c) discontinuing empagliflozin if the eGFR of the patient falls below 45 ml/min/1.73 m$^2$.

8. The method according to claim 7, wherein empagliflozin is administered in a total daily amount of 5 mg.

9. The method according to claim 7, wherein empagliflozin is administered in a total daily amount of 10 mg.

10. The method according to claim 7, wherein empagliflozin is administered in a total daily amount of 12.5 mg.

11. The method according to claim 7, wherein empagliflozin is administered in a total daily amount of 25 mg.

12. The method according to claim 7, further comprising administering metformin to the patient.

13. A method of treating type 2 diabetes mellitus in a patient comprising administering empagliflozin to the patient if the eGFR of the patient is ≥45 ml/min/1.73 m$^2$ and <60 ml/min/1.73 m$^2$, wherein empagliflozin is administered orally in a total daily amount of 5 mg, 10 mg, 12.5 mg or 25 mg, wherein the glycemic control in said patient is improved, and discontinuing empagliflozin if the eGFR of the patient falls below 45 ml/min/1.73 m$^2$.

14. The method according to claim 13, wherein empagliflozin is administered in a total daily amount of 5 mg.

15. The method according to claim 13, wherein empagliflozin is administered in a total daily amount of 10 mg.

16. The method according to claim 13, wherein empagliflozin is administered in a total daily amount of 12.5 mg.

17. The method according to claim 13, wherein empagliflozin is administered in a total daily amount of 25 mg.

18. The method according to claim 13, further comprising administering metformin to the patient.

19. A method of treating type 2 diabetes mellitus comprising:
   a) assessing the renal function of a patient with type 2 diabetes mellitus;
   b) administering empagliflozin to the patient if the eGFR of the patient is ≥45 ml/min/1.73 m$^2$ and <60 ml/min/1.73 m$^2$, wherein empagliflozin is administered orally in a total daily amount of 5 mg, 10 mg, 12.5 mg or 25 mg, wherein the glycemic control in said patient is improved;
   c) discontinuing empagliflozin if the eGFR of the patient falls below 45 ml/min/1.73 m$^2$.

20. The method according to claim 19, wherein empagliflozin is administered in a total daily amount of 5 mg.

21. The method according to claim 19, wherein empagliflozin is administered in a total daily amount of 10 mg.

22. The method according to claim 19, wherein empagliflozin is administered in a total daily amount of 12.5 mg.

23. The method according to claim 19, wherein empagliflozin is administered in a total daily amount of 25 mg.

24. The method according to claim 19, further comprising administering metformin to the patient.

* * * * *